US009995679B2

(12) United States Patent
Waggoner et al.

(10) Patent No.: US 9,995,679 B2
(45) Date of Patent: Jun. 12, 2018

(54) TARGETED PROBES OF CELLULAR PHYSIOLOGY

(75) Inventors: Alan Waggoner, Pittsburgh, PA (US); Marcel P. Bruchez, Pittsburgh, PA (US); Brigitte F. Schmidt, Pittsburgh, PA (US); Subhasish K. Chakraborty, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 903 days.

(21) Appl. No.: 13/696,877

(22) PCT Filed: May 25, 2011

(86) PCT No.: PCT/US2011/037933
§ 371 (c)(1),
(2), (4) Date: Jun. 5, 2013

(87) PCT Pub. No.: WO2011/150079
PCT Pub. Date: Dec. 1, 2011

(65) Prior Publication Data
US 2013/0244891 A1    Sep. 19, 2013

Related U.S. Application Data

(60) Provisional application No. 61/396,272, filed on May 25, 2010.

(51) Int. Cl.
| G01N 21/64 | (2006.01) |
| C07K 16/00 | (2006.01) |
| C07D 311/90 | (2006.01) |
| G01N 33/533 | (2006.01) |
| G01N 33/542 | (2006.01) |
| G01N 33/58 | (2006.01) |

(52) U.S. Cl.
CPC ........... *G01N 21/64* (2013.01); *C07D 311/90* (2013.01); *C07K 16/00* (2013.01); *G01N 33/533* (2013.01); *G01N 33/542* (2013.01); *G01N 33/582* (2013.01)

(58) Field of Classification Search
CPC ...... C07D 311/90; C07K 16/00; G01N 21/64; G01N 33/533; G01N 33/542; G01N 33/582
See application file for complete search history.

(56) References Cited

U.S. PATENT DOCUMENTS

| 4,215,050 A | 7/1980 | Lantzsch |
| 4,355,023 A | 10/1982 | Ehrlich et al. |
| 4,462,334 A | 7/1984 | Kim |
| 4,704,692 A | 11/1987 | Ladner |
| 4,745,051 A | 5/1988 | Smith et al. |
| 4,946,778 A | 8/1990 | Ladner et al. |
| 5,096,815 A | 3/1992 | Ladner et al. |
| 5,166,320 A | 11/1992 | Wu et al. |
| 5,198,346 A | 3/1993 | Ladner et al. |
| 5,223,409 A | 6/1993 | Ladner et al. |
| 5,270,163 A | 12/1993 | Gold et al. |
| 5,475,096 A | 12/1995 | Gold et al. |
| 5,496,938 A | 3/1996 | Gold et al. |
| 5,567,588 A | 10/1996 | Gold et al. |
| 5,580,737 A | 12/1996 | Polisky et al. |
| 5,591,828 A | 1/1997 | Bosslet et al. |
| 5,637,459 A | 6/1997 | Burke et al. |
| 5,660,985 A | 8/1997 | Pieken et al. |
| 5,683,867 A | 11/1997 | Biesecker et al. |
| 5,702,892 A | 12/1997 | Mulligan-Kehoe |
| 5,707,796 A | 1/1998 | Gold et al. |
| 5,750,373 A | 5/1998 | Garrard et al. |
| 5,763,189 A | 6/1998 | Buechler et al. |
| 5,821,047 A | 10/1998 | Garrard et al. |
| 5,948,635 A | 9/1999 | Kay et al. |
| 6,127,132 A | 10/2000 | Breitling et al. |
| 6,131,580 A | 10/2000 | Ratner et al. |
| 6,248,558 B1 | 6/2001 | Lin et al. |
| 6,407,213 B1 | 6/2002 | Carter et al. |
| 9,249,306 B2 * | 2/2016 | Bruchez ............. C09B 11/02 |
| 2003/0220502 A1 | 11/2003 | Waggoner et al. |
| 2004/0262585 A1 | 12/2004 | Cummins et al. |
| 2006/0029936 A9 | 2/2006 | Lee |
| 2008/0213811 A1 | 9/2008 | Vogel et al. |
| 2010/0124788 A1 | 5/2010 | Sieber |
| 2011/0159519 A1 | 6/2011 | Schmidt et al. |

FOREIGN PATENT DOCUMENTS

| EP | 0043075 A2 | 1/1982 |
| EP | 0368684 A1 | 5/1990 |
| EP | 0404097 A2 | 12/1990 |
| JP | 6447381 A | 2/1989 |

(Continued)

OTHER PUBLICATIONS

Briggs et al., "A pH sensitive fluorescent cyanine dye for biological applications," Chem. Commun., 2000, pp. 2323-2324.*
Babendure et al., Aptamers Switch on Fluorescence of Triphenylmethane Dyes, J. Am. Chem. Soc., 2003, pp. 14716-14717 and S1-S3, vol. 125.
Berlier et al., Quantitative Comparison of Long-Wavelength Alexa Fluor Dyes to Cy Dyes: Fluorescence of the Dyes and their Bioconjugates, The Journal of Histochemistry & Cytochemistry, 2003, pp. 1699-1712, vol. 51, No. 12.
Bielinska et al., The Interaction of Plasmid DNA with Polyamidoamine Dendrimers: Mechanism of Complex Formation and Analysis of Alterations Induced in Nuclease Sensitivity and Transcriptional Activity of the Complexed DNA, Biochimica et Biophysica Acta, 1997, pp. 180-190, vol. 1353.
Boder et al., Directed Evolution of Antibody Fragments with Monovalent Femtomolar Antigen-Binding Affinity, Proc. Natl. Acad. Sci., Sep. 26, 2000, pp. 10701-10705, vol. 97, No. 20.
Brenner et al., GFAP Promoter Directs Astrocyte-Specific Expression in Transgenic Mice, The Journal of Neuroscience, Mar. 1994, pp. 1030-1037, vol. 14, No. 3.
Chao et al., Isolating and Engineering Human Antibodies using Yeast Surface Display, Nature Protocols, 2006, pp. 755-768 and 1-page Erratum, vol. 1, No. 2.

(Continued)

*Primary Examiner* — Galina Yakovleva
(74) *Attorney, Agent, or Firm* — The Webb Law Firm

(57) ABSTRACT

Biosensor comprising an activatable acceptor fluorogen linked via a linker to a donor which transfers energy to the fluorogen on detecting an analyte wherein the fluorogen component reacts and a 100 fold increase in intensity results when the fluorogen interacts non-covalently with an activator e.g. fluorogen activator peptide.

19 Claims, 26 Drawing Sheets

(56) References Cited

FOREIGN PATENT DOCUMENTS

| | | |
|---|---|---|
| JP | 8503994 A | 4/1996 |
| JP | 9104825 A | 4/1997 |
| JP | 2003508065 A | 3/2003 |
| WO | 8801649 A1 | 3/1988 |
| WO | 9106309 A1 | 5/1991 |
| WO | 9119813 A1 | 12/1991 |
| WO | 9206180 A1 | 4/1992 |
| WO | 9219749 A1 | 11/1992 |
| WO | 9220316 A2 | 11/1992 |
| WO | 9222635 A1 | 12/1992 |
| WO | 9304701 A1 | 3/1993 |
| WO | 9311161 A1 | 6/1993 |
| WO | 03014743 A2 | 2/2003 |
| WO | 2004025268 A2 | 3/2004 |
| WO | 2008092041 A2 | 7/2008 |
| WO | 2010096388 A2 | 8/2010 |

OTHER PUBLICATIONS

Colby et al., Potent Inhibition of Huntingtin Aggregation and Cytotoxicity by a Disulfide Bond-Free Single-Domain Intracellular Antibody, PNAS, Dec. 21, 2004, pp. 17616-17621, vol. 101, No. 51.

Coloma et al., Design and Production of Novel Tetravalent Bispecific Antibodies, Nature Biotechnology, Feb. 1997, pp. 159-163, vol. 15.

Cristiano et al., Hepatic Gene Therapy: Adenovirus Enhancement of Receptor-Mediated Gene Delivery and Expression in Primary Hepatocytes, Proc. Natl. Acad. Sci. USA, Mar. 1993, pp. 2122-2126, vol. 90.

Cwirla et al., Peptides on Phage: A Vast Library of Peptides for Identifying Ligands, Proc. Natl. Acad. Sci. USA, Aug. 1990, pp. 6378-6382, vol. 87.

Derossi et al., Cell Internalization of the Third Helix of the Antennapedia Homeodomain Is Receptor-Independent, The Journal of Biological Chemistry, 1996, pp. 18188-18193, vol. 271, No. 30.

Devlin et al., Random Peptide Libraries: A Source of Specific Protein Binding Molecules, Science, Jul. 27, 1990, pp. 404-406, vol. 249.

Fisher et al., Detection and Quantification of β2AR Internalization in Living Cells Using FAP-Based Biosensor Technology, Journal of Biomolecular Screening, 2010, pp. 703-709, vol. 15, No. 6.

Fitzpatrick et al., Fluorogen Activating Peptide Based Energy Transfer Donors for FRET in Living Cells, Biophysical Journal, Mar. 2, 2009, 1 page 294A, vol. 96, No. 3.

Fitzpatrick et al., STED Nanoscopy in Living Cells using Fluorogen Activating Proteins, Bioconjugate Chemistry, 2009, pp. 1843-1847, vol. 20, No. 10.

Flotte et al., Expression of the Cystic Fibrosis Transmembrane Conductance Regulator from a Novel Adeno-Associated Virus Promoter, The Journal of Biological Chemistry, Feb. 15, 1993, pp. 3781-3790, vol. 268, No. 5.

Green et al., Autonomous Functional Domains of Chemically Synthesized Human Immunodeficiency Virus Tat Trans-Activator Protein, Cell, Dec. 23, 1988, pp. 1179-1188, vol. 55.

Grierson et al., Plant Molecular Biology, 2d Ed., 1988, Ch. 7-9, Blackie, Glasgow.

Hanes et al., In Vitro Selection and Evolution of Functional Proteins by Using Ribosome Display, Proc. Natl. Acad. Sci. USA, May 1997, pp. 4937-4942, vol. 94.

Hanes et al., Ribosome Display Efficiently Selects and Evolves High-Affinity Antibodies In Vitro from Immune Libraries, Proc. Natl. Acad. Sci. USA, Nov. 1998, pp. 14130-14135, vol. 95.

He et al., Antibody-Ribosome-mRNA (ARM) Complexes as Efficient Selection Particles for In Vitro Display and Evolution of Antibody Combining Sites, Nucleic Acids Research, 1997, pp. 5132-5134, vol. 25, No. 24.

Hermonat et al., Use of Adeno-Associated Virus as a Mammalian DNA Cloning Vector: Transduction of Neomycin Resistance into Mammalian Tissue Culture Cells, Proc. Natl. Acad. Sci. USA, Oct. 1984, pp. 6466-6470, vol. 81.

Hochman et al., An Active Antibody Fragment (Fv) Composed of the Variable Portions of Heavy and Light Chains, Biochemistry, 1973, pp. 1130-1135, vol. 12, No. 6.

Hoffman et al., Ion Channel Assay Development using Invitrogen's FRET-Based Voltage Sensor Probes, BMG Labtech, Application Note, Oct. 2005, 2 pages, vol. 123.

Holt et al., The Use of Recombinant Antibodies in Proteomics, Current Opinion in Biotechnology 2000, pp. 445-449, vol. 11.

Hung et al., Energy Transfer Primers with 5- or 6-Carboxyrhodamine-6G as Acceptor Chromophores, Analytical Biochemistry, 1996, pp. 165-170, vol. 238, Article No. 0270.

Ike et al., Solid Phase Synthesis of Polynucleotides. VIII. Synthesis of Mixed Oligodeoxyribonucleotides by the Phosphotriester Solid Phase Method, Nucleic Acids Research, 1983, pp. 477-488, vol. 11, No. 2.

Iliades et al., Triabodies: Single Chain Fv Fragments Without a Linker Form Trivalent Trimers, FEBS Letters, 1997, pp. 437-441, vol. 409.

Itakura et al., Chemical Synthesis and Application of Oligonucleotides of Mixed Sequence, Recombinant DNA, Proc. 3rd Cleveland Sympos. Macromolecules, Walton (ed.), Elsevier Scientific Publishing Co., Amsterdam, Jun. 22-26, 1981, pp. 273-289.

Itakura et al., Synthesis and Use of Synthetic Oligonucleotides, Ann. Rev. Biochem., 1984, pp. 323-356, vol. 53.

Itakura et al., Expression in *Escherichia coli* of a Chemically Synthesized Gene for the Hormone Somatostatin, Science, New Series, Dec. 9, 1977, pp. 1056-1063, vol. 198, No. 4321.

Jakobsson et al., Lesion-Dependent Regulation of Transgene Expression in the Rat Brain using a Human Glial Fibrillary Acidic Protein-Lentiviral Vector, European Journal of Neuroscience, 2004, pp. 761-765, vol. 19.

Javed et al., Diazo Preparation via Dehydrogenation of Hydrazones with "Activated" DMSO, Organic Letters, 2007, pp. 1789-1792, vol. 9, No. 9.

Jones et al., Improvements in the Sensitivity of Time Resolved Fluorescence Energy Transfer Assays, 6th International Conference on Methods and Applications of Fluorescence Spectroscopy, Sep. 12-15, 1999, 1 page.

Klajnert et al., Dendrimers: Properties and Applications, Acta Biochimica Polonica, 2001, pp. 199-208, vol. 48, No. 1.

Kuby, Immunology, Third Edition, 1997, pp. 131-139, W. H. Freeman & Co., New York.

Kugler et al., Human Synapsin 1 Gene Promoter Confers Highly Neuron-Specific Long-Term Transgene Expression from an Adenoviral Vector in the Adult Rat Brain Depending on the Transduced Area, Gene Therapy, 2003, pp. 337-347, vol. 10.

Lois et al., GermLine Transmission and Tissue-Specific Expression of Transgenes Delivered by Lentiviral Vectors, Science, Feb. 1, 2002, pp. 868-872, vol. 295.

Martin et al., Mammalian Cell-Based Optimization of the Biarsenical-Binding Tetracysteine Motif for Improved Fluorescence and Affinity, Nature Biotechnology, Sep. 11, 2005, pp. 1-7.

Miller, Progress Toward Human Gene Therapy, Blood, Jul. 15, 1990, pp. 271-278, vol. 76, No. 2.

Mizuno et al., Basic Research for Interferon Gene Therapy Against Malignant Glioma (Abstract), No Shinkei Geka, May 1992, vol. 20, No. 5, Abstract only, 1 page.

Mizuno et al., Growth Inhibition of Glioma Cells by Liposome-Mediated Cell Transfection with Tumor Necrosis Factor-Alpha Gene—its Enhancement by prior Gamma-Interferon Treatment, Neurol. Med. Chir., Nov. 1992, pp. 873-876, vol. 32, No. 12, Abstract only, 1 page.

Mujumdar et al., Cyanine Dye Labeling Reagents: Sulfoindocyanine Succinimidyl Esters, Bioconjugate Chemistry, Mar./Apr. 1993, pp. 105-111, vol. 4, No. 2.

Mulligan, The Basic Science of Gene Therapy, Science, May 14, 1993, pp. 926-932, vol. 260.

Narang, DNA Synthesis, Tetrahedron, 1983, pp. 3-22, vol. 39, No. 1.

Özhalici-Ünal et al., A Rainbow of Fluoromodules: A Promiscuous scFv Protein Binds to and Activates a Diverse Set of Fluorogenic Cyanine Dyes, J Am Chem Soc., Sep. 24, 2008, 8 pages, vol. 130, No. 38.

(56) References Cited

OTHER PUBLICATIONS

Pack et al., Tetravalent Miniantibodies with High Avidity Assembling in *Escherichia coli*, J. Mol. Biol., 1995, pp. 28-34, vol. 246.
Paladino et al., Different GPI-Attachment Signals Affect the Oligomerisation of GPI-Anchored Proteins and their Apical Sorting, Journal of Cell Science, 2008, pp. 4001-4007, vol. 121, No. 24.
Patterson et al., Use of the Green Fluorescent Protein and Its Mutants in Quantitative Fluroescence Microscopy, Biophysical Journal, Nov. 1997, pp. 2782-2790, vol. 73.
Perron et al., Second and Third Generation Voltage-Sensitive Fluorescent Proteins for Monitoring Membrane Potential, Frontiers in Molecular Neuroscience, Jun. 22, 2009, pp. 1-8, vol. 2, Article 5.
Rao et al., Integrating Cell-Level Kinetic Modeling into the Design of Engineered Protein Therapeutics, Nature Biotechnology, Feb. 2005, pp. 191-194, vol. 23, No. 2.
Roberts et al., Directed Evolution of a Protein: Selection of Potent Neutrophil Elastase Inhibitors Displayed on M13 Fusion Phage, Proc. Natl. Acad. Sci. USA, Mar. 1992, pp. 2429-2433, vol. 89.
Rogers et al., Weissbach et al. (ed.), Gene Transfer in Plants: Production of Transformed Plants Using Ti Plasmid Vectors, Methods for Plant Molecular Biology, 1988, Section VIII, pp. 423-463, Academic Press Inc., New York.
Schoch et al., Neuron-Specific Gene Expression of Synapsin I, Major Role of a Negative Regulatory Mechanism, The Journal of Biological Chemistry, Feb. 9, 1996, pp. 3317-3323, vol. 271, No. 6.
Scott et al., Searching for Peptide Ligands with an Epitope Library, Science, Jul. 27, 1990, pp. 386-390, vol. 249.
Shaner et al., Improved Monomeric Red, Orange and Yellow Fluorescent Proteins Derived from *Discosoma* sp. Red Fluorescent Protein, Nature Biotechnology, Dec. 2004, pp. 1567-1572, vol. 22, No. 12.
Shank et al., Enhanced Photostability of Genetically Encodable Fluoromodules Based on Fluorogenic Cyanine Dyes and a Promiscuous Protein Partner, J. Am. Chem. Soc., 2009, pp. 12960-12969, vol. 131.
Sharon et al., Preparation of Fv Fragment from the Mouse Myeloma XRPC-25 Immunoglobulin Possessing Anti-Dinitrophenyl Activity, Biochemistry, 1976, pp. 1591-1594, vol. 15, No. 7.
Swers et al., Shuffled Antibody Libraries Created by In Vivo Homologous Recombination and Yeast Surface Display, Nucleic Acids Research, 2004, 8 pages, vol. 32, No. 3.
Szent-Gyorgyi et al., Fluorogen-Activating Single-Chain Antibodies for Imaging Cell Surface Proteins, Nature Biotechnology, Feb. 2008, pp. 235-240, vol. 26, No. 2.
Szidonya et al., Dimerization and Oligomerization of G-Protein-Coupled Receptors: Debated Structures with Established and Emerging Functions, Journal of Endocrinology, 2008, pp. 435-453, vol. 196.
Tratschin et al., Adeno-Associated Virus Vector for High-Frequency Integration, Expression, and Rescue of Genes in Mammalian Cells, Molecular and Cellular Biology, Nov. 1985, pp. 3251-3260, vol. 5, No. 11.
Vandier et al., Inhibition of Glioma Cells In Vitro and In Vivo using a Recombinant Adenoviral Vector Containing an Astrocyte-Specific Promoter, Cancer Gene Therapy, 2000, pp. 1120-1126, vol. 7, No. 8.
Viac et al., An Immunoelectron Microscopic Localization of Wart Associated Antigens Present in Human Papilloma Virus (HPV) Infected Cells, The Journal of Investigative Dermatology, 1978, pp. 263-266, vol. 70, No. 5.
Wagner et al., Influenza Virus Hemagglutinin HA-2 N-Terminal Fusogenic Peptides Augment Gene Transfer by Transferrin-Polylysine-DNA Complexes: Toward a Synthetic Virus-Like Gene-Transfer Vehicle, Proc. Natl. Acad. Sci. USA, Sep. 1992, pp. 7934-7938, vol. 89.
Ward et al., Binding Activities of a Repertoire of Single Immunoglobulin Variable Domains Secreted from *Escherichia coli*, Nature, Oct. 12, 1989, pp. 544-546, vol. 341.
Weinstock et al., Synthesis and Evaluation of Non-Catechol D-1 and D-2 Dopamine Receptor Agonists: Benzimidazol-2-One, Benzoxazol-2-One, and the Highly Potent Benzothiazol-2-One 7-Ethylamines, Journal of Medicinal Chemistry, 1987, pp. 1166-1176, vol. 30, No. 7.
White et al., Comparison of the Glycosyl-Phosphatidylinositol Cleavage/Attachment Site between Mammalian Cells and Parasitic Protozoa, Journal of Cell Science, 2000, pp. 721-727, vol. 113.
Yeast Display scFv Antibody Library User's Manual Pacific Northwest National Laboratory, Richland, WA 99352, Revision Date: MF031112.
In Vitro Protein Expression Guide, Promega, 2005, pp. 29-33.
Jones et al., Improvements in the Sensitivity of Time Resolved Fluorescence Energy Transfer Assays, Journal of Fluorenscence, 2001, pp. 13-21, vol. 11, No. 1.

* cited by examiner

L5-MG

QAVVTQEPSVTVSPGGTVILTCGSSTGAVTSGHYANWFQQKPGQAPR
ALIFETDKKYPWTPGRFSGSLLGVKAALTISDAQPEDEAEYYCLLSDVDGYL
FGGGTQLTVLS

L5-MG E52D

QAVVTQEPSVTVSPGGTVILTCGSSTGAVTSGHYANWFQQKPGQAPR
ALIF<u>D</u>TDKKY<u>P</u>WTPGRFSGSLLG<u>V</u>KAALTISDAQPEDEAEYYCLLSDVDGYL
FGGGTQLTVLS

L5-MG L91S

QAVVTQEPSVTVSPGGTVILTCGSSTGAVTSGHYANWFQQKPGQAPR
ALIFETDKKYPWTPGRFSGSLLGVKAALTISDAQPEDEAEYYC<u>S</u>LSDVDGYL
FGGGTQLTVLS

L5-MG E52D L91S

QAVVTQEPSVTVSPGGTVILTCGSGTGAVTSGHYANWFQQKPGQAPR
ALIF<u>D</u>TDKKYPWTPGRFSGSLLGVKAALTISDAQPEDEAEYYC<u>S</u>LSDVDGYL
FGGGTQLTVLS

*Figure 1A*

HL4-MG core 251aa

QVQLVESEGGGLVQPGGSLRLSCAASGFTFSSYEMNWVRQAPGKGLEWVSRIDGDGSSTNYADSVKGRFTI
SRDNAKSTLYLQMNSLRAEDTAVYYCTRARYFGSVSPYGMDVWGQGTTVTVSSGILGSGGGGSGGGGSGG
GGSDIRVTQSPSSVSASVGDRVTISCRASQGIATWLGWYQQKPGKPPQLLIYSASTLQTGVPSRFSGSGS
GTDFTLTISSLQPEDVATYYCQEGSTFPLTFGGGTKVDIKS

H6-MG in PNL6 core 130aa

QVQLQESGPGLVKPSETLSLTCTVSGASISSSHYYWGWIRQPPGKGPEWIGSMYYSGRTYYNPALKSRVT
ISPDKSKNQFFLKLTSVTAADTAVYYCAREGPTHYYDNSGPIPSDEYFQHWGQGTLVTVS

L9-MG secreted form (MG67) (6aa - 114aa) 109aa

SYELTQPPSVSVSPGQTARITCSGDALPKQYTYWYQQKAGQAPVLVIYKDTERPSGIPERFSGTSSGTTV
TLTISGVQAEDEADYYCQSADSSGSYVFFGGGTKVTVLS

*Figure 1B*

L5-MG E52D pPNL6 fusion protein 250aa

MQLLRCFSIFSVIASVLAQELTTICEQIPSPTLESTPYSLSTTTILANGKAMQGVFEYYKSVTFVSNCGS

HPSTTSKGSPINTQYVFKDNSSTIEGRYPYDVPDYALQASGGGGSGGGGSGGGGSASQAVVTQEPSVTVS

PGGTVILTCGSSTGAVTSGHYANWFQQKPGQAPRALIFDTDKKYPWTPGRFSGSLLGVKAALTISDAQPE

DEAEYYCLLSDVDGYLFGGGTQLTVLSGILEQKLISEEDL

*Figure 2A*

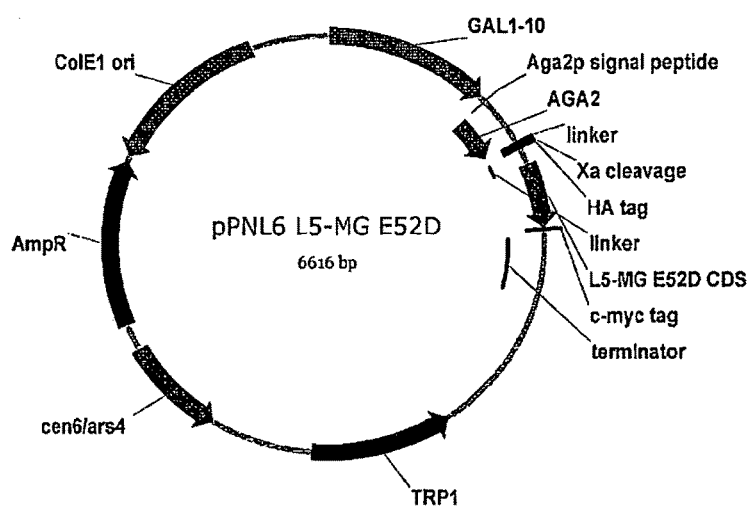

*Figure 2B*

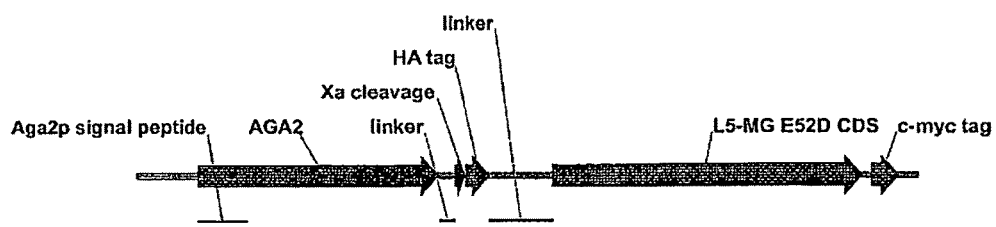

L5-MG E52D fusion protein expressed in pPNL6

*Figure 2C*

|  | AGA2 |
| --- | --- |
|  | M Q L L R C F S I F S V I A S V L A Q |
| +3 | AAAAATCCC GGATCGAATT CTACTTCATA CATTTCAAT TAAGATGCAG TTACTTCGGT GTTTTCAG ATTGCTTCGT ATTGCTCTGT TTTAGCACA |
| 805 | Aga2p signal peptide |

|  | AGA2 |
| --- | --- |
|  | Q E L T T I C E Q I P S P T L E S T P Y S L S T T T I L A N G K A M |
| +3 | GGAACTCACA ACTATATGCG AGCAAATCCC CTCCGTACTT TAAGAATCGA ACTCCGTACT TTGTCACCC ACTACTATTT TGGCCAACGG GAAGGCAATG |
| 905 | AGA2 |

|  | Q G V F E Y Y K S V T F V S N C G S H P S T T S K G S P I N T Q Y V |
| --- | --- |
| +3 | CAAGGTGTTT TTGAATATTA CAAATCAGTA ACGTTTGTCA AGTAATTGCG GTAATCATCC TTCTCACCCC TCAACACTA GCAAAGCCAG CCCAATAAC ACACAGTATG |
| 1005 | HA tag |

|  | AGA2 | Xa cleavage |
| --- | --- | --- |
|  | -V F K D N S S T I E G R Y P Y D V P D Y A L Q A S G G G G S G G G G |
| +3 | TTTTTAAGGA CAATAGCTCG ACGATTGAAG GTAGATACCC GTATGATGTT CCAGATTAGG CTCTGCAGGC TAGTGGTGGT GGTGGTTCTG GTGGTGGTGG |
| +1 | linker | linker |

*Fig 2D-1*

```
                                    L5-MG E52D CDS
       -G S G G G G G S A S Q A V V V T Q E P S V T V S P G G T V I L T C G S S
    +3
    +1
  1205     TTCTGGTTGT GGTGGTTCTG CTAGCCAGGC TGTGGTGACT CAGGAGCCGT CAGTGACTGT GTCCCCAGGA GGAACAGTCA TCTCACTTG TGGCTCCAGC
                                    linker
                                    L5-MG E52D CDS
       T G A V T S G H Y A N W F Q Q K P G Q A P R A L I F D T D K K Y P V
    +3
    +1
  1305     ACTGGAGCTG TGACCAGTGG TCATTATGCC AACTGGTTCC AGCAGAAACC CGGACAAGCC CCTAGGGCAC TTATATTTGA CACCGACAAG AAATATCCCT
                                    L5-MG E52D CDS
       -W T P G R F S G S S L L G V K A A L T I S D A Q P E D E A E Y Y C L L
    +3
    +1
  1405     GGACCCCTGG GCGTTTCTCA GGCTCCAGTC TTGGGGTCAA GGCTGCCCTG ACCATCTCGG ACGCTCAGCC TGAAGATGAG GCTGAGTATT ACTGTTTGCT
                                                                                         c-myc tag
                                    L5-MG E52D CDS
       -L S D V D G Y L F G G G T Q L T V V L S G I L E Q K L I S E E D L
    +3
  1505     CTCTGACGTT GAGGGTTATC TGTTCGGAGG AGGCACCCAG CTGACCGTCC TCTCCGGAAT TCTAGAACAA AAGCTTATTT CTGAAGAAGA CTTGTAATAG
  1605     CTCGGCCGCC GCA
```

Fig 2D-2

GTCTGCAAGCAGACCTGGCAGCATTGGGCTGGCCGCCCCCAGGGCCTCCTCTTCATGCCCAGTGAATGACTCACCTTGG
CACAGACACAATGTTCGGGGTGGGCACAGTGCCTGCTTCCCGCCGCACCCCAGCCCCCCTCAAATGCCTTCCGAGAAGCC
CATTGAGTAGGGGGCTTGCATTGCACCCCAGCCTGACAGCCTGGCATCTTGGGATAAAAGCAGCACAGCCCCCTAGGGGC
TGCCCTTGCTGTGTGGCGCCACCGGCGGTGGAGAACAAGGCTCTATTCAGCCTGTGCCCAGGAAAGGGGATCAGGGGATG
CCCAGGCATGGACAGTGGGTGGCAGGGGGGAGAGGAGGGCTGTCTGCTTCCCAGAAGTCCAAGGACACAAATGGGTGAG
GGGACTGGGCAGGGTTCTGACCCTGTGGGACCAGAGTGGAGGGCGTAGATGGACCTGAAGTCTCCAGGGACAACAGGGCC
CAGGTCTCAGGCTCCTAGTTGGGCCCAGTGGCTCCAGCGTTTCCAAACCCATCCATCCCCAGAGGTTCTTCCCATCTCTC
CAGGCTGATGTGTGGGAACTCGAGGAAATAAATCTCCAGTGGGAGACGGAGGGGTGGCCAGGGAAACGGGGCGCTGCAGG
AATAAAGACGAGCCAGCACAGCCAGCTCATGCGTAACGGCTTTGTGGAGCTGTCAAGGCCTGGTCTCTGGGAGAGAGGCA
CAGGGAGGCCAGACAAGGAAGGGGTGACCTGGAGGGACAGATCCAGGGGCTAAAGTCCTGATAAGGCAAGAGAGTGCCGG
CCCCCTCTTGCCCTATCAGGACCTCCACTGCCACATAGAGGCCATGATTGACCCTTAGACAAAGGGCTGGTGTCCAATCC
CAGCCCCCAGCCCAGAACTCCAGGGAATGAATGGGCAGAGAGCAGGAATGTGGGACATCTGTGTTCAAGGGAAGGACTC
CAGGAGTCTGCTGGGAATGAGGCCTAGTAGGAAATGAGGTGGCCCTTGAGGGTACAGAACAGGTTCATTCTTCGCCAAAT
TCCCAGCACCTTGCAGGCACTTACAGCTGAGTGAGATAATGCCTGGGTTATGAAATCAAAAAGTTGGAAAGCAGGTCAGA
GGTCATCTGGTACAGCCCTTCCTTCCCTTTTTTTTTTTTTTTTTTTGTGAGACAAGGTCTCTCTCTGTTGCCCAGGC
TGGAGTGGCGCAAACACAGCTCACTGCAGCCTCAACCTACTGGGCTCAAGCAATCCTCCAGCCTCAGCCTCCCAAAGTGC
TGGGATTACAAGCATGAGCCACCCCACTCAGCCCTTTCCTTCCTTTTTAATTGATGCATAATAATTGTAAGTATTCATCA
TGGTCCAACCAACCCTTTCTTGACCCACCTTCCTAGAGAGAGGGTCCTCTTGATTCAGCGGTCAGGGCCCCAGACCCATG
GTCTGGCTCCAGGTACCACCTGCCTCATGCAGGAGTTGGCGTGCCCAGGAAGCTCTGCCTCTGGGCACAGTGACCTCAGT
GGGGTGAGGGGAGCTCTCCCCATAGCTGGGCTGCGGCCCAACCCCACCCCCTCAGGCTATGCCAGGGGGTGTTGCCAGGG
GCACCCGGGCATCGCCAGTCTAGCCCACTCCTTCATAAAGCCCTCGCATCCCAGGAGCGAGCAGAGCCAGAGCAT

*Fig. 3*

AGTATCTGCAGAGGGCCCTGCGTATGAGTGCAAGTGGGTTTTAGGACCAGGATGAGGCG
GGGTGGGGGTGCCTACCTGACGACCGACCCCGACCCACTGGACAAGCACCCAACCCCCATTCCCCAAATTGCGC
ATCCCCTATCAGAGAGGGGGAGGGGAAACAGGATGCGGCGAGGCGCGTGCGCACTGCCAGCTTCAGCACCGCGG
ACAGTGCCTTCGCCCCCGCCTGGCGGCGCGCGCCACCGCCGCCTCAGCACTGAAGGCGCGCTGACGTCACTCGC
CGGTCCCCCGCAAACTCCCCTTCCCGGCCACCTTGGTCGCGTCCGCGCCGCCGCCGGCCCAGCCGGACCGCACC
ACGCGAGGCGCGAGATAGGGGGGCACGGGCGCGACCATCTGCGCTGCGGCGCCGGCGACTCAGCGCTGCCTCAG
TCTGCGGTGGGCAGCGGAGGAGTCGTGTCGTGCCTGAGAGCGCAGCTGTGCTCCTGGGCACCGCGCAGTCCGCC
CCCGCGGCTCCTGGCCAGACCACCCCTAGGACCCCCTGCCCCAAGTCGCAGCC

*Fig. 4*

| Carbon Number | Carbon | Proton |
|---|---|---|
| 1,2,14,15 | 39.42 | 3.25 (14H,s) |
| 3,13 | 156.9 | |
| 4,8,12,16 | 113.0 | 6.98 (4H,d) |
| 5,7,11,17 | 140.4 | 7.36 (4H,d) |
| 6,10 | 126.8 | |
| 9 | 177.9 | |
| 18 | 131.8 | |
| 19,23 | 114.7 | 7.14 (2H,d) |
| 20,22 | 137.4 | 7.31 (2H,d) |
| 21 | 164.2 | |
| 24 | 66.0 | 4.16 (2H,t) |
| 25 | 28.6 | 2.0 (2H,m) |
| 26 | 35.9 | 3.37 (2H,m) |
| 27 | 174.5 | |
| 28 | 35.3 | 2.23 (2H,t) |
| 29 | 25.0 | 1.70 (2H,m) |
| 30 | 25.8 | 1.45 (2H,m) |
| 31 | 26.7 | 1.81 (2H,m) |
| 32 | 43.8 | 4.08 (2H,t) |
| 33 | 141.8 | |
| 34,54 | 110.6/111.6 | 7.43 (1H,d), 7.27 (1H,d) |
| 35,53 | 127.3 | 7.94 (1H,dd), 7.84 (1H,dd) |
| 36,52 | 144.9 / 142.5 | |
| 37,51 | 120.2 / 120.5 | 7.97 (1Hd), 7.88 (1H,d) |
| 38,50 | 142.3/ 140.3 | |
| 39 | 49.2 | |
| 40,41 | 26.8 | 1.72 (6H, s) |
| 42 | 175.0 | |
| 43 | 102.8 | |
| 44 | 150.8 | |
| 45 | 102.8 | |
| 46 | 179.8 | |
| 47 | 50.1 | |
| 48,49 | 24.8 | 1.53 (6H,br s) |

*Fig. 9D*

QVQLVESEAEVKKPGSSVKVSCKASGGTFSSYAISWVRQAPGQGLEWMGGTIPIFGTAD
YAQEFQGRVTITTDESTSTAYMELSGLRSEDTAVYYCVLLGTTMVTGHYFDYWGQGTL
VTVSSGILGSGGGGSGGGGSGGGGSNFMLTQPPSASGTPGQSVTISCSGSGSNIGNNKVN
WYQQLPGTAPKLLIYSNNQRPSGVPDRFSGSKSGTSASLAISGLQSEDEADYYCAAWDD
GLSGYVFGTGTKLTVLSGIGRRGRDPRLQVDEQKLISEEDLNAMGQPGNGSAFLLAPNG
SHAPDHDVTQQRDEVWVVGMGIVMSLIVLAIVFGNVLVITAIAKFERLQTVTNYFITSLA
CADLVMGLAVVPFGAAHILMKMWTFGNFWCEFWTSIDVLCVTASIETLCVIAVDRYFAI
TSPFKYQSLLTKNKARVIILMVWIVSGLTSFLPIQMHWYRATHQEAINCYANETCCDFFT
NQAYVIASSIVSFYVPLVIMVFVYSRVFQEAKRQLQKIDKSEGRFHVQNLSQVEQDGRT
GHGLRRSSKFCLKEHKALKTLGIIMGTFTLCWLPFFIVNIVHVIQDNLIRKEVYILLNWIG
YVNSGFNPLIYCRSPDFRIAFQELLCLRRSSLKAYGNGYSSNGNTGEQSGYHVEQEKEN
KLLCEDLPGTEDFVGHQGTVPSDNIDSQGRNCSTNDSLL

*Fig. 13A*

```
tgtatttagaaaaataaacaaataggggttccgcgcacatttccccgaaaagtgccacctgcag
cctgaatatgggccaaacaggatatctgtggtaagcagttcctgccccggctcagggccaagaa
cagatggaacagctgaatatgggccaaacaggatatctgtggtaagcagttcctgccccggctc
agggccaagaacagatggtcccagatgcggtccagccctcagcagtttctagagaaccatcag
atgttccagggtgccccaaggacctgaaatgacctgtgccttatttgaactaaccaatcagt
tcgcttctcgcttctgttcgcgcgcttctgctccccgagctcaataaaagagcccacaacccct
cactcggggcgccagtcctccgattgactgagtcgcccgggtacccgtgtatccaataaaccct
cttgcagttgcatccgacttgtggtctcgctgttccttggggagggtctcctctgagtgattgac
tacccgtcagcgggggtctttcatttggggctcgtccgggatcgggagaccctgcccaggga
ccaccgacccaccaccgggaggtaagctggccagcaacttatctgtgtctgtccgattgtctag
tgtctatgactgattttatgcgcctgcgtcggtactagttagctaactagctctgtatctggcg
gacccgtggtggaactgacgagttctgaacacccggccgcaaccctgggagacgtcccagggac
tttgggggccgttttgtggcccgacctgaggaagggagtcgatgtggaatccgaccccgtcag
gatatgtggttctggtaggagacgagaacctaaaacagttcccgcctccgtctgaattttgct
ttcggtttggaaccgaagccgcgcgtcttgtctgctgcagcatcgttctgtgttgtctctgtct
gactgtgtttctgtatttgtctgaaaattagggccagactgttaccactcccttaagtttgacc
ttagatcactggaaagatgtcgagcggctcgctcacaaccagtcggtagatgtcaagaagagac
gttgggttaccttctgctctgcagaatggccaacctttaacgtcggatggccgcgagacggcac
ctttaaccgagacctcatcacccaggttaagatcaaggtcttttcacctggcccgcatggacac
ccagaccaggtccctacatcgtgacctgggaagccttggcttttgaccccctccctgggtca
agccctttgtacaccctaagcctccgcctcctcttcttccatccgcgccgtctctccccttga
acctcctctttcgacccgcctcaatcctccctttatccagccctcactcctctctaggcgcc
ggccggatccactagtaacggccgccagtgtgctggaattcggcttggggatatccaccatgga
gacagacacactcctgctatgggtactgctgctctgggttccaggttccactggtgactatcca
tatgatgttccagattatgctggggcccagccggcctacccatacgacgttccagactacgctc
tgcaggctagtggtggtggtggttctggtggtggtggttctggtggtggttctgctagcca
ggtgcagctggtggaatctgaggctgaggtgaagaagcctgggtcctcggtgaaggtctcctgc
aaggcctctggaggcaccttcagcagctatgctatcagctgggtgcggcaggcccctggacaag
ggcttgagtggatgggagggaccatccctatctttggtacagcagactacgcacaggagttcca
gggcagagtcacgattaccacggacgaatccacgagcacagcctacatggagctgagcggcctg
agatctgaggacacggccgtgtattactgtgttttgttgggtacaactatggttacgggacact
actttgactactggggccagggaaccctggtcaccgtctcctcaggaattctaggatccggtgg
cggtggcagcggcggtggtggttccggaggcggcggttctaattttatgctgactcagcccccc
tcagcgtctgggaccccgggcagagcgtcaccatctcttgttctggaagcggctcgaacatcg
gaaacaataaagtaaactggtaccagcagctcccaggaacggcccccaaactcctcatctatag
taataatcagcggccctcaggggtccctgaccgattctctggctccaagtctggcacctcagcc
tccctggccatcagtgggctccagtctgaggatgaggctgattattactgtgcagcatgggatg
acggtctgagtggttatgtcttcggaactgggaccaagctcaccgtcctatccggaattggccg
cagggggccgggatccgcggctgcaggtcgacgaacaaaaactcatctcagaagaggatctgaat
```

*Fig. 13B-1*

```
gctatggggcaacccgggaacggcagcgccttcttgctggcacccaatggaagccatgcgccgg
accacgacgtcacgcagcaaagggacgaggtgtgggtggtgggcatgggcatcgtcatgtctct
catcgtcctggccatcgtgtttggcaatgtgctggtcatcacagccattgccaagttcgagcgt
ctgcagacggtcaccaactacttcatcacttcactggcctgtgctgatctggtcatgggcctag
cagtggtgccctttggggccgcccatattcttatgaaaatgtggacttttggcaacttctggtg
cgagttttggacttccattgatgtgctgtgcgtcacggccagcattgagacctgtgcgtgatc
gcagtggatcgctactttgccattacttcacctttcaagtaccagagcctgctgaccaagaata
aggcccgggtgatcattctgatggtgtggattgtgtcaggccttacctccttcttgcccattca
gatgcactggtacagggccacccaccaggaagccatcaactgctatgccaatgagacctgctgt
gacttcttcacgaaccaagcctatgtcattgcctcttccatcgtgtccttctacgttccctgg
tgatcatggtcttcgtctactccagggtctttcaggaggccaaaaggcagctccagaagattga
caaatctgagggccgcttccatgtccagaaccttagccaggtggagcaggatgggcggacgggg
catggactccgcagatcttccaagttctgcttgaaggagcacaaagccctcaagacgttaggca
tcatcatgggcactttcaccctctgctggctgcccttcttcatcgttaacattgtgcatgtgat
ccaggataacctcatccgtaaggaagtttacatcctcctaaattggataggctatgtcaattct
ggtttcaatccccttatctactgccggagcccagatttcaggattgccttccaggagcttctgt
gcctgcgcaggtcttctttgaaggcctatgggaatggctactccagcaacggcaacacagggga
gcagagtggatatcacgtggaacaggagaaagaaaataaactgctgtgtgaagacctcccaggc
acggaagactttgtgggccatcaaggtactgtgcctagcgataacattgattcacaagggagga
attgtagtacaaatgactcactgctgtagaatgctgtgggccaggacacgcaggaggtcatcgt
ggtgccacactccttgccctttaaggtggtggtgatctcagccatcctggccctggtggtgctc
accatcatctcccttatcatcctcatcatgctttggcagaagaagccacgtccacagcctggt
tagctcactcattaggcaccccaggctttacacttactgggaaaaccctggcgttacccaantt
aatcgccttgcagcacatccccctttcgccagctggcgtaatagcgaagaggcccgcaccgatc
gcccttcccaacagttgcgcagcctgaatggcgaatggcgctttgcctggtttccggcaccaga
agcggtgccggaaagctggctggagtgcgatcttcctgaggccgatactgtcgtcgtcccctca
aactggcgttagccagcaggtggtaggcggccgctcgaccctgtggaatgtgtgtcagttaggg
tgtggaaagtccccaggctccccagcaggcagaagtatgcaaagcatgcatctcaattagtcag
caaccaggtgtggaaagtccccaggctccccagcaggcagaagtatgcaaagcatgcatctcaa
ttagtcagcaaccatagtcccgcccctaactccgcccatcccgcccctaactccgcccagttcc
gcccattctccgcccatggctgactaattttttttatttatgcagaggccgaggccgcggcct
ctgagctattccagaagtagtgaggaggcttttttggaggcctaggcttttgcaaaaagcttac
catgaccgagtacaagcccacggtgcgcctcgccacccgcgacgacgtccccagggccgtacgc
accctcgccgccgcgttcgccgactacccgccacgcgccacaccgtcgatccggaccgccaca
tcgagcgggtcaccgagctgcaagaactcttcctcacgcgcgtcgggctcgacatcggcaaggt
gtgggtcgcggacgacggcgccgcggtggcggtctggaccacgccggagagcgtcgaagcgggg
gcggtgttcgccgagatcggcccgcgcatggccgagttgagcggttcccggctggccgcgcagc
aacagatggaaggcctcctggcgccgcaccggcccaaggagcccgcgtggttcctggccaccgt
cggcgtctcgcccgaccaccagggcaagggtctgggcagcgccgtcgtgctccccggagtggag
```

*Fig. 13B-2*

```
gcggccgagcgcgccggggtgcccgccttcctggagacctccgcgccccgcaacctcccttct
acgagcggctcggcttcaccgtcaccgccgacgtcgagtgcccgaaggaccgcgcgacctggtg
catgacccgcaagcccggtgcctgacgcccgccccacgacccgcagcgcccgaccgaaaggagc
gcacgaccccatgcatcgataaaataaaagatttatttagtctccagaaaaaggggggaatga
agacccacctgtaggtttggcaagctagcttaagtaacgccattttgcaaggcatggaaaaa
tacataactgagaatagagaagttcagatcaaggtcaggaacagatggaacagctgaatatggg
ccaaacaggatatctgtggtaagcagttcctgccccggctcagggccaagaacagatggaacag
ctgaatatgggccaaacaggatatctgtggtaagcagttcctgccccggctcagggccaagaac
agatggtccccagatgcggtccagccctcagcagtttctagagaaccatcagatgtttccaggg
tgccccaaggacctgaaatgaccctgtgccttatttgaactaaccaatcagttcgcttctcgct
tctgttcgcgcgcttctgctccccgagctcaataaaagagcccacaacccctcactcggggcgc
cagtcctccgattgactgagtcgcccgggtaccgtgtatccaataaaccctcttgcagttgca
tccgacttgtggtctcgctgttccttgggagggtctcctctgagtgattgactacccgtcagcg
ggggtctttcatttccgacttgtggtctcgctgccttgggagggtctcctctgagtgattgact
acccgtcagcgggggtcttcacatgcagcatgtatcaaaattaatttggtttttttcttaagt
atttacattaaatggccatagttgcattaatgaatcggccaacgcgcggggagaggcggtttgc
gtattggcgctcttccgcttcctcgctcactgactcgctgcgctcggtcgttcggctgcggcga
gcggtatcagctcactcaaaggcggtaatacggttatccacagaatcaggggataacgcaggaa
agaacatgtgagcaaaaggccagcaaaaggccaggaaccgtaaaaaggccgcgttgctggcgtt
tttccataggctccgcccccctgacgagcatcacaaaaatcgacgctcaagtcagaggtggcga
aacccgacaggactataaagataccaggcgtttccccctggaagctccctcgtgcgctctcctg
ttccgaccctgccgcttaccggatacctgtccgcctttctcccttcgggaagcgtggcgctttc
tcatagctcacgctgtaggtatctcagttcggtgtaggtcgttcgctccaagctgggctgtgtg
cacgaaccccccgttcagcccgaccgctgcgccttatccggtaactatcgtcttgagtccaacc
cggtaagacacgacttatcgccactggcagcagccactggtaacaggattagcagagcgaggta
tgtaggcggtgctacagagttcttgaagtggtggcctaactacggctacactagaaggacagta
tttggtatctgcgctctgctgaagccagttaccttcggaaaaagagttggtagctcttgatccg
gcaaacaaaccaccgctggtagcggtggttttttgtttgcaagcagcagattacgcgcagaaa
aaaaggatctcaagaagatcctttgatcttttctacggggtctgacgctcagtggaacgaaaac
tcacgttaagggattttggtcatgagattatcaaaaaggatcttcacctagatccttttaaatt
aaaaatgaagtttgcggccgcaaatcaatctaaagtatatatgagtaaacttggtctgacagtt
accaatgcttaatcagtgaggcacctatctcagcgatctgtctatttcgttcatccatagttgc
ctgactccccgtcgtgtagataactacgatacgggagggcttaccatctggccccagtgctgca
atgataccgcgagacccacgctcaccggctccagatttatcagcaataaaccagccagccggaa
gggccgagcgcagaagtggtcctgcaactttatccgcctccatccagtctattaattgttgccg
ggaagctagagtaagtagttcgccagttaatagtttgcgcaacgttgttgccattgctacaggc
atcgtggtgtcacgctcgtcgtttggtatggcttcattcagctccggttcccaacgatcaaggc
gagttacatgatccccatgttgtgcaaaaaagcggttagctccttcggtcctccgatcgttgt
cagaagtaagttggccgcagtgttatcactcatggttatggcagcactgcataattctcttact
```

*Fig. 13B-3*

```
gtcatgccatccgtaagatgcttttctgtgactggtgagtactcaaccaagtcattctgagaat
agtgtatgcggcgaccgagttgctcttgcccggcgtcaacacgggataataccgcgccacatag
cagaactttaaaagtgctcatcattggaaaacgttcttcggggcgaaaactctcaaggatctta
ccgctgttgagatccagttcgatgtaacccactcgtgcacccaactgatcttcagcatctttta
ctttcaccagcgtttctgggtgagcaaaaacaggaaggcaaaatgccgcaaaaagggaataag
ggcgacacggaaatgttgaatactcatactcttccttttttcaatattattgaagcatttatcag
ggttattgtctcatgagcggatacatatttgaa
```

*Fig. 13B-4*

TARGETED PROBES OF CELLULAR PHYSIOLOGY

CROSS REFERENCE TO RELATED APPLICATIONS

This application is a National Stage of International Patent Application No. PCT/US2011/037933, filed May 25, 2011, which claims the benefit of U.S. Provisional Patent Application No. 61/396,272, filed May 25, 2010, each of which is herein incorporated by reference in its entirety.

STATEMENT REGARDING FEDERAL FUNDING

This invention was made with government support under the National Institutes of Health No. 5U54-RR022241 and R01-NIH 1R01GM086237. The government has certain rights in this invention.

The Sequence Listing associated with this application is filed in electronic format via EFS-Web and is hereby incorporated by reference into the specification in its entirety. The name of the text file containing the Sequence Listing is 6526_123335_ST25.txt. The size of the text file is 32,576 Bytes, and the text file was created on Nov. 7, 2012.

Provided are environment-sensitive compounds and biosensor systems as well as methods of making and using the compounds and biosensor systems.

Environment-sensitive compounds, such as dyes, are compounds that are capable of producing a different signal depending on environmental conditions. Other environment-sensitive compounds detect differences in environmental factors, such as pH, membrane potential, ion concentration (e.g., $Ca^{++}$ and $Zn^{++}$), and small molecule concentration. This technology holds enormous analytical potential. Nevertheless, there are substantial limitations. For example, background signal often results in significant imaging difficulties. Quantification also is difficult due to the inability to differentiate signal from the compound that is bound and signal that arises from the environment-sensitive compound or moiety in the compound.

As an example, voltage-sensitive probes are useful for mapping electrical connections and activity in neurological tissues. Recent advances have provided high speed cameras that can resolve millisecond action potentials from cells in a stained region and new two-photon imaging methods can resolve optical voltage signals from deeper in tissues. However, there are two major barriers that must still be overcome to realize the power of this technology. One major problem is that currently available voltage sensitive probes, which diffuse to all cells in the brain tissue, result in optical signals from all excitable cells that have been stained. In an intact brain, such complete network activity does not allow selective monitoring of cell type-specific networks that drive distinct behaviors. The second problem is that high background fluorescence from stained tissue provides additional loss of detection sensitivity. If there were a way to target both the fluorescence signal and the voltage sensing probe itself selectively to cells of interest, the field of optical neurobiology would be revolutionized. But currently no robust probe technology enables genetically targeted voltage sensing.

SUMMARY

Described herein are compositions and methods that overcome the limitations of prior environmental sensing techniques. Certain beneficial qualities are configured into the biosensor compositions described herein. The biosensors comprise a FRET (Förster resonance energy transfer or fluorescence resonance energy transfer) pair linked by a linker. A first member of the FRET pair is an environment-sensitive donor group and the second member is an activatable acceptor fluorogen. The environment-sensitive donor responds to light (electro-magnetic radiation not necessarily in the human visual spectrum) of a suitable excitation spectrum by transferring resonance energy to the activatable acceptor fluorogen, causing the activatable acceptor fluorogen to fluoresce. The activatable acceptor fluorogen produces a fluorescence signal increase of >100-fold when it interacts non-covalently with the activator as compared to when no activator is present. An example an activator is an FAP (fluorogen activator peptide). The environment-sensitive donor transfers different amounts of excitation energy to the activatable acceptor fluorogen when it interacts with an analyte as compared to when no analyte is present. The analyte can be molecular or environmental, for example and without limitation: calcium, zinc, sodium, potassium, hydrogen, pH (e.g., hydronium), voltage, hydrophobicity/hydrophilicity, small molecule drugs, Reactive oxygen species, singlet oxygen, peroxide, superoxide, hydroxyl radical, nitric oxide, and second messengers, e.g inositol triphosphate, diphosphates, cAMP, and cGMP, The activator can be targeted for expression in vitro, in vivo, in situ, etc. in a specific organism, cell-type, tissue, etc. or may be bound to a surface, e.g., in an array or bead. In one Example, an FAP is expressed in a tissue-specific manner to be expressed on a surface of a specific cell-type. The biosensor composition binds specifically to the FAP, therefore only binding to the target cells. In another Example, the activator is linked to, e.g., by a protein bond, e.g., as a contiguous protein sequence, to a selectivity component, such as an antibody, antibody fragment, scFv or other binding pair members.

When the biosensor is exposed to light within (including overlapping with) the excitation spectrum of the activatable acceptor fluorogen and not overlapping the excitation spectrum of the environment-sensitive donor, activator-bound activatable acceptor fluorogen will fluoresce at least 100-fold brighter than unbound activatable acceptor fluorogen, thereby reducing background fluorescence from unbound biosensor. Further, quantification of fluorescence resulting from exposure to light within the excitation spectrum of the activatable acceptor fluorogen and not overlapping the excitation spectrum of the environment-sensitive donor yields an intrinsic control to any assay for binding of the biosensor to its target.

When the biosensor is exposed to light within the excitation spectrum of the environment-sensitive donor and not overlapping the excitation spectrum of the activatable acceptor fluorogen, the environment-sensitive donor will transfer differing amounts of energy to the activatable acceptor fluorogen so that the activatable acceptor fluorogen will fluoresce at differing intensities depending on the amount of an analyte the environment-sensitive donor is sensitive to. This permits quantification of the amount of or determining the presence of analyte present in the area surrounding the biosensor.

According to one embodiment, a biosensor is provided. The biosensor comprises an activatable acceptor fluorogen linked by a linker to an environment-sensitive donor that interacts with an analyte. The activatable acceptor fluorogen produces a fluorescence signal increase of at least 100-fold when it interacts non-covalently with an activator of the activatable acceptor fluorogen as compared to when no activator is present. The environment-sensitive donor, though not necessarily fluorescent without an acceptor, transfers excitation energy to the activatable acceptor fluorogen such that, when activated, the activatable acceptor fluorogen produces a detectable fluorescent signal when the environment-sensitive donor is excited and the environment-sensitive donor transfers different amounts of excitation energy to the activatable acceptor fluorogen when it interacts with the analyte as compared to when no analyte is present. The activator may be a polypeptide, such as a fluorogen activator peptide. In a typical biosensor, the activatable acceptor fluorogen and the environment-sensitive donor are covalently linked by a linker (linking group). According to one embodiment, the environment-sensitive donor is attached to the activatable acceptor fluorogen by a molecular linker and the activatable acceptor fluorogen and the environment-sensitive donor are close enough for resonance energy transfer of excited state energy of the sensitive donor to be transferred to the activatable acceptor fluorogen with at least 50% efficiency.

In one embodiment, the environment-sensitive donor detects an ion binding event leading to a change in the fluorescence intensity of the activatable acceptor fluorogen when it is bound to its activator. The ion is a hydrogen ion, calcium ion, potassium ion, sodium ion, or zinc ion in select embodiments. In one embodiment, the environment-sensitive donor is a rhodamine, such as Rhod-2, or an analog thereof (such as described below). In another embodiment, the environment-sensitive donor is sensitive to an electrical potential difference across a cellular membrane, examples of which include Merocyanine XVII, Oxonol RH155, styryl Di4-ANEPPS, ANNINE-6 and Oxonol XXV. In another embodiment, the environment-sensitive donor is a polarity-sensitive dye, examples of which include: indole, CASCADE YELLOW™, prodan, Dansyl, Dapoxyl, NBD, PyMPO, Pyrene and diethylaminocoumarin.

As described above, the activatable acceptor fluorogen exhibits enhanced fluorescence when bound by (interacts with) the activator. An example of such a fluorogen is a non-rigidized aromatic system, including monomethine dyes, cyanine dyes, malachite green malachite green, indocyanine green, acetylenic malachite green, dimethylindole red, a triarylmethine dye; a diarylmethine dye; and a monomethine dye. For example, the activatable acceptor fluorogen is

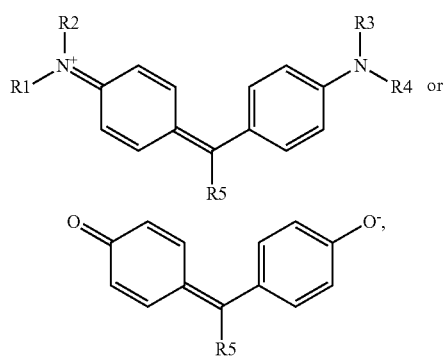

in which R1-R4 are —H, —CH$_3$, (CH$_2$)$_n$-T, and substituted aryl, and R5 is a substituted aryl chosen from:

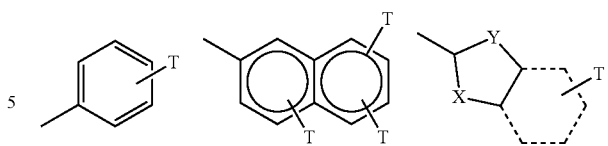

where, for R1-R5, n=0-6 and T is selected from —H, —OH, COO—, SO$_3^-$, —PO$_4^-$, amide, halogen, substituted single or multiple aryl, ether, polyether, PEG$_{1-30}$, heterocycles containing N, S or O atoms, substituted acetylenic groups, cyano, and carbohydrate groups and optionally comprises a linker for attachment to the environment-sensitive donor.

In one example, the activatable acceptor fluorogen is:

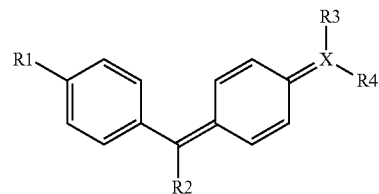

where R1 is aromatic, heteroaromatic, hydroxyl, amino, N-alkyl, N-alkanolyl (alcohol, e.g., N-hydroxyethyl), R2 is H, cyano, aromatic, heteroaromatic, acetylenic, alkyl, X is N, O, or S and R3 and R4 is absent or is alkyl, aryl, or hydroxyethyl. In one embodiment, R1 is di-C$_{1-3}$ alkylamino, R2 is a substituted phenylacetylene, phenyl, —N-alkyl-substituted phenyl, —O(CH$_2$)$_n$R5 substituted phenyl where n is 1-5 and R5 is carboxyl or amino, X is N, and R3 and R4 are independently C$_{1-3}$ alkyl, alkoxyl, alkanolyl, phenyl, C$_{1-3}$ alkyl-substituted phenyl. In another embodiment, R2 is —N—(CH$_3$)$_2$; —N—(CH$_3$)((CH$_2$)$_n$O(CH$_2$)$_m$COOH) in which n and m are independently 1, 2, 3 or 4. In a further embodiment R1 is —N(CH$_3$)$_2$, R2 is one of —O(CH$_2$)$_3$R5-substituted phenyl and

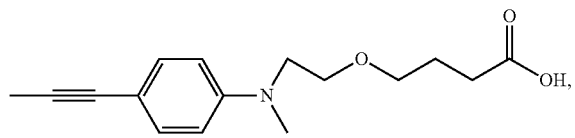

or R3 and R4 are CH$_3$.

In other embodiments, the activatable acceptor fluorogen is one or more of:

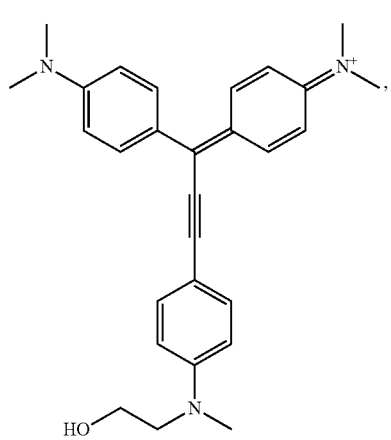

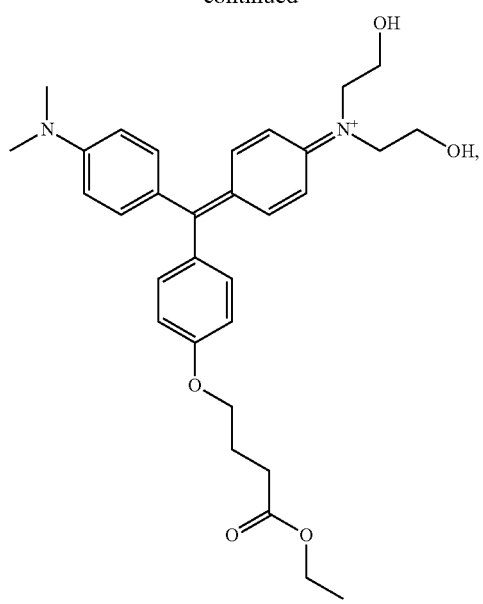
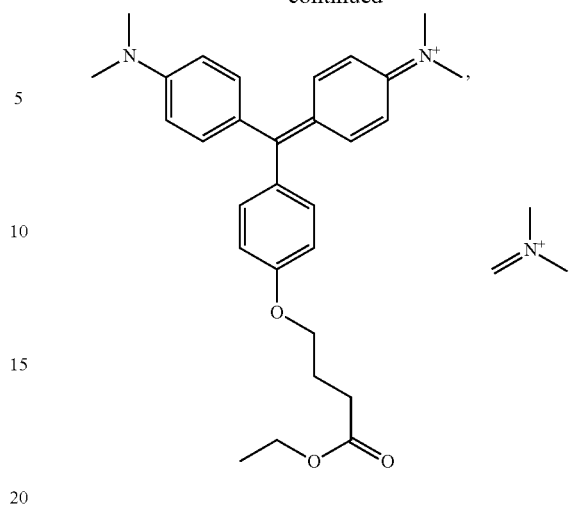
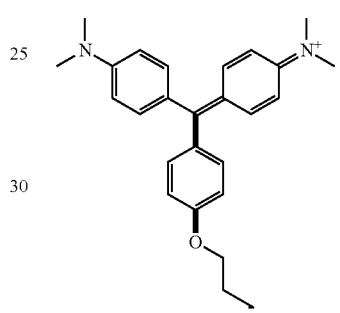
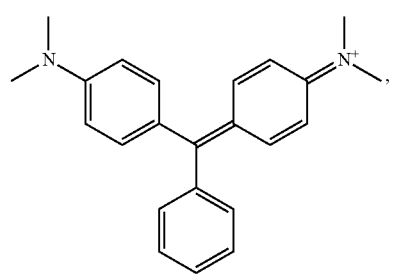
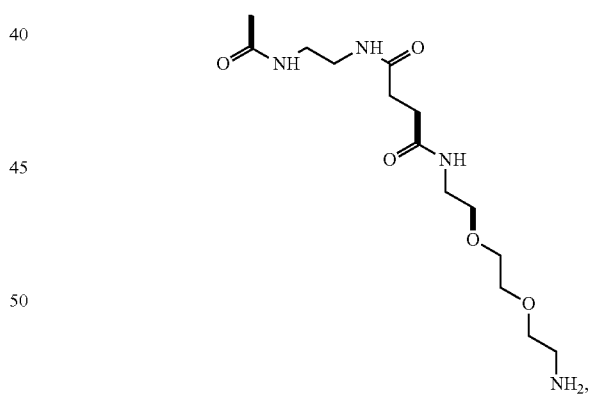
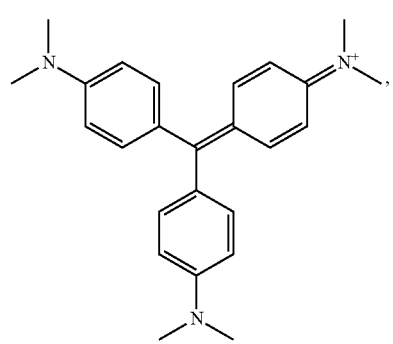
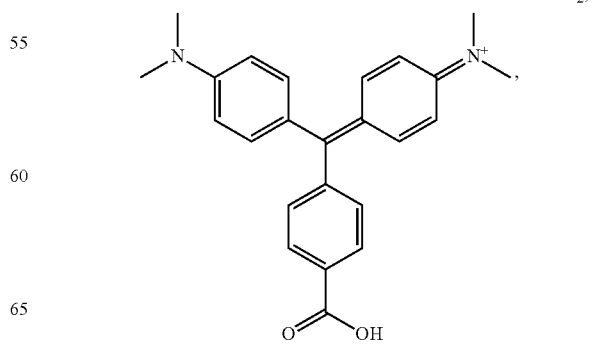

7
-continued
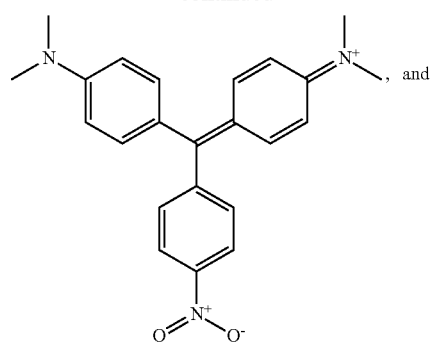
, and
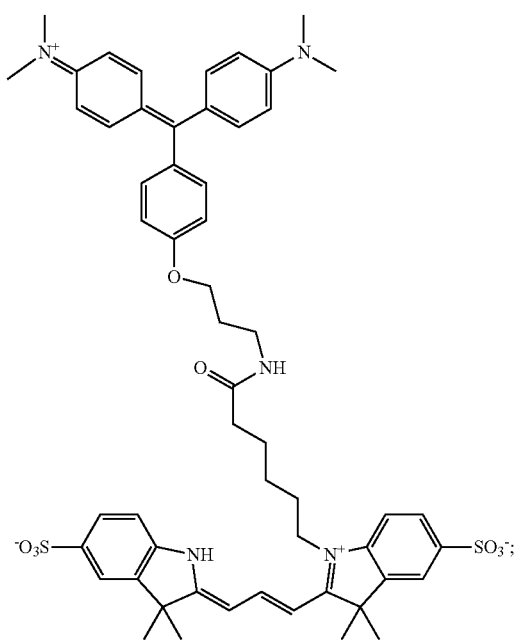
8
-continued
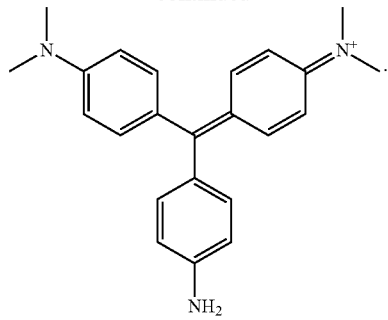
Specific examples of biosensors include:
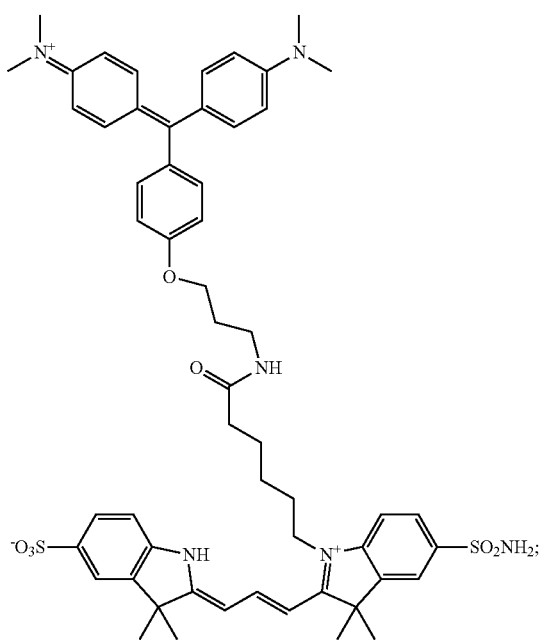
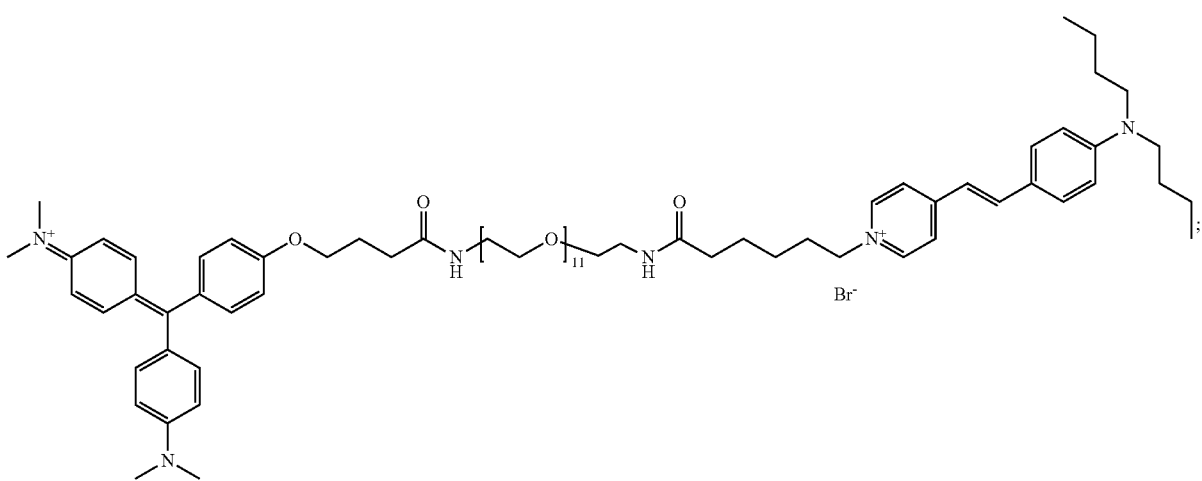

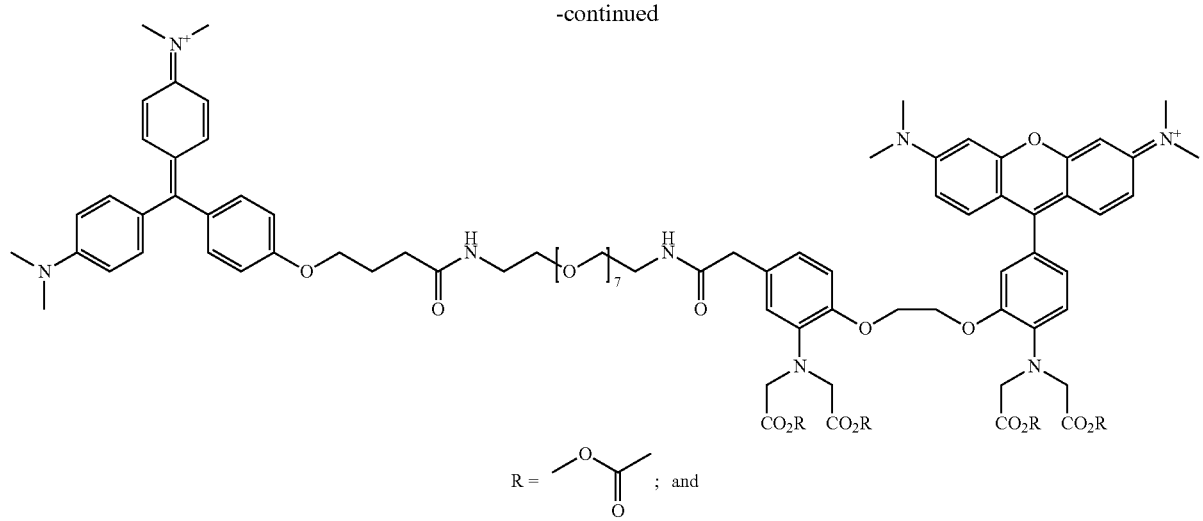

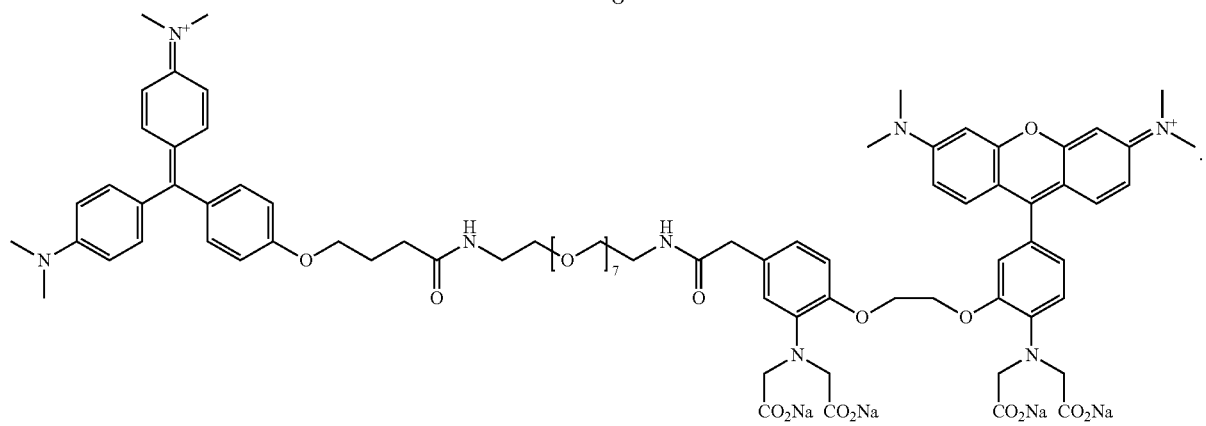

Also provided is a complex comprising any biosensor described herein, bound to an activator that causes an increase of fluorescence of the compound when the activator is bound to the compound when the donor moieties are excited. In one embodiment, the increase in fluorescence is at least 100-fold, and in another, the increase in fluorescence is at least 1000-fold. The activator may be attached to a selectivity component that localizes the activator at a site in a cell, tissue, organism, organ, etc. In one example, the selectivity component is a fusion protein comprising the activator and the selectivity component. In another embodiment, the selectivity component is crosslinked to the activator.

In one embodiment, the activator is an scFv fragment, such as an scFv fragment of one of SEQ ID NOS: 3-11, including:

```
                                          (SEQ ID NO: 3)
QAVVTQEPSVTVSPGGTVILTCGSSTGAVTSGHYANWFQQKPGQAPR

ALIFETDKKYPWTPGRFSGSLLGVKAALTISDAQPEDEAEYYCLLSDVD

GYLFGGGTQLTVLS;
```

```
                                          (SEQ ID NO: 4)
QAVVTQEPSVTVSPGGTVILTCGSSTGAVTSGHYANWFQQKPGQAPR

ALIFDTDKKYPWTPGRFSGSLLGVKAALTISDAQPEDEAEYYCLLSDVD

GYLFGGGTQLTVLS;
```

```
                                          (SEQ ID NO: 5)
QAVVTQEPSVTVSPGGTVILTCGSSTGAVTSGHYANWFQQKPGQAPR

ALIFETDKKYPWTPGRFSGSLLGVKAALTISDAQPEDEAEYYCSLSDVD

GYLFGGGTQLTVLS;
and
```

```
                                          (SEQ ID NO: 6)
QAVVTQEPSVTVSPGGTVILTCGSGTGAVTSGHYANWFQQKPGQAPR

ALIFDTDKKYPWTPGRFSGSLLGVKAALTISDAQPEDEAEYYCSLSDVD

GYLFGGGTQLTVLS;
``` or tandem or multiple repeats thereof, and optionally further comprising an amino acid sequence of a selectivity component. Tandem or multiple iterations of the activator and, when present, the selectivity component may be either directly linked via a peptide bond, or may comprise an intervening linker between the repeats which does not substantially impact the binding and activating function of the activator and, when present, the selectivity component.

Examples of suitable linkers are short peptide sequences encoded contiguously with the activator and, optionally, the selectivity component, such as G4S (GGGGS, SEQ ID NO: 15)

In another embodiment, the activator comprises a single-chain antibody, and in another, the activator comprises an engineered combination of linked antibody heavy and/or light chain components comprising an antibody antigen binding site (paratope). The activator is linked (covalently joined) via a peptide bond or a linker to a targeting group that interacts with a target in one embodiment, examples of the target including: one of an epitope, a protein, a modified protein (e.g., a glycoprotein), a nucleic acid, a nucleotide sequence, a small molecule, an active agent, an antibody, a cell, a cell-surface marker, a tissue, a site in an array or a particle.

In yet another embodiment, an environmental sensing method is provided for detecting the presence of and analyte or for quantifying the analyte. The method comprises contacting a biosensor with an activator. The biosensor is any biosensor described herein, comprising an activatable acceptor fluorogen linked by a linker to an environment-sensitive donor that interacts with an analyte. The activatable acceptor fluorogen produces a fluorescence signal increase of at least 100-fold when it interacts non-covalently with the activator as compared to when no activator is present. The environment-sensitive donor transfers excitation energy to the activatable acceptor fluorogen such that, when activated, the activatable acceptor fluorogen produces a detectable fluorescent signal when the environment-sensitive donor is excited and the environment-sensitive donor transfers different amounts of excitation energy to the activatable acceptor fluorogen when it interacts with the analyte as compared to when no analyte is present. The method further comprises illuminating the biosensor with light of a wavelength overlapping an excitation spectrum of the environment-sensitive donor, but not overlapping the excitation spectrum of the activatable acceptor fluorogen and measuring emissions from the activatable acceptor fluorogen.

In another embodiment, the method further comprises, after contacting the biosensor with the activator, illuminating the biosensor with light of a wavelength overlapping an excitation spectrum of the activatable acceptor fluorogen, but not overlapping an excitation spectrum of the environment-sensitive donor and measuring emissions from the activatable fluorogen. This will permit determining a ratio between the emissions obtained from the steps above. As above, the activator comprises a selectivity component, and the selectivity component binds, for example, to an epitope, a protein, a modified protein, a nucleic acid, a nucleotide sequence, a small molecule, an active agent, an antibody, a cell, a cell-surface marker, a tissue, a site in an array or a particle by the selectivity component. The method optionally comprises comparing the measured emissions from the activatable acceptor fluorogen to a control sample or to control sample data to determine the presence of or to quantify amounts of the analyte.

BRIEF DESCRIPTION OF THE DRAWINGS

FIG. 1A provides the peptide sequences for biosensor-activating scFvs used in this study (L5 MG, SEQ ID NO: 3; L5-MG E52D, SEQ ID NO: 4; L5-MG L91S, SEQ ID NO: 5; and L5-MG E52D L91S; SEQ ID NO: 6). Hyphens designate the core sequences. Additional FAPs are provided in FIG. 1B (HL4-MG core, SEQ ID NO: 7; H6-MG in PNL6 core, SEQ ID NO: 8, and L9-MG secreted form (MG67), SEQ ID NO: 9).

FIG. 2A depicts the DNA sequence of a construct encoding the L5-MG E52D pPNL6 fusion protein (SEQ ID NO: 1). FIGS. 2B and 2C depict the construct pPNL6 L5-MG E52D. FIG. 2D depicts region of the construct encoding L5-MG E52D mapped onto the nucleotide sequence of the relevant portion of pPNL6 L5-MG E52D (SEQ ID NOS: 1 and 2).

FIG. 3 provides an exemplary nucleotide sequence of an astrocyte-targeted promoter from glial fibrillary acidic protein (GFAP) (SEQ ID NO: 10).

FIG. 4 provides an exemplary nucleotide sequence of a neuron-targeted promoter from Synapsin I (SEQ ID NO: 11).

FIGS. 9C and 9D provide NMR spectral data for CY3SApH-MG.

FIG. 13A provides an expressed FAP sequence for pBabe-SacLac2-FAP-ADRB2 (SEQ ID NO: 12). FIG. 13B provides the nucleotide sequence of pBabeSacLac2-FAP-ADRB2 (SEQ ID NO: 13).

DETAILED DESCRIPTION

Figure 5:
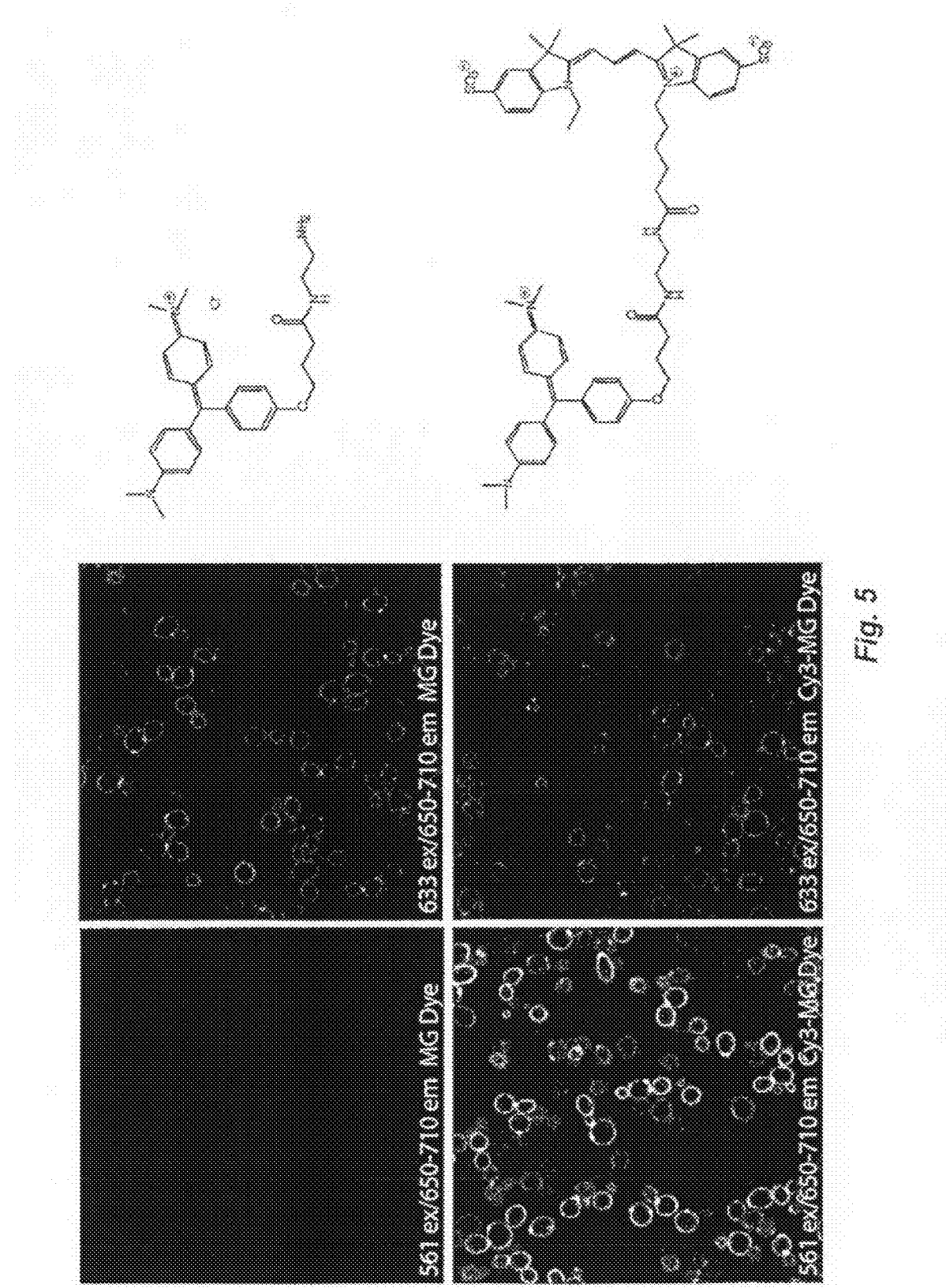
FIG. 5 shows a fluorogen activated and targeted probe based on CY3-MG intramolecular energy transfer. MG alone has no excitation at 561 nm but is efficiently excited by energy transfer from the coupled CY3 selectively.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values and are inclusive of the recited range end points. For definitions provided herein, those definitions also refer to word forms, cognates and grammatical variants of those words or phrases. Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. The articles "a" and "an" are used herein to refer to one or to more than one (i.e., to at least one) of the grammatical object of the article. By way of example, "an element" means one element or more than one element.

As described above, a biosensor, biosensor complexes, systems and methods are provided. In one embodiment, a biosensor is provided. The biosensor comprises an activatable acceptor fluorogen linked (e.g., covalently) by a linker to an environment-sensitive donor that interacts with an analyte. The activatable acceptor fluorogen produces a fluorescence signal increase of at least 100-fold, and typically greater than 1000-fold when it interacts non-covalently with an activator activatable acceptor fluorogen as compared to when no activator is present. The environment-sensitive donor transfers excitation energy (e.g., by FRET) to the activatable acceptor fluorogen such that, when activated, the activatable acceptor fluorogen produces a detectable fluorescent signal when the environment-sensitive donor is excited. The environment-sensitive donor transfers different amounts of excitation energy to the activatable acceptor fluorogen when it interacts with the analyte as compared to when no analyte is present. The linker is any suitable linker. This results in a low-background, targeted fluorogen that produces different signals in response to its local environment. According to certain embodiments, the biosensor has an average molecular weight of less than 50 kDa (kilodaltons) and in certain embodiments, less than 10 kDa.

The environment-sensitive donor is selected for its sensitivity to analytes about the biosensor. The analyte can be a molecular or environmental, for example and without limitation: calcium, zinc, sodium, potassium, hydrogen, pH (e.g., hydronium), voltage, hydrophobicity/hydrophilicity, small molecule drugs, Reactive oxygen species, singlet oxygen, peroxide, superoxide, hydroxyl radical, nitric oxide, and second messengers, e.g inositol triphosphate, diphosphates, and cAMP, cGMP. As shown herein, rhod2 derivatives effectively serve as a calcium-sensitive donors. Other Ca-sensitive donors include fura, fluo and indo-dyes available from Life Technologies, Inc. of Carlsbad, Calif., including, Fura-2, Fura-4F, Fura-6F, Fura-FF, Mag-Fura-2, Mag-Indo-1, BTC, Indo-1, Quin-2, Fluo-3, Fluo-4, Fluo-5F, Fluo-4FF, Fluo-5N, Mag-Fluo-4, Rhod-2, X-Rhod-1, Rhod 3, CALCIUM GREEN™-1, CALCIUM GREEN™-2, OREGON GREEN™ 488 Bapta-1, OREGON GREEN™ 488 Bapta-2, OREGON GREEN™ 488 Bapta-6F, OREGON GREEN™488 Bapta-5N, CALCIUM ORANGE™, CALCIUM CRIMSON™, Fura Red, and Calcein. Magnesium-sensitive dyes include, Mag-Fura-2 and Mag-Indo-1, MAGNESIUM GREEN™ and Mag-Fluo-4. Other ions can be detected, such as Zinc (e.g., FLUOZIN™ 2, FLUOZIN™-3, RHODZIN™-3, NEWPORT GREEN™ DCF, NEWPORT GREEN™ PDX and TSQ) and copper (e.g., PHEN GREEN™ FL and PHEN GREEN™ SK). For detecting pH changes, squaraine, and unsymmetrical cyanines, as well as fluorescein and fluorescein derivatives are suitable donors. For detecting voltage potentials across a cell membrane, Merocyanine XVII, Oxonol RH155, styryl Di4-ANEPPS, ANNINE-6 and Oxonol XXV are examples of useful voltage-sensitive donors. Dyes sensitive to hydrophilicity include: indole, CASCADE YELLOW™, prodan, Dansyl, DAPOXYL™, NBD, PyMPO, Pyrene and diethylaminocumarin.

Suitable activatable acceptor fluorogens are described in detail below, but include triarylmethine dyes; diarylmethine dyes; and monomethine dye, including cyanine dyes, malachite green, indocyanine green, acetylenic malachite green and dimethylindole red. Non-rigidized aromatic systems often are suitable for activatable acceptor fluorogens as they often lack fluorescence when unbound, but display fluorescence when they are physically constrained, e.g., by binding with an activator, such as an FAP. The liker may be any acceptable linking group so long as it does not prevent or it facilitates excitation energy transfer from the donor to the acceptor.

As illustrated in further detail below, activators, such as single chain variable fragment (scFv) molecules can be selected that are specific for nonfluorescent organic dye molecules, and which cause these dyes to be fluorescent only when they are bound to the protein module in the presence of free dye in solution. Using clones of high affinity (low nanomolar), this binding survives many wash steps, while with clones of low affinity (micromolar), the presence of the dye is required to maintain fluorescence signal. scFv modules are available in yeast display libraries and other display libraries, which can be used to generate specific binding partners for a wide variety of molecules and proteins. One key advantage of this genetically encoded system is that the selected antibodies, or dimers thereof can be used as expressible protein tags. This allows a relatively small unit (typically ~25 kDa molecular weight for a "whole" scFv, or as small as 11 kDa for a "single domain" scFv) to be expressed as a fusion protein with a specific partner in the cellular context, though the scFv can be attached to a specific partner, such as a cellular protein, ligand, receptor, antibody, etc. by any effective means.

Extended exposure of cells to illumination from high-intensity arc-discharge lamps or lasers can damage cellular physiology, hence enhancement of extinction should be helpful in reducing the excitation powers used. Single molecule studies have relied on red-shifted excitation lasers and sources to obtain longer timescale images without phototoxic effects. While the general rule is "redder is better" due to the lack of biological chromophores (autofluorescence) as one moves away from the blue-green region of the spectrum, the 561 nm laser has gained use in TIRF microscopy for living cells. This laser is well suited to dynamic measurements of living cells, and provides a high signal-to-noise ratio for single molecule experiments. In addition, this laser excites dyes like CY3 and Alexa 568 quite well, and these probes are known to be good energy transfer donors. For this reason, the probes are designed to excite at 561 nm, and to emit in far red wavelengths from 650 to 800 nm. This will produce probes with optimal signal over background.

A donor, and where applicable a mediator to bridge a spectral and/or distance gap between a donor and an acceptor, is any molecule or group that can act as a FRET activator to an acceptor. Although donors and acceptors are often referred to herein as independent chemical entities (e.g., CY3 or CY5) it is understood that those moieties are attached to the compound, and also are referred to as "donor moietie(s)" and "acceptor moietie(s)" or "donor group(s)" and "acceptor group(s)". Compounds described herein as being useful as donors and acceptors may be attached to the linker (e.g., linking group) by any useful means, according to well-known chemical methods. For example, the compounds can be linked to a linking group or other linker via a pendant carboxyl or amine group that either is depicted in the structures below, or can be added as a linker by any of a variety of methods.

As used herein a donor is a moiety or group that forms part of the biosensor compound. A donor can comprise one type of molecule (e.g., CY3) or two or more types of donors (e.g., CY3 and CY5) in dendronic systems. Two or more donors may be combined to further shift the emission spectrum of the biosensor away from the absorption spectrum of the donor. In one example, utilizing a cascade approach, a first, environment-sensitive donor has an absorbance spectrum and an emission spectrum that, at their greatest wavelength does not overlap or overlaps poorly with the absorbance spectrum of the acceptor. In such a case, a mediator that has an absorbance spectrum that overlaps with the emission spectrum of the first donor and an emission spectrum that overlaps with the absorbance spectrum of the acceptor, such that illumination of the biosensor at a wavelength within the absorbance spectrum of the first donor will result in emission by the acceptor.

Of note, a suitable donor need not be fully fluorescent, only capable of efficiently transferring energy to the acceptor to cause the acceptor to fluoresce, fluoresce to a greater extent, or fluoresce at a different wavelength in the presence of (e.g., bound by) an activator when it is excited. For example, the donor can be an azo dye, or a nitro-modified dye with very low quantum yield, provided the excited state lifetime is long enough to allow intramolecular energy transfer to the proximal acceptor, many of which are available commercially.

The acceptor may be any molecule which produces a detectable signal change in response to a change in environment, namely by binding by an activator, as such, it is deemed "activatable". Likewise, because the acceptor is activatable, the biosensor is considered to be activatable. For example; the signal change may be an increase or decrease in signal intensity, or a change in the type of signal produced (e.g., a shift in wavelength of the emission of the biosensor). For example, suitable reporters include molecules which produce optically detectable signals; for example, fluorescent and chemiluminescent molecules. In certain embodiments, the reporter molecule is a long wavelength fluorescent molecule which permits detection of the reporter signal through a tissue sample; for instance, non-invasive detection of the reporter in conjunction with in vivo applications.

According to certain embodiments, the acceptor is a non-rigidized aromatic system comprising aromatic rings and/or heteroaromatic rings bridged, for example, by a monomethine group. By non-rigidized, it is meant a group comprising two or more aromatic subgroups that are not spatially fixed or substantially spatially fixed.

The acceptor may be a pH sensitive fluorescent dye (pH sensor dye) which shows a spectral or fluorescent intensity change upon interaction with an activator. Interaction of the activator with the acceptor may lead to a shift in the pH of the microenvironment surrounding the acceptor due to the composition of acidic and basic residues on the activator. In turn, the shift in the pH microenvironment leads to a detectable spectral or fluorescent intensity change in the signal of the pH sensitive fluorescent dye molecule associated with the activator. In exemplary embodiments, a pH sensitive dye is selected with an appropriate pKa to lead to an optimal spectral change upon binding to the activator. A variety of pH sensitive dyes suitable for use in are commercially available. In exemplary embodiments, pH sensitive dyes include, for example, fluorescein, umbelliferones (coumarin compounds), pyrenes, resorufin, hydroxy esters, aromatic acids, styryl dyes, tetramethyl rhodamine dyes, and cyanine dyes, and pH sensitive derivatives thereof.

The acceptor may be a polarity sensitive fluorescent dye (polarity sensor dye) which shows a spectral change upon interaction with an activator. Interaction of the activator with a target molecule may lead to a shift in the polarity of the microenvironment surrounding the acceptor due to the composition of polar and/or non-polar residues on the activator. In turn, the change in the polarity of the microenvironment leads to a detectable spectral change in the signal of the polarity sensitive fluorescent dye molecule associated with the activator. A variety of polarity sensitive dyes suitable for use are commercially available. In exemplary embodiments, polarity sensitive dyes include, for example, merocyanine dyes, 5-((((2-iodoacetyl)amino)ethyl)amino)naphthalene-1-sulfonic acid (1,5-IAEDANS), and CPM, and polarity sensitive derivatives of merocyanine dyes, IAEDANS, and CPM.

The acceptor may be a fluorescent dye that is sensitive to changes in the microviscosity of the local environment (restriction sensor dye). Interaction of the activator with an acceptor may lead to a change in the microviscosity in the local environment surrounding the acceptor. In turn, the change in microviscosity may lead to a detectable spectral change in the signal of the mobility sensor dye molecule associated with the activator. For example, an increase of microviscosity upon target binding will restrict the dye and increase the quantum yield of the emitted fluorescence signal. A variety of restriction sensor dyes suitable for use are commercially available. In exemplary embodiments, restriction sensor dyes include, for example, monomethine and trimethine cyanine dyes, and microviscosity sensitive derivatives of monomethine and trimethine cyanine dyes.

Acceptors, when in complex with a nucleic acid (e.g., aptamer) or protein (e.g., FAP) that is specific for them, change their spectral properties. For example, Malachite Green and its analogs, which is not normally fluorescent, becomes strongly fluorescent when bound to an scFv specific for it. Many di- and tri-arylmethine analogs are good candidates for acceptors and FAP binders described herein. Many di- and tri-arylmethines have been prepared and are reviewed by Thomas Gessner, "Triarylmethane and diarylmethane Dyes", in Ullmann's Encyclopedia of Industrial Chemistry, Wiley (2005). Certain of these unbridged di- and tri-arylmethine dyes and similar dyes described elsewhere and yet to be synthesized, are believed to provide good acceptor dyes structures in biosensors once they have been appropriately modified according to the goals stated herein.

Useful analogs of Malachite Green (I) and Phenolphthalein (II) are shown below as representatives.

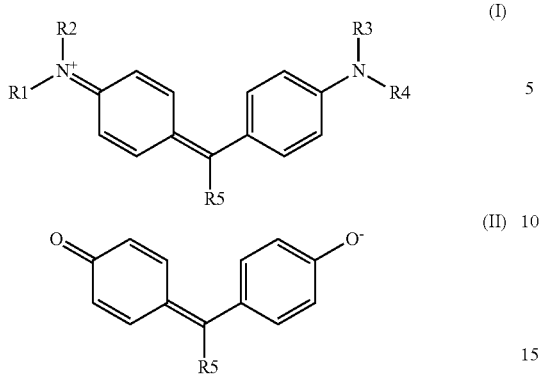

(I)

(II)

It may be preferred that the R1-R4 groups of the Malachite Green analogs are modified during development of biosensors in order to control the (1) the wavelength of light absorption and fluorescence, (2) the degree of activation of the acceptor dye, the water solubility of the biosensor, (3) the non-specific binding of the biosensor to cellular components, and (4) the ability or inability of the biosensor to cross biological membranes. The R5 group may be a substituted aryl group as in the Malachite green and Phenolphthalein classes of triarylmethine dyes. The R5 group of the diarylmethine dyes may be some other chemical substituent that accomplishes the goals just stated and in addition to provide a site for linkage of the donor dyes to the energy acceptor part of the biosensor. Other non-phenolic or non-amino groups that do not alter the resonance charge delocalization system that is responsible for the light absorption and emission systems of the dye may be substituted on the aryl rings the di- and triarylmethine structures to achieve the above goals. These groups may be selected from one or more of the atoms or groups listed below as "T". Examples of R1-R4 groups that may be useful for the above goals are —H, —CH$_3$, (CH$_2$)$_n$-T, and substituted aryl where the substituent are selected from atoms or groups listed below as "T" and n=0-6. In these structures "T" may be selected from —H, —OH, COO—, SO$_3^-$, —PO$_4^-$, amide, halogen, substituted single or multiple aryl, ether, polyether, PEGn (where n=1-30), heterocycles containing N, S or O atoms, substituted acetylenic groups, cyano, and carbohydrate groups. In one embodiment of the invention one of R1-R4 contains a linker attached to the donor dyes.

Examples of R5 groups for triarylmethine dyes are listed below where the substituents may be selected from those listed under "T" above. If present, the heteroatoms, X and Y, may be selected from N, O, S, Se, and C(CH$_3$)$_2$. In one embodiment of this invention one of the substituents is a linker attached to the donor dyes.

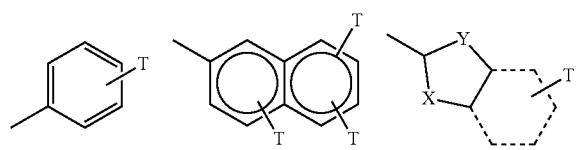

Examples of R5 groups for diarylmethine acceptor dyes may be selected from those listed under "T" above. In a preferred embodiment of this invention one of the substituents is a linker attached to the donor dyes.

The di and triarylmethine dyes may also include additional fused rings as long as the nitrogen or oxygen atoms that are the terminal components of the resonance charge delocalization system that is responsible for the light absorption and emission systems remains intact. These fused ring compounds may be useful to adjust the absorption and emission wavelengths of the acceptor in a desirable direction. One simple example is shown below where the substituents are selected from list "T" above.

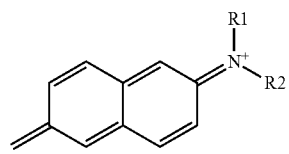

Below are members of cyanine dye family that contain substituted cyanines, merocyanines, styryl and oxonol dyes that are monomethine or contain additional methine groups. According to one embodiment, the acceptor is a diarylmethine or triarylmethine. For example, the acceptor has the structure:

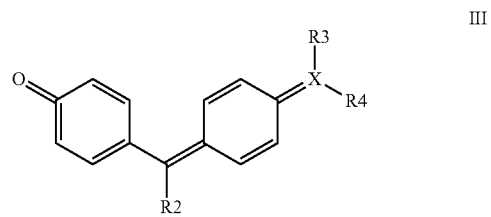

III in which R1 is aromatic, heteroaromatic, hydroxyl, amino, N-alkyl, N-alkanolyl (alcohol, e.g., N-hydroxyethyl), R2 is H, cyano, aromatic, heteroaromatic, acetylenic, alkyl, X is N, O, or S and R3 and R4 is alkyl, aryl, hydroxyethyl. The acceptor typically would be attached to the linker/dendron by R2. In certain embodiments, R1 is di-C$_{1-3}$ alkylamino, e.g., —N(CH$_3$)$_2$, R2 is a substituted phenylacetylene, substituted, e.g., with an amino or substituted amino group, such as —N—(CH$_3$)$_2$; —N—(CH$_3$)((CH$_2$)$_n$O(CH$_2$)$_m$COOH) in which n and m are independently 1, 2, 3 or 4; or —N—(CH$_3$)((CH$_2$)$_2$O(CH$_2$)$_3$COOH), phenyl, —N-alkyl-substituted phenyl, —O(CH$_2$)$_n$R5 substituted phenyl where n is 1-5 and R5 is carboxyl or amino, and R3 and R4 are independently C$_{1-3}$ alkyl, alkoxyl, alkanolyl, phenyl, C$_{1-3}$ alkyl-substituted phenyl. In one embodiment, R1 is —N(CH$_3$)$_2$, R2 is one of —O(CH$_2$)$_3$R5-substituted phenyl and

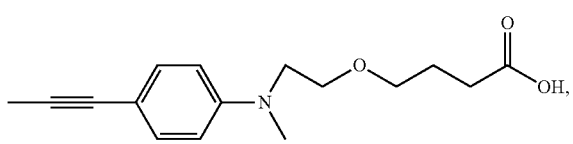 [SMILES: CC#Cc1ccc(N(C)CCOCCCC(=O)O)cc1]

and/or R3 and R4 are CH$_3$. The acceptor is attached to the biosensor via any one of R1-R4.

In other embodiments, the acceptor is a linker-modified derivative of one of:
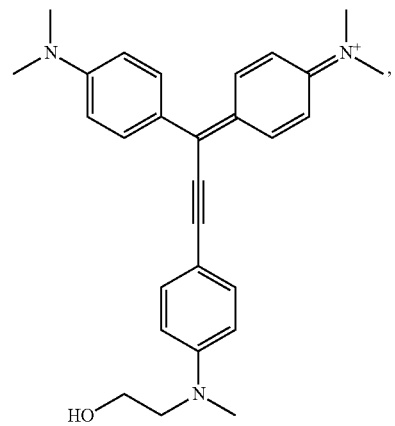
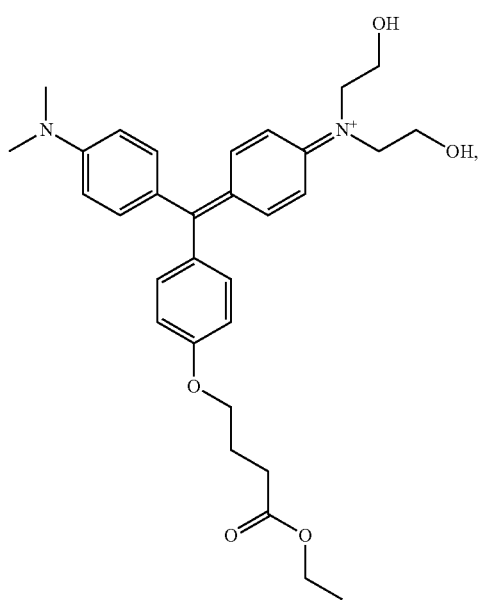
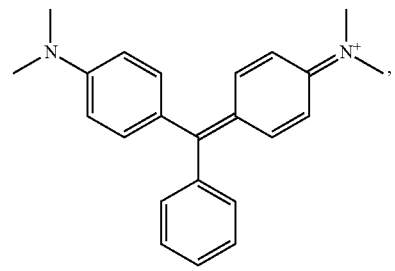
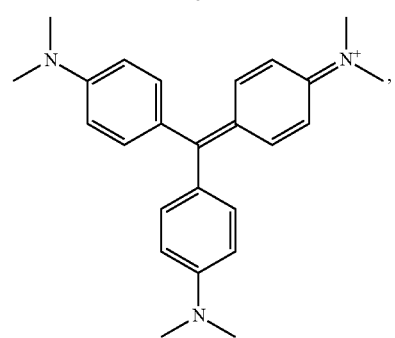
-continued
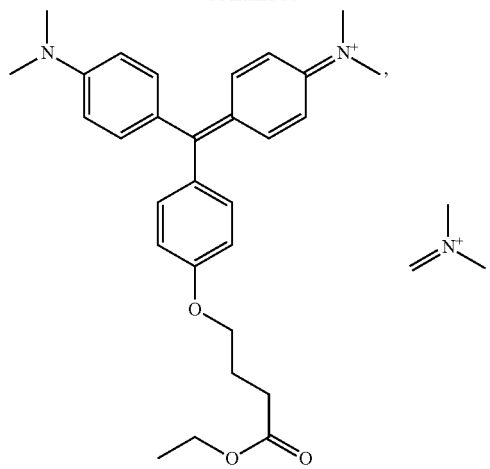
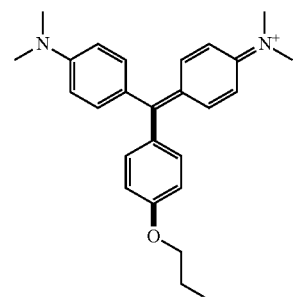
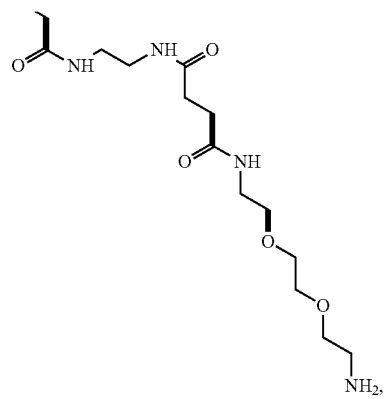
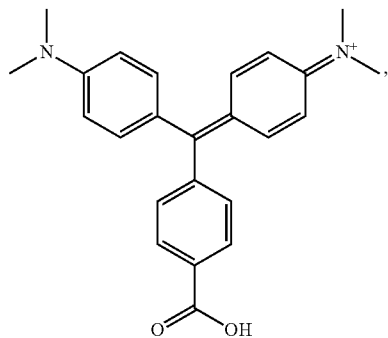

-continued

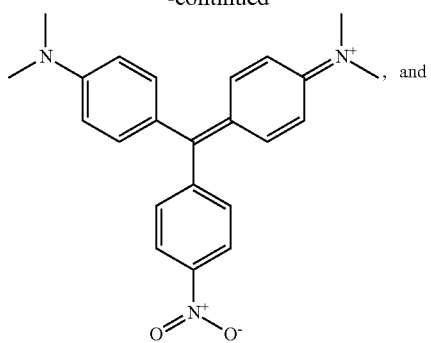

, and

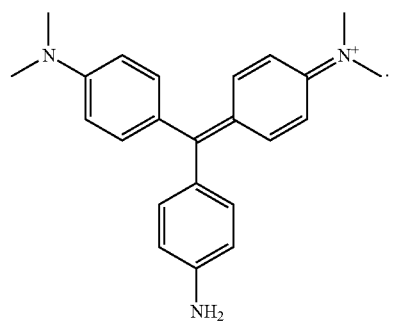

In certain embodiments, the acceptor is represented by structure IV, V and VI:

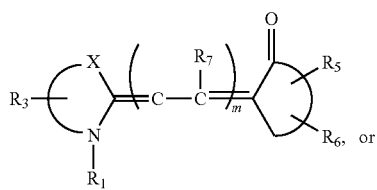
IV

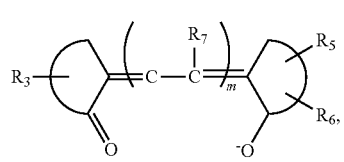
V, or

VI wherein: the curved lines represent the atoms necessary to complete a structure selected from one ring, two fused rings, and three fused rings, each said ring having five or six atoms, and each said ring comprising carbon atoms and, optionally, no more than two atoms selected from oxygen, nitrogen and sulfur; D, if present, is

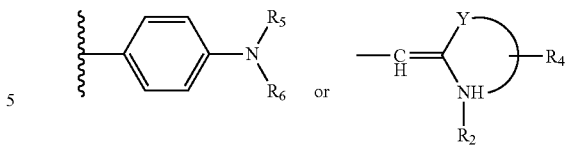

m is 1, 2, 3 or 4, and for cyanine, oxonol and thiazole orange, m can be 0; X and Y are independently selected from the group consisting of O, $S_3$ and —$C(CH_3)_2$—; at least one R1, R2, R3, R4, R5, R6, or R7 is selected from the group consisting of: a moiety that controls water solubility and non-specific binding, a moiety that prevents the reporter molecule from entering the cell through the membrane, a group that comprises, optionally with a linker, biotin a hapten, a His-tag, or other moiety to facilitate the process of isolating the selection entity, a fluorescent label optionally comprising a linker, a photoreactive group, or a reactive group such as a group containing isothiocyanate, isocyanate, monochlorotriazine, dichlorotriazine, mono- or di-halogen substituted pyridine, mono- or di-halogen substituted diazine, phosphoramidite, maleimnide, aziridine, sulfonyl halide, acid halide, hydroxysuccinimide ester, hydroxysulfosuccinimide ester, imido ester, hydrazine, axidonitrophenyl, azide, 3-(2-pyridyl dithio)-proprionamide, glyoxal, haloacetamido, or aldehyde; further-providing that R1 and R2 may be joined by a —$CHR_8$—$CHR_s$— or —$BF_2$— biradical; wherein; $R_8$ independently for each occurrence is selected from the group consisting of hydrogen, amino, quaternary amino, aldehyde, aryl, hydroxyl, phosphoryl, sulfhydryl, water solubilizing groups, alkyl groups of twenty-six carbons or less, lipid solubilizing groups, hydrocarbon solubilizing groups, groups promoting solubility in polar solvents, groups promoting solubility in nonpolar solvents, and -E-F; and further providing that any of R1, R2, R3, R4, R5, R6, or R7 may be substituted with halo, nitro, cyan, —$CO_2$alkyl, —$CO_2H$, —$CO_2$aryl, $NO_2$, or alkoxy, wherein:

F is selected from the group consisting of hydroxy, protected hydroxy, alkoxy, sulfonate, sulfate, carboxylate, and lower alkyl substituted amino or quartenary amino;

E is spacer group of formula —$(CH_2)_n$— wherein n is an integer from 0-5 inclusively;

alternatively, E is a spacer group of formula —$(CH_2$—O—$CH_2)_n$— wherein n is an integer from 0-5, inclusively In other embodiments, wherein m=0 in structures IV, V and VI, the following general structures VII, VIII and IX are afforded:

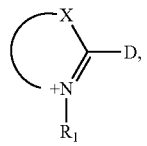
VII

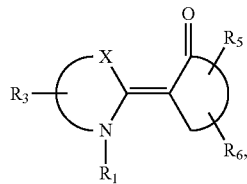
VIII

-continued

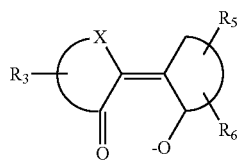

IX wherein: the curved lines represent the atoms necessary to complete a structure selected from one ring, two fused rings, and three fused rings, each said ring having five or six atoms, and each said ring comprising carbon atoms and, optionally, no more than two atoms selected from oxygen, nitrogen and sulfur; D, if present, is

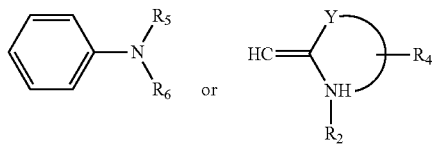

X and Y are independently selected from the group consisting of O, S, and —C(CH$_3$)$_2$—; at least one R1, R2, R3, R4, R5, R6, or R7 is selected from the group consisting of: a moiety that controls water solubility and non-specific binding, a moiety that prevents the reporter molecule from entering the cell through the membrane, a group that comprises, optionally with a linker, biotin, a hapten, a His-tag, or other moiety to facilitate the process of isolating the selection entity, a fluorescent label optionally comprising a linker, a photoreactive group, or a reactive group such as a group containing isothiocyanate, isocyanate, monochlorotriazine, dichlorotriazine, mono- or di-halogen substituted pyridine, mono- or di-halogen substituted diazine, phosphoramidite, maleimnide, aziridine, sulfonyl halide, acid halide, hydroxysuccinimide ester, hydroxysulfosuccinimide ester, imido ester, hydrazine, axidonitrophenyl, azide, 3-(2-pyridyl dithio)-proprionamide, glyoxal, haloacetamido, or aldehyde; further-providing that R1 and R2 may be joined by a —CHR$_8$—CHR$_s$— or —BF$_2$— biradical; wherein;

R$_8$ independently for each occurrence is selected from the group consisting of hydrogen, amino, quaternary amino, aldehyde, aryl, hydroxyl, phosphoryl, sulfhydryl, water solubilizing groups, alkyl groups of twenty-six carbons or less, lipid solubilizing groups, hydrocarbon solubilizing groups, groups promoting solubility in polar solvents, groups promoting solubility in nonpolar solvents, and -E-F; and further providing that any of R1, R2, R3, R4, R5, R6, or R7 may be substituted with halo, nitro, cyan, —CO$_2$alkyl, —CO$_2$H, —CO$_2$aryl, NO$_2$, or alkoxy wherein:

F is selected from the group consisting of hydroxy, protected hydroxy, alkoxy, sulfonate, sulfate, carboxylate, and lower alkyl substituted amino or quarternary amino;

E is spacer group of formula —(CH$_2$)$_n$— wherein n is an integer from 0-5 inclusively;

Alternatively, E is a spacer group of formula —(CH$_2$—O—CH$_2$)$_n$— wherein n is an integer from 0-5, inclusively.

The following are more specific examples of reporter molecules according to structure IV, V and VI:

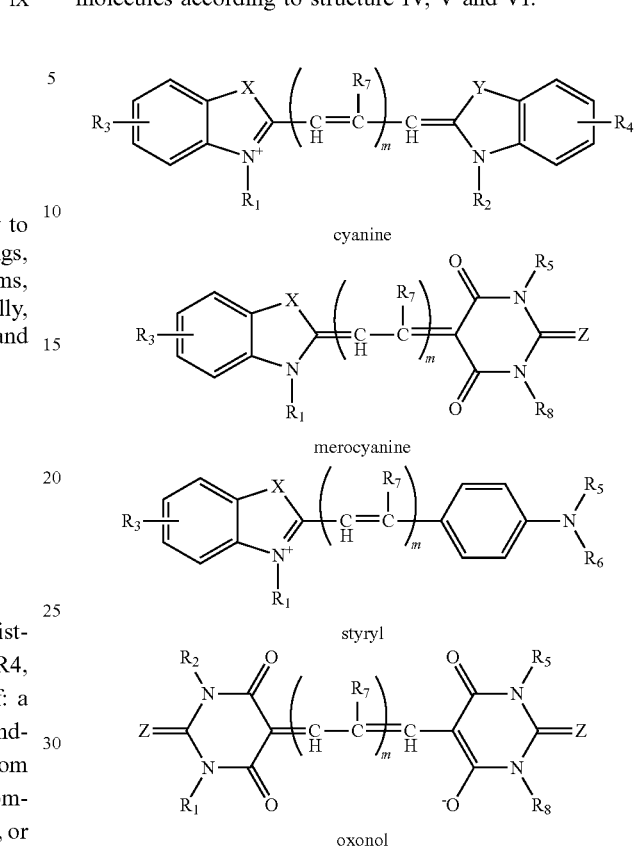

In these structures X and Y are selected from the group consisting of O. S and —CH(CH$_3$)$_2$—;

Z is selected from the group consisting of O and S; m is an integer selected from the group consisting of 0, 1, 2, 3 and 4 and, preferably an integer from 1-3. In the above formulas, the number of methine groups determines in part the excitation color.

The cyclic azine structures can also determine in part the excitation color. Often, higher values of m contribute to increased luminescence and absorbance. At values of m above 4, the compound becomes unstable. Thereupon, further luminescence can be imparted by modifications at the ring structures. When m=2, the excitation wavelength is about 650 nm and the compound is very fluorescent. Maximum emission wavelengths are generally 15-100 nm greater than maximum excitation wavelengths.

The polymethine chain of the luminescent dyes of this invention may also contain one or more cyclic chemical groups that form bridges between two or more of the carbon atoms of the polymethine chain. These bridges might serve to increase the chemical or photostability of the dye and might be used to alter the absorption and emission wavelength of the dye or change its extinction coefficient or quantum yield. Improved solubility properties may be obtained by this modification.

In various embodiments, the change of the acceptor dye upon interaction of the acceptor and the activator, and optionally the selectivity component with a target molecule, may include, for example, a shift in absorption wavelength, a shift in emission wavelength, a change in quantum yield, a change in polarization of the dye molecule, and/or a change in fluorescence intensity. The change can be two-fold, ten-fold, one hundred-fold, one thousand-fold or even higher. Any method suitable for detecting the spectral change associated with a given acceptor may be used, and suitable instruments for detection of a sensor dye spectral change, include, for example, fluorescent spectrometers, filter fluorometers, microarray readers, optical fiber sensor readers, epifluorescence microscopes, confocal laser scanning microscopes, two photon excitation microscopes, and flow cytometers.

In certain embodiments, the activator is associated with, e.g., linked to, a selectivity component. For example, the acceptor may be covalently attached to the selectivity component. The activator may be covalently attached to the selectivity component using standard techniques. For example, the activator may be directly attached to the selectivity component by forming a chemical bond between one or more reactive groups on the two molecules. For example, a thiol reactive group on the activator is attached to a cysteine residue (or other thiol containing molecule) on the selectivity component. Alternatively, the activator may be attached to the selectivity component via an amino group on the selectivity component. In another embodiment, the activator and selectivity component are presented on a contiguous fusion protein. In other embodiments, the activator may be attached to the selectivity component via a linker group. Suitable linkers include, for example, chemical groups, an amino acid or chain of two or more amino acids, a nucleotide or chain of two or more polynucleotides, polymer chains, and polysaccharides. In one example, the activator is attached to the selectivity component using a linker having a maleimide moiety. Linkers may be homofunctional (containing reactive groups of the same type), heterofunctional (containing different reactive groups), or photoreactive (containing groups that become reactive on illumination). A variety of photoreactive groups are known, for example, groups in the nitrene family.

One or more activators may be attached at one or more locations on the selectivity component. For example, two or more molecules of the same activator may be attached at different locations on a single selectivity component molecule. Alternatively, two or more different activators may be attached at different locations on a single selectivity component molecule. For example, 2, 3, 4, 5, 6, 7, 8, 9, 10 or more activators are attached at different sites on the selectivity component. The one or more activators may be attached to the selectivity component so as to maintain the activity of the activators and the selectivity component.

In certain embodiments, the activator further comprises a moiety that is specific for the selectivity component. For example, the activator may be linked to a substrate, a hapten, an antibody fragment or other binding reagent, etc. that is specific for the selectivity component. The activator may be covalently attached to the moiety using standard techniques. In certain embodiments the activator may be directly attached to the moiety by forming a chemical bond between one or more reactive groups on the two molecules. In other embodiments, the activator may be attached to the moiety via a linker group. Suitable linkers include, for example, chemical groups, an amino acid or chain of two or more amino acids, a nucleotide or chain of two or more polynucleotides, polymer chains, and polysaccharides. Linkers may be homofunctional (containing reactive groups of the same type), heterofunctional (containing different reactive groups), or photoreactive (containing groups that become reactive on illumination).

According to one embodiment, the activator component of the biosensor system described herein is a binding reagent, binding partner, ligand, FAP, or the like that interacts in any manner with the acceptor, such as by binding the acceptor, to cause the acceptor to become fluorescent, become increasingly fluorescent and/or shift its emission spectrum in response to illumination within the absorption spectrum of the biosensor (typically the absorbance spectrum of the donors). Optimally, absent binding of the activator to the acceptor, the acceptor will not fluoresce, or will not fluoresce insubstantially at a detection wavelength. The acceptor may fluoresce at another wavelength, but should not fluoresce in a manner that interferes with, or interferes substantially with, detection of fluorescence at the detection wavelength. It should be recognized that there may be low-level fluorescence in the absence of binding of the acceptor by the activator, but that background fluorescence should be significantly less than the level of fluorescence obtained when the acceptor is bound by the activator. Preferably, the "gain" in fluorescence of activator-bound biosensor to non-activator-bound biosensor is at least 100-fold, 1000-fold, 10,000-fold, or even greater. In an optimal embodiment, the acceptor will not fluoresce unless bound by the activator, or, as is more likely in the real world, will not substantially fluoresce unless bound by the activator. In practical use, there will be a certain level of background fluorescence, though it is preferably insubstantial.

As described in the examples herein, one non-limiting embodiment of the activator is an FAP (fluorogen activating peptide), a peptide produced by any useful means that binds to the fluorogen and/or the biosensor compound so as to increase the fluorescence of the acceptor at a given stimulatory wavelength and intensity. As described in the examples, one embodiment of the FAP is one or more scFv fragment, obtained from a yeast cell surface display library, and which activates the acceptor so that it fluoresces. Dimers or multimers (e.g., tandem repeats) of FAPs are equally useful as FAP monomers. The use of a yeast display library, and identification of a specific clone that expresses an FAP, permits directed evolution of the specific clone to produce derivatives with more desirable activity in a given biosensor system. An example of that is described below in relation to parent scFV L5-MG and evolved derivatives FAPs L5-MG E52D, L5-MG L91S, and L5-MG E52D L91S. Exemplary FAPs are as follows:

```
                                   (L5-MG; SEQ ID NO: 3)
QAVVTQEPSVTVSPGGTVILTCGSSTGAVTSGHYANWFQQKPGQAPR

ALIFETDKKYPWTPGRFSGSLLGVKAALTISDAQPEDEAEYYCLLSDVD

GYLFGGGTQLTVLS;

(L5-MG E52D; SEQ ID NO: 4)
QAVVTQEPSVTVSPGGTVILTCGSSTGAVTSGHYANWFQQKPGQAPR

ALIFDTDKKYPWTPGRFSGSLLGVKAALTISDAQPEDEAEYYCLLSDVD

GYLFGGGTQLTVLS;

(L5-MG L91S; SEQ ID NO: 5)
QAVVTQEPSVTVSPGGTVILTCGSSTGAVTSGHYANWFQQKPGQAPR

ALIFETDKKYPWTPGRFSGSLLGVKAALTISDAQPEDEAEYYCSLSDVD

GYLFGGGTQLTVLS;
and
```

(L5-MG E52D L91S; SEQ ID NO: 6)
QAVVTQEPSVTVSPGGTVILTCGSGTGAVTSGHYANWFQQKPGQAPR

ALIFDTDKKYPWTPGRFSGSLLGVKAALTISDAQPEDEAEYYCSLSDVD

GYLFGGGTQLTVLS, of these.

As would be readily evident to those of ordinary skill in the art, there are a multitude of methods for generating suitable activators. As shown herein as proof of concept, selection and evolution using yeast display libraries is an effective mechanism for generating useful FAPs. It should be evident that activators can be peptides, but also can be other molecules, such as nucleic acids and derivatives thereof, such as aptamers. Molecular libraries, such as libraries of small molecules, natural molecules, synthetic molecules, etc, also can readily be screened for activation of the acceptor by simply exposing the biosensor to a compound and determining if the compound can effectively activate the biosensor as described herein. The biosensor may be screened against libraries of random polypeptides, or libraries of binding agents, such as scFv fragments or other antibody fragments. Expression libraries of protein/peptide fragments or aptamers, expressed by bacteria, yeast, phage, etc. can be screened by colony fluorescence, fluorescence-activated cell sorting (FACS) or by affinity to surface-bound biosensor and subsequent amplification of retained phage, cells, etc. The growth, propagation, selection, and mutation of display/expression libraries is well known. Many commercial display/expression libraries are available and use thereof are well within the skill of the ordinary artisan.

International Patent Application Publication No. WO 2008/092041, incorporated herein by reference in its entirety, describes in detail not only the preparation of the L5-MG FAP and dimers thereof, but a large number of other methods by which activators (selectivity component as described in that publication) are selected, evaluated and used. In that reference, a yeast cell surface display library of recombinant human scFvs, obtained from Pacific Northwest National Laboratory was obtained and clones were initially sorted by one or more rounds of FACS, isolating cells that activate a desired fluorogen. Later, the FACS-screened cells were further enriched by affinity selection or further cell sorting.

The activator may be any molecule which is capable of selectively interacting with the acceptor to cause the acceptor/biosensor to fluoresce or increase fluorescence. Non-limiting examples of the activator include: polypeptides, nucleic acids (such as oligonucleotides, cDNA molecules or genomic DNA fragments), carbohydrates, or other suitable organic or inorganic molecules.

The activator also may comprise or be attached to a selectivity component that binds, interacts with, or duplicates one or more components of a cell or organism. Non-limiting examples of selectivity components include: a protein or polypeptide, an antibody or other binding agent, and aptamer, a ligand, an agonist or antagonist, a metabolite or chemical moiety, a nucleic acid, such as DNA, RNA, etc., a cell, a microorganism (such as bacteria, fungi and viruses), a hormone, a receptor, a cytokine, a drug molecule, a carbohydrate, a pesticide, a dye, an amino acid, a small organic or inorganic molecules, or a lipid. Exemplary target molecules for the selectivity component include, for example, molecules involved in tissue differentiation and/or growth, cellular communication, cell division, cell motility, and other cellular functions that take place within or between cells, including regulatory molecules such as growth factors, cytokines, morphogenetic factors, neurotransmitters, and the like. In certain embodiments, target molecules may be bone morphogenic protein, insulin-like growth factor (IGF), and/or members of the hedgehog and Wnt polypeptide families. Other examples of selectivity components include: pathway and network proteins (for example, enzymes such as kinases or phosphatases), antibody fragments, non-antibody receptor molecules, aptamers, template imprinted materials, and organic or inorganic binding elements. Selectivity components having limited crossreactivity are generally preferred.

The activator and selectivity component may be part of a bifunctional compound, such as a fusion (chimeric) protein, or a combination of mono-functional components, such as a cross-linked composition in which an activator is linked by a linking group to a selectivity component. The activator and selectivity component may be similar chemical entities, as in the case of a bifunctional chimeric protein, two linked scFv fragments or an scFv activator linked to a protein, antibody or other polypeptide. They also may be different chemical entities, as in the case of the activator being a polypeptide, such as an scFv fragment, and the selectivity component is a nucleic acid, such as an aptamer, a template imprinted material, a metabolite, a lipid, a polysaccharide, a virion, etc.

As used herein, the term "selectivity component" refers to a molecule capable of interacting with a target molecule. Selectivity components having limited cross-reactivity are generally preferred. In certain embodiments, suitable selectivity components include, for example, polypeptides, such as for example, antibodies, monoclonal antibodies, or derivatives or analogs thereof, including without limitation: Fv fragments, single chain Fv (scFv) fragments, Fab1 fragments, F(ab')2 fragments, single domain antibodies, camelized antibodies and antibody fragments, humanized antibodies and antibody fragments, and multivalent versions of the foregoing; multivalent binding reagents including without limitation: monospecific or bispecific antibodies, such as disulfide stabilized Fv fragments, scFv tandems ((ScFv)2 fragments), diabodies, tribodies or tetrabodies, which typically are covalently linked or otherwise stabilized (i. e., leucine zipper or helix stabilized) scFv fragments; and other binding reagents including, for example, aptamers, template imprinted materials (such as those of U.S. Pat. No. 6,131, 580), and organic or inorganic binding elements. In exemplary embodiments, a selectivity component specifically interacts with a single epitope. In other embodiments, a selectivity component may interact with several structurally related epitopes.

The term "ligand" refers to a binding moiety for a specific target, its binding partner. The molecule can be a cognate receptor, a protein a small molecule, a hapten, or any other relevent molecule. The term "antibody" refers to an immunoglobulin, derivatives thereof which maintain specific binding ability, and proteins having a binding domain which is homologous or largely homologous to an immunoglobulin binding domain. As such, the antibody operates as a ligand for its cognate antigen, which can be virtually any molecule. Natural antibodies comprise two heavy chains and two light chains and are bi-valent. The interaction between the variable regions of heavy and light chain forms a binding site capable of specifically binding an antigen (e.g., a paratope). The term "VH" refers to a heavy chain variable region of an antibody. The term "VL" refers to a light chain variable region of an antibody. Antibodies may be derived from natural sources, or partly or wholly synthetically produced.

An antibody may be monoclonal or polyclonal. The antibody may be a member of any immunoglobulin class, including any of the human classes: IgG, IgM, IgA, IgD, and IgE.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')2, Fv, dsFv, scFv, diabody, and Fd fragments. The antibody fragment may be produced by any means. For instance, the antibody fragment may be enzymatically or chemically produced by fragmentation of an intact antibody, it may be recombinantly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The term "Fab" refers to an antibody fragment that is essentially equivalent to that obtained by digestion of immunoglobulin (typically IgG) with the enzyme papain. The heavy chain segment of the Fab fragment is the Fd piece. Such fragments may be enzymatically or chemically produced by fragmentation of an intact antibody, recombinantly produced from a gene encoding the partial antibody sequence, or it may be wholly or partially synthetically produced. Methods for preparing Fab fragments are known in the art. See, for example, Tijssen, Practice and Theory of Enzyme Immunoassays (Elsevier, Amsterdam, 1985).

The term "Fab" refers to an antibody fragment that is essentially equivalent to that obtained by reduction of the disulfide bridge or bridges joining the two heavy chain pieces in the F(ab')2 fragment. Such fragments may be enzymatically or chemically produced by fragmentation of an intact antibody, recombinantly produced from a gene encoding the partial antibody sequence, or it may be wholly or partially synthetically produced.

The term "F(ab')2" refers to an antibody fragment that is essentially equivalent to a fragment obtained by digestion of an immunoglobulin (typically IgG) with the enzyme pepsin at pH 4.0-4.5. Such fragments may be enzymatically or chemically produced by fragmentation of an intact antibody, recombinantly produced from a gene encoding the partial antibody sequence, or it may be wholly or partially synthetically produced.

The term "Fv" refers to an antibody fragment that consists of one VH and one VL domain held together by noncovalent interactions. The term "dsFv" is used herein to refer to an Fv with an engineered intermolecular disulfide bond to stabilize the VH-VL pair. Methods for preparing Fv fragments are known in the art. See, for example, Moore et al., U.S. Pat. No. 4,462,334; Hochman et al., Biochemistry 12: 1130 (1973); Sharon et al., Biochemistry 15: 1591 (1976); and Ehrlich et al., U.S. Pat. No. 4,355,023.

The terms "single-chain Fvs" and "scFvs" refers to recombinant antibody fragments consisting of only the variable light chain (VL) and variable heavy chain (VH) covalently connected to one another by a polypeptide linker. Either VL or VH may be the NHb-terminal domain. The polypeptide linker may be of variable length and composition so long as the two variable domains are bridged without serious steric interference. In exemplary embodiments, the linkers are comprised primarily of stretches of glycine and serine residues with some glutamic acid or lysine residues interspersed for solubility. Methods for preparing scFvs are known in the art. See, for example, PCT/US/87/02208 and U.S. Pat. No. 4,704,692.

The term "single domain antibody" or "Fd" refers to an antibody fragment comprising a VH domain that interacts with a given antigen. An Fd does not contain a VL domain, but may contain other antigen binding domains known to exist in antibodies, for example, the kappa and lambda domains. In certain embodiments, the Fd comprises only the FL component. Methods for preparing Fds are known in the art. See, for example, Ward et al., Nature 341:644-646 (1989) and EP 0368684 A1.

The term "single chain antibody" refers to an antibody fragment that comprises variable regions of the light and heavy chains joined by a flexible linker moiety. Methods for preparing single chain antibodies are known in the art. See, for example, U.S. Pat. No. 4,946,778 to Ladner et al.

The term "diabodies" refers to dimeric scFvs. The components of diabodies typically have shorter peptide linkers than most scFvs and they show a preference for associating as dimers. The term diabody is intended to encompass both bivalent (i.e., a dimer of two scFvs having the same specificity) and bispecific (i.e., a dimer of two scFvs having different specificities) molecules. Methods for preparing diabodies are known in the art. See, for example, EP 404097 and WO93/11161. The term "triabody" refers to trivalent constructs comprising 3 scFv's, and thus comprising 3 variable domains (see, e.g., Iliades et al., FEBS Lett. 409 (3):43741 (1997)). Triabodies is meant to include molecules that comprise 3 variable domains having the same specificity, or 3 variable domains wherein two or more of the variable domains have different specificities. The term "tetrabody" refers to engineered antibody constructs comprising 4 variable domains (see, e.g., Pack et al. 5 J Mol Biol. 246(1): 28-34 (1995) and Coloma & Morrison, Nat Biotechnol. 15(2): 159-63 (1997)). Tetrabodies is meant to include molecules that comprise 4 variable domains having the same specificity, or 4 variable domains wherein two or more of the variable domains have different specificities.

As used herein, the term "epitope" refers to a physical structure on a molecule that interacts with a selectivity component, such as an antibody. In exemplary embodiments, epitope refers to a desired region on a target molecule that specifically interacts with a selectivity component. "Interact" is meant to include detectable interactions between molecules, such as may be detected using, for example, a hybridization assay. Interact also includes "binding" interactions between molecules. Interactions may be, for example, protein-protein, protein-nucleic acid, protein-small molecule or small molecule-nucleic acid, and includes for example, antibody-antigen binding, receptor-ligand binding, hybridization, and other forms of binding. In certain embodiments, an interaction between a ligand and a specific target will lead to the formation of a complex, wherein the ligand and the target are unlikely to dissociate. Such affinity for a ligand and its target can be defined by the dissociation constant (Kd) as known in the art. A complex may include a ligand for a specific dye and is referred to herein as a "ligand-dye" complex.

The term "immunogen" traditionally refers to compounds that are used to elicit an immune response in an animal, and is used as such herein. However, many techniques used to produce a desired selectivity component, such as the phage display and aptamer methods described below, do not rely wholly, or even in part, on animal immunizations. Nevertheless, these methods use compounds containing an "epitope," as defined above, to select for and clonally expand a population of selectivity components specific to the "epitope." These in vitro methods mimic the selection and clonal expansion of immune cells in vivo, and, therefore, the compounds containing the "epitope" that is used to clonally expand a desired population of phage, aptamers and the like in vitro are embraced within the definition of "immunogens."

Similarly, the terms "hapten" and "carrier" have specific meaning in relation to the immunization of animals, that is, a "hapten" is a small molecule that contains an epitope, but is incapable as serving as an immunogen alone. Therefore, to elicit an immune response to the hapten, the hapten is conjugated with a larger carrier, such as bovine serum albumin or keyhole limpet hemocyanin, to produce an immunogen. A preferred immune response would recognize the epitope on the hapten, but not on the carrier. As used herein in connection with the immunization of animals, the terms "hapten" and "carrier" take on their classical definition. However, in the in vitro methods described herein for preparing the desired binding reagents, traditional "haptens" and "carriers" typically have their counterpart in epitope-containing compounds affixed to suitable substrates or surfaces, such as beads and tissue culture plates.

In certain embodiments, the activator and/or selectivity component (as used herein, either the activator, the selectivity component or both, independently) is an antibody or an antibody fragment. For example, the selectivity component may be a monoclonal antibody, or derivatives or analogs thereof, including without limitation: Fv fragments, single chain Fv (scFv) fragments, Fab' fragments, F(ab')$_2$ fragments, single domain antibodies, camelized antibodies and antibody fragments, humanized antibodies and antibody fragments, and multivalent versions of the foregoing; multivalent activators including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; receptor molecules which naturally interact with a desired target molecule.

In one embodiment, the activator and/or selectivity component is an antibody. Preparation of antibodies may be accomplished by any number of well-known methods for generating monoclonal antibodies. These methods typically include the step of immunization of animals, typically mice; with a desired immunogen (e.g., a desired target molecule-or fragment thereof). Once the mice have been immunized, and preferably boosted one or more times with the desired immunogen(s), monoclonal antibody-producing hybridomas may be prepared and screened according to well known methods (see, for example, Kuby, Janis, IMMUNOLOGY, Third Edition, pp. 131-139, W.H. Freeman & Co. (1997), for a general overview of monoclonal antibody production).

Methods for production of antibodies and other binding reagents have become extremely robust. In vitro methods that combine antibody recognition and phage display techniques allow one to amplify and select antibodies or other binding reagents with very specific binding capabilities. See, for example, Holt, L. J. et al., "The Use of Recombinant Antibodies in Proteomics," Current Opinion in Biotechnology 2000, 11:445-449, incorporated herein by reference. These methods typically are much less cumbersome than preparation of hybridomas by traditional monoclonal antibody preparation methods. Binding epitopes may range in size from small organic compounds such as bromo uridine and phosphotyrosine to oligopeptides on the order of 7-9 amino acids in length.

In another embodiment, the activator and/or selectivity component is an antibody fragment. Selection and preparation of antibody fragments may be accomplished by any number of well-known methods. Phage display, bacterial display, yeast display, mRNA display and ribosomal display methodologies may be utilizes to identify and clone desired technology may be used to generate antibody fragment activators that are specific for a desired target molecule, including, for example, Fab fragments, Fvs with an engineered intermolecular disulfide bond to stabilize the $V_H$-VL pair, scFvs, or diabody fragments.

In certain embodiments, the activator and/or selectivity component comprises a polypeptide sequence having at least about 85%, at least about 90%, at least about 95%, about 96%, about 97%, about 98%, about 99% or about 100% sequence identity to any of the polypeptide sequences of SEQ ID NOS: 3-9 (FIGS. 1A and 1B). Vectors to produce the activator may be prepared as described below and in WO 08/092041, with the nucleic acid encoding the polypeptide of SEQ ID NO: 3 or other activator sequences (SEQ ID NOS: 4-9), inserted in frame between flanking HA and c-myc epitopes of the pPNL6 plasmid and its homologs (for example, SEQ ID NO: 2 in FIG. 2), and used to transfect host cells as described herein and in WO 08/092041.

Production of scFv antibody fragments using display methods, including phage, bacterial, yeast, ribosomal and mRNA display methods can be employed to produce the activator and/or selectivity component, as described herein. As described below, yeast display methods were used to produce an activator described below. Yeast display methods are described, for example, in Boder, et al. (2000) Proc. Natl. Acad. Sci USA 97:10701-5; Swers, et al. (2004) Nucl. Acids. Res. 32:e36; and Yeast Display scFv Antibody Library User's Manual, Pacific Northwest National Laboratory, Richland, Wash. 99352, Revision Date: MF031112.

Ribosome display also is a useful method for producing the activator and/or selectivity component. Ribosome display is a technique used to perform in vitro protein evolution to create proteins that can bind to a desired ligand. The process results in translated proteins that are associated with their mRNA progenitor which is used, as a complex, to bind to an immobilized ligand in a selection step. The mRNA encodes random polypeptides, and the diversity can far exceed that of phage and yeast display systems. The mRNA-protein hybrids that bind well to a ligand are then reverse transcribed to cDNA and their sequence amplified via PCR. The end result is a nucleotide sequence that can be used to create tightly binding proteins. (see, e.g., Hanes J, Plückthun A (1997) Proc Natl Acad Sci USA 91:4937-4942; He M, Taussig M J (1997) Nucleic Acids Res 25:5132-5134; and In Vitro Protein Expression Guide, PROMEGA (2005), pp-29-33, Chapter 6, Ribosome Display)). Ribosome display either begins with a DNA sequence or naive library of sequences coding for a specific protein. The sequence is transcribed, and then translated in vitro into protein. However, the DNA library coding for a particular library of binding proteins is genetically fused to a spacer sequence lacking a stop codon. This spacer sequence, when translated, is still attached to the peptidyl tRNA and occupies the ribosomal tunnel, and thus allows the protein of interest to protrude out of the ribosome and fold. What results is a complex of mRNA, ribosome, and protein which can bind to surface-bound ligand. This complex is stabilized with the lowering of temperature and the addition of cations such as $Mg^{2+}$.

During the subsequent binding, or panning, stages, the ribosome complex is introduced to surface-bound ligand. This can be accomplished several ways, for example using an affinity chromatography column with a resin bed containing ligand, a 96-well plate with immobilized surface-bound ligand, or magnetic beads that have been coated with ligand. The complexes that bind well are immobilized. Subsequent elution of the binders via high salt concentrations, chelating agents, or mobile ligands which complex with the binding motif of the protein allow dissociation of the mRNA. The mRNA can then be reverse transcribed back into cDNA, undergo mutagenesis, and iteratively fed into the process with greater selective pressure to isolate even better binders.

As it is performed entirely in vitro, there are two main advantages of ribosomal display methods over other selection technologies. First, the diversity of the library is not limited by the transformation efficiency of bacterial cells, but only by the number of ribosomes and different mRNA molecules present in the test tube. Second, random mutations can be introduced easily after each selection round, as no library must be transformed after any diversification step. This allows facile directed evolution of binding proteins over several generations.

In certain display methods, such as phage and yeast display, a library of $V_H$ and $V_L$ chains are prepared from mRNA of B-cells either naïve or immunized animals (such as a mouse, rabbit, goat or other animal), or even from polyclonal or monoclonal hybridoma. The mRNA is reverse-transcribed by known methods using either a polyA primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding an scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as an Fab' fragment, may be cloned into phage display vectors for surface expression on phage particles. The phage may be any phage, such as lambda, but typically is a filamentous phage, such as fd and M13, typically M13.

In display vectors, the $V_H$-linker-$V_L$ sequence is cloned into a surface protein (e.g., for M13, the surface proteins g3p (pHI) or g8p, most typically g3p). Display systems also include phagemid systems, which are based on a phagemid plasmid vector containing the phage surface protein genes (for example, g3p and g8p of M13) and the phage origin of replication. To produce phage particles, cells containing the phagemid are rescued with helper phage providing the remaining proteins needed for the generation of phage. Only the phagemid vector is packaged in the resulting phage particles because replication of the phagemid is grossly favored over replication of the helper phage DNA. Phagemid packaging systems for production of antibodies are commercially available. One example of a commercially available phagemid packaging system that also permits production of soluble ScFv fragments in bacteria cells is the Recombinant Phage Antibody System (RPAS), commercially available from GE Healthcare, Piscataway, N.J., and the pSKAN Phagemid Display System, commercially available from MoBiTec (Boca Scientific, Boca Raton, Fla.).

Phage display systems, their construction and screening methods are described in detail in, among others, U.S. Pat. Nos. 5,702,892, 5,750,373, 5,821,047 and 6,127,132, each of which are incorporated herein by reference in their entirety.

Typically, once a population of clones, such as phage, yeast, bacteria, ribosomes, etc., are produced that display a desired polypeptide, such as an antibody fragment, epitope specific clones are selected by their affinity for the desired immunogen and, optionally, their lack be used for physically separating immunogen-binding clones from non-binding clones. Typically the immunogen is fixed to a surface and the clones are contacted with the surface. Non-binding clones are washed away while binding clones remain bound. Bound clones are eluted and propagated to amplify the selected clones. A number of iterative rounds of affinity selection typically are used, often increasingly higher stringency washes, to amplify immunogen binding clones of increasing affinity. Negative selection techniques also may be used to select for lack of binding to a desired target. In that case, un-bound (washed) clones are amplified. In the context of the present invention, fluorescence of bound biosensor can be used as a selectable marker for identifying clones. High throughput methods, such as FACS, may initially be employed to select clones, followed, optionally by detection of fluorescence in plated colonies by fluorescent imaging techniques.

Although it is preferred to use spleen cells and/or B-lymphocytes from animals preimmunized with a desired immunogen as a source of cDNA from which the sequences of the $V_H$ and $V_L$ chains are amplified by RT-PCR, naive (un-immunized with the target immunogen) splenocytes and/or B-cells may be used as a source of cDNA to produce a polyclonal set of VH and $V_L$ chains that are selected in vitro by affinity, typically by the above-described phage display (phagemid) method. When naive B-cells are used, during affinity selection, the washing of the first selection step typically is of very high stringency so as to avoid loss of any single clone that may be present in very low copy number in the polyclonal phage library. By this naive method, B-cells may be obtained from any polyclonal source, B-cell or splenocyte cDNA libraries also are a source of cDNA from which the $V_H$ and $V_L$ chains may be amplified. For example, suitable murine and human B-cell, lymphocyte and splenocyte cDNA libraries are commercially available from Agilent Technologies/Stratagene and from Invitrogen. Phagemid antibody libraries and related screening services are provided commercially by MorphoSys USA, Inc., of Charlotte, N.C. (CysDisplay).

The activator and/or selectivity component does not have to originate from biological sources, such as from naive or immunized immune cells of animals or humans. The activator and/or selectivity component may be screened from a combinatorial library of synthetic peptides. One such method is described in U.S. Pat. No. 5,948,635, incorporated herein by reference, which described the production of phagemid libraries having random amino acid insertions in the pill gene of M13. These phage may be clonally amplified by affinity selection as described above.

Panning in a culture dish or flask is one way to physically separate binding clones from non-binding clones. Panning may be carried out in 96 well plates in which desired immunogen structures have been immobilized. Functionalized 96 well plates, typically used as ELISA plates, may be purchased from Pierce of Rockwell, Ill. biosensor may be synthesized directly on $NH_2$ or COOH functionalized plates in an N-terminal to C-terminal direction. Other affinity methods for isolating clones having a desired specificity include affixing biosensor to beads. The beads may be placed in a column and clones may be bound to the column, washed and eluted according to standard procedures. Alternatively, the beads may be magnetic so as to permit magnetic separation of the binding particles from the non-binding particles. The immunogen also may be affixed to a porous membrane or matrix, permitting easy washing and elution of the binding clones.

In certain embodiments, it may be desirable to increase the specificity of the activator and/or selectivity component for a given target molecule or reporter molecule using a negative selection step in the affinity selection process. For example, activator- and/or selectivity component-displaying clones may be contacted with a surface functionalized with fluorogens distinct from the target molecule or reporter molecule. Clones are washed from the surface and non-binding clones are grown to clonally expand the population of non-binding clones thereby deselecting clones that are not specific for the desired target molecule. In certain embodiments, random synthetic peptides may be used in the negative selection step. In other embodiments, one or more immunogens having structural similarity to the acceptor or donors may be used in the negative selection step.

Screening of the activator and/or selectivity components will best be accomplished by high throughput parallel selection, as described in Holt et al. Alternatively, high throughput parallel selection may be conducted by commercial entities, such as by MorphoSys USA, Inc.

In certain embodiments, it may be desirable to mutate the binding region of the activator and/or selectivity component and select for the activator and/or selectivity component with superior binding characteristics as compared to the un-mutated activator. This may be accomplished by any standard mutagenesis technique, such as by PCR with Taq polymerase under conditions that cause errors. In such a case, the PCR:primers could be used to amplify scFv- or binding reagent-encoding sequences of (e.g.) phagemid plasmids under conditions that would cause mutations. The PCR product may then be cloned into a (e.g.) phagemid vector and screened for the desired specificity, as described above.

In other embodiments, the activator and/or selectivity component is modified to make them more resistant to cleavage by proteases. For example, the stability of the selectivity components that comprise polypeptides may be increased by substituting one or more of the naturally occurring amino acids in the (L) configuration with D-amino acids. In various embodiments, at least 1%, 5%, 10%, 20%, 50%, 80%, 90% or 100% of the amino acid residues of the activators may be of the D configuration. The switch from L to D amino acids neutralizes the digestion capabilities of many of the ubiquitous peptidases found in the digestive tract.

Alternately, enhanced stability of the activator and/or selectivity component is achieved by the introduction of modifications of the traditional peptide linkages. For example, the-introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of the activator and/or selectivity component may be achieved by intercalating one or more dextrorotatory amino acids (such as, dextrorotatory phenylalanine or dextrorotatory tryptophan) between the amino acids of the activator, hi exemplary embodiments, such modifications increase the protease resistance of the selectivity components without affecting their activity or specificity of interaction with a desired target molecule or reporter molecule.

In certain embodiments, the antibodies or variants thereof, may be modified to make them less immunogenic if and when administered to a subject. For example, if the subject is human, the antibody may be "humanized"; where the complementarity determining region(s) of the hybridoma-derived antibody has been transplanted into a human monoclonal antibody, for example as described in U.S. Pat. No. 6,407,213. Also, transgenic mice, or other mammals, may be used to express humanized antibodies. Such humanization may be partial or complete.

In another embodiment, the activator and/or selectivity component is a Fab fragment. Fab antibody fragments may be obtained by proteolysis of an immunoglobulin molecule using the protease papain. Papain digestion yields two identical antigen-binding fragments, termed "Fab fragments", each with a single antigen-binding site, and a residual "Fc fragment". In still another embodiment, the selectivity component is an F(ab')2 fragment. F(ab')2 antibody fragments may be prepared from IgG molecules using limited proteolysis with the enzyme pepsin. In other embodiments, the selectivity component may be a network or pathway protein such as an enzyme, for example, a phosphatase or kinase. Such proteins may be mutated to create a binding site for a reporter and/or target molecule. For example, a method of making a selectivity component biosensor from network and pathway proteins in cells and tissues may comprise mutating a specific region on a selected protein to create a binding site for a reporter or target molecule. The region selected for mutation may be randomly or partially randomly mutated by creating mutations in selected regions of the gene that codes for the protein that is to be converted into a selectivity component. The gene with the mutated region(s) may be incorporated by transfection into a system capable of expressing the protein in a way that allows reporter molecule (or target molecule) binding and fluorescence sensitivity to the activity (if a reporter molecule) to be assayed. By isolating and identifying by selection methods the genetic sequence of the particular protein within the mutated population that functions optimally as a selectivity component.

In other embodiments, a library of mutants is generated from a degenerate oligonucleotide sequence. There are many ways by which the library may be generated from a degenerate oligonucleotide sequence. Chemical synthesis of a degenerate gene sequence may be carried out in an automatic DNA synthesizer, and the synthetic genes may then be ligated into an appropriate vector for expression. One purpose of a degenerate set of genes is to provide, in one mixture, all of the sequences encoding the desired set of potential protein sequences. The synthesis of degenerate oligonucleotides is well known in the art (see for example, Narang, S A (1983) Tetrahedron 39:3: Itakura et al., (1981) Recombinant DNA. Proc. 3rd Cleveland Sympos. Macromolecules, ed. A G Walton, Amsterdam: Elsevier pp. 273-289; Itakura et al., (1984) Annu. Rev. Biochem 53:323; Itakura et al., (1984) Science 198:1056; Ike et al. (1983) Nucleic Acid Res. 11:477). Such techniques have been employed in the directed evolution of other proteins (see, for example, Scott et al., (1990) Science 249:386-390; Roberts et al., (1992) Proc. Natl. Acad. Sci. USA 89:2429-2433; Devlin et al., (1990) Science 249: 404-406; Cwirla et al., (1990) Proc. Natl. Acad. Sci. USA 87: 6378-6382; as well as U.S. Pat. Nos. 5,223,409, 5,198,346, and 5,096,815).

Alternatively, other forms of mutagenesis may be utilized to generate a combinatorial library. For example, mutants may be generated and isolated from a library by screening using, for example, alanine scanning mutagenesis and the like, by linker scanning mutagenesis; by saturation mutagenesis; by PCR mutagenesis; or by random mutagenesis. Linker scanning mutagenesis, particularly in a combinatorial setting, is an attractive method for identifying activators.

In still other embodiments, the activator and/or selectivity component is an aptamer, also known as a nucleic acid ligand. Aptamers are oligonucleotides that are selected to bind specifically to a desired molecular structure. Aptamers typically are the products of an affinity selection process similar to the affinity selection of phage display (also known as in vitro molecular evolution). The process involves performing several tandem iterations of affinity separation, e.g., using a solid support to which the desired immunogen is bound, followed by polymerase chain reaction (PCR) to amplify nucleic acids that bound to the immunogens. Each round of affinity separation thus enriches the nucleic acid population for molecules that successfully bind the desired immunogen. In this manner, a random pool of nucleic acids may be "educated" to yield aptamers that specifically bind target molecules. Aptamers typically are RNA, but may be DNA or analogs or derivatives thereof, such as, without limitation, peptide nucleic acids and phosphorothioate nucleic acids. Aptamers, may be prepared using the "SELEX" methodology which involves selection of nucleic acid ligands which interact with a target in a desirable manner combined with amplification of those selected nucleic acids. The SELEX process, is described in U.S. Pat. Nos. 5,475,096 and 5,270,163 and PCT Application No. WO 91/19813. These references, each specifically incorporated herein by reference, are collectively called the SELEX Patents.

The SELEX process provides a class of products which are nucleic acid molecules, each having a unique sequence, and each of which has the property of binding specifically to a desired target compound or molecule. In various embodiments, target molecules may be, for example, proteins, carbohydrates, peptidoglycans or small molecules. SELEX methodology can also be used to target biological structures, such as cell surfaces or viruses, through specific interaction with a molecule that is an integral part of that biological structure.

The basic SELEX method has been modified to achieve a number of specific objectives. For example, U.S. Pat. No. 5,707,796 describes the use of the SELEX process in conjunction with gel electrophoresis to select nucleic acid molecules with specific structural characteristics, such as bent DNA. U.S. Pat. No. 5,580,737 describes a method for identifying highly specific nucleic acid ligands able to discriminate between closely related molecules, termed CounterSELEX. U.S. Pat. No. 5,567,588 describes a SELEX-based method which achieves highly efficient partitioning between oligonucleotides having high and low affinity for a target molecule. U.S. Pat. Nos. 5,496,938 and 5,683,867 describe methods for obtaining improved nucleic acid ligands after SELEX has been performed.

In certain embodiments, nucleic acid activator and/or selectivity components as described herein may comprise modifications that increase their stability, including, for example, modifications that provide increased resistance to degradation by enzymes such as endonucleases and exonucleases, and/or modifications that enhance or mediate the delivery of the nucleic acid ligand (see, e.g., U.S. Pat. Nos. 5,660,985 and 5,637,459). Examples of such modifications include chemical substitutions at the ribose and/or phosphate and/or base positions, in various embodiments, modifications of the nucleic acid ligands may include, but are not limited to, those which provide other chemical groups that incorporate additional charge, polarizability, hydrophobicity, hydrogen bonding, electrostatic interaction, and functionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications may also include 3' and 5' modifications such as capping. In exemplary embodiments, the nucleic acid ligands are RNA molecules that are 2'-fluoro (2'-F) modified on the sugar moiety of pyrimidine residues.

In one embodiment, the activator and/or selectivity component is a template imprinted material. Template imprinted materials are structures which have an outer sugar layer and an underlying plasma-deposited layer. The outer sugar layer contains indentations or imprints which are complementary in shape to a desired target molecule or template so as to allow specific interaction between the template imprinted structure and the target molecule to which it is complementary. Template imprinting can be utilized on the surface of a variety of structures, including, for example, medical prostheses (such as artificial heart valves, artificial limb joints, contact lenses and stents), microchips (preferably silicon-based microchips) and components of diagnostic equipment designed to detect specific microorganisms, such as viruses or bacteria. Template-imprinted materials are discussed in U.S. Pat. No. 6,131,580, which is hereby incorporated by reference in its entirety.

In certain embodiments, an activator and/or selectivity component contains a tag or handle which facilitates its isolation, immobilization, identification, or detection and/or which increases its solubility. In various embodiments, the tag may be a polypeptide, a polynucleotide, a carbohydrate, a polymer, or a chemical moiety and combinations or variants thereof. In certain embodiments, exemplary chemical handles, include, for example, glutathione S-transferase (GST); protein A, protein G, calmodulin-binding peptide, thioredoxin, maltose binding protein, HA, myc, poly arginine, poly His, poly His-Asp or FLAG tags. Additional exemplary tags include polypeptides that alter protein localization in vivo, such as signal peptides, type III secretion system-targeting peptides, transcytosis domains, nuclear localization signals, etc.

In another embodiment, a activator and/or selectivity component is modified so that its rate of traversing the cellular membrane is increased. For example, the activator may be attached to a peptide which promotes "transcytosis," e.g., uptake of a polypeptide by cells. The peptide may be a portion of the HIV transactivator (TAT) protein, such as the fragment corresponding to residues 37-62 or 48-60 of TAT, portions which have been observed to be rapidly taken up by a cell in vitro (Green and Loewenstein, (1989) Cell 55:1179-1188). Alternatively, the internalizing peptide may be derived from the *Drosophila* antennapedia protein, or homologs thereof. The 60 amino acid long homeodomain of the homeo-protein antennapedia has been demonstrated to translocate through biological membranes and can facilitate the translocation of heterologous polypeptides to which it-is coupled. Thus, activators may be fused to a peptide consisting of about amino acids 42-58 of *Drosophila* antennapedia or shorter fragments for transcytosis (Derossi et al. (1996) and J Biol Chem 271:18188-18193). The transcytosis polypeptide may also be a non-naturally-occurring membrane-translocating sequence (MTS), such as the peptide sequences disclosed in U.S. Pat. No. 6,248,558.

In still other embodiments, the activator and/or selectivity component is bivalent, comprising both an activator and selectivity component in one contiguous polypeptide sequence in the form of a fusion (chimeric) protein comprising any suitable polypeptide activator and selectivity component. As above, the fusion protein may comprise at least one domain which increases its solubility and/or facilitates its purification, identification, detection, targeting and/or delivery. Exemplary domains, include, for example, glutathione S-transferase (GST), protein A, protein G, calmodulin-binding peptide, thioredoxin, maltose binding protein, HA, myc, poly arginine, poly His, poly His-Asp or FLAG fusion proteins and tags. Additional exemplary domains include domains that alter protein localization in vivo, such as signal peptides, type III secretion system-targeting peptides, transcytosis domains, nuclear localization signals, and targeting moieties, i.e. proteins specific for a target molecule, etc. In various embodiments, a polypeptide of the invention may comprise one or more heterologous fusions. Polypeptides may contain multiple copies of the same fusion domain or may contain fusions to two or more different domains. The fusions may occur at the N-terminus of the polypeptide, at the C-terminus of the polypeptide, or at both the N- and C-terminus of the polypeptide. Linker sequences between an activator and/or selectivity component polypeptide may be included in order to facilitate construction of the fusion protein or to optimize protein expression or structural constraints of the fusion protein. Exemplary, proof of concept fusion proteins are described below.

Glycosylphosphatidylinisotol (GPI) anchored proteins are membrane bound proteins found throughout the animal kingdom. GPI anchored proteins are linked at their carboxy-terminus through a phosphodiester linkage of phosphoethanolamine to a trimannosyl-non-acetylated glucosamine (Man3-GlcN) core. The reducing end of GlcN is linked to phosphatidylinositol (PI). PI is then anchored through another phosphodiester linkage to the cell membrane through its hydrophobic region. GPI anchoring may be accomplished by including an appropriate signal, e.g., an Ala or Gly at the ω+2 position, though other signals will result in GPI anchoring. See, e.g., White et al. (2000) Comparison of the glycosyl-phosphatidylinositol cleavage/attachment site between mammalian cells and parasitic protozoa *Journal of Cell Science* 113, 721-727 (2000).

In other embodiments, the activator and/or selectivity component is expressed within the cell or organism or subject to be analyzed as a fusion protein (see the examples below). The expression methods described below may also be used to express an activator and selectivity component in a host cell that is then isolated and purified for use as described herein and as is know to those of ordinary skill in the relevant arts.

Generally, a nucleic acid encoding the activator and/or selectivity component can be introduced into a host cell, such as by transfection or infection, and the host cell is cultured under conditions allowing expression of the activator. Methods of introducing nucleic acids into prokaryotic and eukaryotic cells are well-known in the art. Suitable media for mammalian and prokaryotic host cell culture are well known in the art. In some instances, the nucleic acid encoding the subject polypeptide is under the control of an inducible promoter, which is induced once the host cells comprising the nucleic acid have divided a certain number of times. For example, where a nucleic acid is under the control of a beta-galactose operator and repressor, isopropyl beta-D-thiogalactopyranoside (IPTG) is added to the culture when the bacterial host cells have attained a density of about $OD_{600}$ 0.45-0.60. The culture is then grown for some more time to give the host cell the time to synthesize the polypeptide. Cultures are then typically frozen and may be stored frozen for some time, prior to isolation and purification of the polypeptide.

Thus, a nucleotide sequence encoding all or part of an activator and/or selectivity component may be used to produce a recombinant form of an activators and selectivity component via microbial or eukaryotic cellular processes. Ligating the sequence into a polynucleotide construct, such as an expression vector, and transforming, infecting, or transfecting into hosts, either eukaryotic (yeast, avian, insect or mammalian) or prokaryotic (bacterial cells), are standard procedures. Similar procedures, or modifications thereof, may be employed to prepare recombinant polypeptides by microbial means or tissue-culture technology in accord with the subject invention.

By "expression" it is meant the overall flow of information from a gene (without limitation, a functional genetic unit for producing a gene product, typically encoded on DNA or RNA, for some viruses, and comprising a transcriptional promoter, and other cis-acting elements, such as response elements and/or enhancers, an expressed sequence that typically encodes a protein (open-reading frame or ORF) or functional/structural RNA, and a polyadenylation sequence), to produce a gene product (typically a protein, optionally post-translationally modified or a functional/structural RNA). By "expression of genes under transcriptional control of," or alternately "subject to control by," a designated sequence, it is meant gene expression from a gene containing the designated sequence operably linked (functionally attached, typically in cis) to the gene. The designated sequence may be all or part of the transcriptional elements (without limitation, promoters, enhancers and response elements), and may wholly or partially regulate and/or affect transcription of a gene. A "gene for expression of" a stated gene product is a gene capable of expressing that stated gene product when placed in a suitable environment—that is, for example, when transformed, transfected of transduced into a cell, and subjected to suitable conditions for expression. In the case of a constitutive promoter "suitable conditions" means that the gene typically need only be introduced into a host cell. In the case of an inducible promoter, "suitable conditions" means when an amount of the respective inducer is administered to the expression system (e.g., cell) effective to cause expression of the gene. All nucleotide sequences described herein are provided in a 5'-to-3' direction and all amino acid sequences described herein are provided in an N-terminal-to-C-terminal direction.

Other embodiments of nucleic acid sequences encoding the activator and/or selectivity component, as well as vectors, host cells, cultures thereof, and methods of making fusion proteins are described below or in WO 2008/092041. A nucleic acid encoding an activator and/or selectivity componentcan be operably linked to a bacterial promoter, e.g., the anaerobic *E. coli*, NirB promoter or the *E. coli* lipoprotein lip; *Salmonella* pagC promoter, *Shigella* ent promoter, the tet promoter on TnIO, or the ctx promoter of *Vibrio cholera*. Any other promoter can be used. The bacterial promoter can be a constitutive promoter or an inducible promoter. A signal peptide sequence may be added to the construct, such that the activator is secreted from cells. Such signal peptides are well known in the art. In one embodiment, the powerful phage T5 promoter, that is recognized by E. coli RNA polymerase is used together with a lac operator repression module to provide tightly regulated, high level expression or recombinant proteins in E. coli. In this system, protein expression is blocked in the presence of high levels of lac repressor. A huge variety of methods and genetic constructs are available commercially and are otherwise known by or available to those of ordinary skill in the art, for production of recombinant proteins and polypeptides. In vitro protein synthesis using, e.g., eukaryotic lysates, such as rabbit reticulocyte lysates, rabbit oocyte lysates, human cell lysates, insect cell lysates and wheat germ extracts or even synthetic methods, as are broadly known, can be employed to produce the polypeptides described herein.

Plant expression vectors can be used. For example, viral promoters such as the 35S RNA and 19S RNA promoters of CaMV, or the coat protein promoter of TMV may be used; alternatively, plant promoters such as the small subunit of RUBISCO; or heat shock promoters, e.g., soybean hsp 17.5-E or hsp 17.3-B may be used. These constructs can be introduced into plant cells using Ti plasmids, Ri plasmids, plant virus vectors; direct DNA transformation; microinjection, electroporation, etc. For reviews of such techniques see, for example, Weissbach & Weissbach, 1988, Methods for Plant Molecular Biology., Academic Press, New York, Section VIII, pp. 421-463; and Grierson & Corey, 1988, Plant Molecular Biology, 2d Ed., Blackie, London, Ch. 7-9. Alternately, insect systems can be employed to produce the polypeptides described herein. In one such system, *Autographa californica* nuclear polyhedrosis virus (AcNPV) is used as a vector to express foreign genes. The virus grows in *Spodoptera frugiperda* cells. (see, e.g., Smith, U.S. Pat. No. 4,745,051). In another embodiment of an insect system, the DNA encoding the subject polypeptide is cloned into the pBlueBacIII recombinant transfer vector (Invitrogen, San Diego, Calif.) downstream of the polyhedrin promoter and transfected into Sf9 insect cells (derived from *Spodoptera frugiperda* ovarian cells, available from Invitrogen, San Diego, Calif.) to generate recombinant virus. In another embodiment, the subject polypeptides are prepared in transgenic animals, such that in certain embodiments, the polypeptide is secreted, e.g., in the milk of a female animal.

Viral vectors as are broadly known in the relevant arts, many of which are available commercially, may also be used for efficient in vitro introduction of a nucleic acid into a cell. Infection of cells with a viral vector has the advantage that a large proportion of the targeted cells can receive the nucleic acid. Additionally, polypeptides encoded by genetic material in the viral vector, e.g., by a nucleic acid contained in the viral vector, are expressed efficiently in cells that have taken up viral vector nucleic acid. Examples of useful viral vector systems include retrovirus, adenovirus and adeno-associated virus vectors are generally understood to be useful for the transfer of exogenous genes in vivo, particularly into mammals. These vectors provide efficient delivery of genes into cells, and the transferred nucleic acids typically are stably integrated into the chromosomal DNA of the host (see Miller, A. D. (1990) Blood 76:271). In one example, lentiviral vectors are used to produce transgenic animals by transduction of single-cell mouse and rat embryos (Carlos Lois, et al. Germline Transmission and Tissue-Specific Expression of Transgenes Delivered by Lentiviral Vectors, Science 295, 868 (2002); DOI: 10.1126/science.1067081).

Another viral gene delivery system utilizes adenovirus-derived vectors. Suitable adenoviral vectors derived from the adenovirus strain Ad type 5 dl324 or other strains of adenovirus (e.g., Ad2, Ad3, Ad7, etc.) are well known to those skilled in the art. Recombinant adenoviruses can be advantageous in certain circumstances in that they are capable of infecting non-dividing cells and can be used to infect a wide variety of cell types, including airway epithelium, endothelial cells, hepatocytes and muscle cells. Furthermore, the virus particle is relatively stable and amenable to purification and concentration, and, as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors. Most replication-defective adenoviral vectors currently in use and therefore favored by the present invention are deleted for all or parts of the viral E1 and E3 genes but retain as much as 80% of the adenoviral genetic material. Expression of the inserted genetic material can be under control of, for example, the E1A promoter, the major late promoter (MLP) and associated leader sequences, the E3 promoter, or exogenously added promoter sequences.

Yet another viral vector system useful for delivery of genetic material encoding the subject polypeptides is the adeno-associated virus (AAV). Adeno-associated virus is a naturally occurring defective virus that requires another virus, such as an adenovirus or a herpes virus, as a helper virus for efficient replication and a productive life cycle. It is also one of the few viruses that may integrate its DNA into non-dividing cells, and exhibits a high frequency of stable integration. Vectors comprising as little as 300 base pairs of AAV can be packaged and can integrate. Space for exogenous DNA is limited to about 4.5 kb. An AAV vector such as that described in Tratschin et al. (1985) Mol. Cell. Biol. 5:3251-3260 can be used to introduce DNA into cells. A variety of nucleic acids have been introduced into different cell types using AAV vectors (see, for example, Hermonat et al. (1984) Proc. Natl. Acad. Sci. USA 81:6466-6470 and Flotte et al. (1993) J. Biol. Chem. 268:3781-3790). Other viral vector systems may be derived from herpes virus, vaccinia virus, and several RNA viruses.

In addition to viral transfer methods, such as those illustrated above, non-viral methods can also be employed to cause expression of nucleic acids encoding the subject polypeptides, e.g. in a cell in vitro or in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of genetic material by the targeted cell. Exemplary gene delivery systems of this type include liposomal derived systems, polylysine conjugates, and artificial viral envelopes. For example, genetic material can be entrapped in liposomes bearing positive charges on their surface (e.g., lipofectins) and, optionally, which are tagged with antibodies against cell surface antigens of the target tissue (Mizuno et al. (1992) No Shinkei Geka 20:547-551; PCT publication WO91/06309; Japanese patent application 1047381; and European patent publication EP-A-43075). For example, lipofection of papilloma-infected cells can be carried out using liposomes tagged with monoclonal antibodies against PV-associated antigen (see Viae et al. (1978) J Invest Dermatol 70:263-266; see also Mizuno et al. (1992) Neurol. Med. Chir. 32:873-876).

The gene delivery system comprises an antibody or cell surface ligand which is cross-linked with a gene binding agent such as polylysine (see, for example, PCT publications WO93/04701, WO92/22635, WO92/20316, WO92/19749, and WO92/06180). For example, genetic material encoding the subject chimeric polypeptides can be used to transfect hepatocytic cells in vivo using a soluble polynucleotide carrier comprising an asialoglycoprotein conjugated to a polycation, e.g., polylysine (see U.S. Pat. No. 5,166,320). It will also be appreciated that effective delivery of the nucleic acid constructs via mediated endocytosis can be improved using agents which enhance escape of the gene from the endosomal structures. For instance, whole adenovirus or fusogenic peptides of the influenza HA gene product can be used as part of the delivery system to induce efficient disruption of DNA-comprising endosomes (Mulligan et al. (1993) Science 260-926; Wagner et al. (1992) Proc. Natl. Acad. ScL USA 89:7934; and Christiano et al. (1993) Proc. Natl. Acad. Sci. USA 90:2122).

In one embodiment, a gene encoding an activator of the acceptor is expressed in a cell of interest. In one embodiment, the activator is expressed on the surface of a cell of interest. For example, a gene encoding an activator is transferred into a cell such that the activator is expressed in the cell or is targeted to expression on the cell surface. Invitrogen's pDisplay facilitates expression of proteins on a cell surface. The proteins are fused at their N-terminus to the murine Ig K-chain leader sequence, which directs the protein to the secretory pathway, and at the C-terminus to the platelet derived growth factor receptor (PDGFR) transmembrane domain, which anchors the protein to the plasma membrane, displaying it on the extracellular side. Other combinations of leader sequences and anchors are known in the art and can substitute for those of the pDisplay construct. pDisplay contains a constitutive promoter, the human cytomegalovirus (CMV) immediate-early promoter/enhancer. Other constitutive promoters may be substituted for the CMV promoter. As can be appreciated by those of ordinary skill in the art, a gene construct comprising a promoter, a coding sequence, and a polyadenylation sequence, such as the bovine growth hormone (BGH) polyadenylation sequence can be propagated by any suitable vector, including plasmids, phage, virus, cosmid, etc. Further, the gene can be inserted into any suitable delivery vector, such as the lentivirus, adenovirus, AAV, vectors described above.

In certain embodiments, it will be desirable to express the activator in a tissue-specific manner. A large number of human, mouse, rat and other tissue-specific promoters are known. For example, constructs comprising tissue-specific promoters for human (see, FIG. 3), rat or mouse astrocytes, human neurons (see, e.g., FIG. 4) and mature rat neurons are available commercially from Invivogen, San Diego, Calif.

The glial fibrillary acidic protein (GFAP) is an intermediate filament protein found almost exclusively in astrocytes. It is expressed throughout postnatal life and is upregulated in response to almost any damage to the central nervous system, including Parkinson's disease. The promoter of the GFAP gene was shown to direct astrocyte-specific transcription in vitro, in vivo [Vandier et al. 2000. Inhibition of glioma cells in vitro and in vivo using a recombinant adenoviral vector containing an astrocyte-specific promoter. Cancer Gene Ther 7:1120-6], and in transgenic mice [Brenner et al. 1994. GFAP promoter directs astrocyte-specific expression in transgenic mice. Neurosci. 14:1030-7]. Expression of a transgene under the control of the GFAP promoter is regulated in a similar fashion as the endogenous GFAP gene [Jakobsson J. et al., 2004. Lesion-dependent regulation of transgene expression in the rat brain using a human glial fibrillary acidic protein-lentiviral vector. Eur J Neurosci. 19(3):761-5].

Synapsin I is a neuron-specific phosphoprotein that coats the cytoplasmic surface of small synaptic vesicles. The proximal region of the synapsin I promoter (−422 to −22) is sufficient to direct neuron-specific gene expression. Neuron specificity is conferred by a putative binding site for the zinc finger protein, neuron-restrictive silencer factor/RE-1 silencing transcription factor (NRSF/REST). The NRSF/REST protein, which is expressed only in non-neuronal cells, represses the activity of constitutive enhancers thus silencing the expression of synapsin I in non-neuronal cells [Schoch S. et al., 1996. Neuron-specific gene expression of synapsin I. Major role of a negative regulatory mechanism. J Biol Chem. 271(6):3317-23]. The synapsin I promoter has been used to achieve highly neuron-specific long-term transgene expression in vivo [Kugler S. et al., 2003. Human synapsin 1 gene promoter confers highly neuron-specific long-term transgene expression from an adenoviral vector in the adult rat brain depending on the transduced area. Gene Ther. 10(4):337-47].

One non-limiting method of preparation of transgenic animals expressing genes for expression in a tissue-specific manner is use of mice expressing Cre recombinase under control of a tissue-specific promoter, which can be crossed with a loxP-FAP mouse to produce animals with tissue-specific FAP expression by recombination, as are commercially available.

According to certain embodiments of the biosensors described herein, certain functional goals are desirable.

In one aspect, the design goal is a low fluorescence of the acceptor linked to the activator (e.g., FAP) or donors. The acceptor fluorogen is attached to the donor using appropriate chemical reactions and linker(s). The fluorescence of the construct is tested in cell extracts and purified nucleic acid materials for background fluorescence under the conditions that would be used to detect the composition. If the fluorescence activation is high, modifications of the acceptor charge, size, and hydrophobicity can be utilized to decrease the nonspecific interactions in a cellular context.

Malachite green can serve as an acceptor, as we already have selected modules that activate it with switching ratios of >15,000 fold in buffer. Additional fluorogens may be designed and synthesized. Unsymmetric polymethine dyes, and analogs of indocyanine green may be used as fluorogens, as can many of the polarity sensing dyes (e.g. merocyanine and styryl dyes) with far-red and near IR emission. Fluorogens are screened for nonspecific activation in cell lysate before incorporation into the biosensor composition. Quenching and activation by selected FAP modules are characterized in buffer and cell lysate to determine the activation ratio. FAP/biosensor pairs with acceptable switching ratios are characterized by FCS and TIRF-single molecule microscopy.

According to certain embodiments, novel fluorogen activating peptides are isolated using methods that were established for the initial selections of fluorogen activating peptides from the yeast surface display library. Briefly, biotinylated versions of each fluorogen that have been synthetically prepared will be incubated with an expanded, induced aliquot of the Pacific Northwest National Laboratory yeast surface displayed scFv library (~$10^9$ distinct clones, $10^{11}$ cells for selection). Yeast that bind to the biotinylated dye are magnetically enriched in two steps, first with streptavidin conjugated magnetic bead, followed by expansion and a second round of enrichment with anti-biotin conjugated magnetic beads. These yeast are eluted from the beads, and then incubated with free dye (if amenable to direct detection on the flow cytometer—if not, biotinylated dye followed by a wash and streptavidin Alexa 488 labeling), and flow sorted to select a population of cells that are fluorogenic or that bind to the fluorogen. Fluorogenic clones not detectable on the cytometer can be detected by washing dye over an agar plate containing isolated induced colonies, and selecting the brightest colonies using a wide-field fluorescence imaging system for subsequent analysis. It was found that clones recovered from the library have a range of affinities and spectral properties, and that subsequent affinity maturation (by error-prone PCR) can result in changes in affinity, quantum yield, and selectivity. Clones are easily transferred from the surface display system to a yeast secretion system using established protocols. Promising clones can be sequenced, and unique clones are transferred to the pPNL9 secretion vector to produce protein for subsequent characterization of the ensemble and single molecule fluorescence and binding properties with the fluorogen.

Biosensors are synthesized by any useful method. According to one embodiment, once a given fluorogen acceptor and activator pair are identified, the fluorogen acceptor is attached to an environment-sensitive donor. In one example, a linker is attached to the acceptor and environment-sensitive donor by standard linking methods. A synthetic strategy builds biosensors by linker addition to a fluorogen. The resulting intermediates are a series of fluorogenic pre-biosensors. These amines can be easily reacted with active esters of donor dyes. One advantage of this strategy is that a number of distinct donor fluorophores can be tested with each pre-biosensor, to determine which fluorophores have the most efficient energy transfer, show the lowest propensity for dye aggregation or nonspecific binding. For acetylenic malachite green, DIR (dimethylindole red) and the MG fluorogens, the Forster radius is comparable, and the direct intramolecular FRET approach is likely to be similarly successful to the results shown for MG biosensors. In the case of indocyanine green, however, the Forster radius is considerably shorter, and the overall FRET efficiency is likely to be reduced. If this is the case, a cascade approach with a mediator dye may be utilized to ensure efficient FRET from the donors, and efficient FRET to the acceptors. In this case, the cy5-icg tandem, or other far-red dye, near infrared chromophore tandem pair may serve as the "starting fluorogen".

Fluoromodule Optimization and Maturation. The properties of the fluorogen activating peptides selected against fluorogen alone are not necessarily optimized for binding and activation of the fluorogenic biosensors. A reduction of the affinity of clones on addition of donor dyes to a previously selected fluorogen may arise in certain circumstances. According to one example, to refine the properties of these FAPs specifically for binding and activating fluorogenic biosensors, affinity maturation of fluorogen binding clones with high quantum yields and tight binding is carried out by error-prone PCR methods, and the resulting library of mutants is selected for binding and activation of the complete biosensor, rather than the parent fluorogen. Clones that are capable of binding and activating fluorogenic biosensor at low concentration, and with high quantum efficiency, as determined by flow cytometry (ratio of expression measured with an HA epitope tag to measured brightness of the fluorogen provides a value that correlates to clone quantum yield) are collected and sequenced.

The biosensors and biosensor systems described herein, and are useful for virtually any assay, imaging system that a fluorogen is useful for. As described in detail herein, the biosensors are useful in real-time imaging in cells or an organism. As an example, an activator/selectivity component-containing polypeptide is introduced into a cell by any means, including genetically, by transient or permanent transfection, transduction or transformation of a cell or organism with a nucleic acid comprising a gene for expressing the polypeptide. Alternately, the polypeptide is introduced into a cell or organism. A fusion protein or complex comprising the activator and selectivity component, such as an antibody, can be used for in situ assays of, for example, fixed cells or tissue. In such an embodiment, the selectivity component is bound to a cell or tissue component, such as a protein, of a cell or tissue, and the activator binds the biosensor, such that the desired cell or tissue component can be localized in the cell or tissue. An activator bound to a selectivity component in a complex or as a fusion protein also can be used in a fluorescent assay akin to an ELISA or RIA, e.g., in a sandwich-type assay. Likewise, a probe comprising the activator and a selectivity component, such as an antibody or a nucleic acid, can be used in detection of a protein or nucleic acid in a western, northern or Southern blot or EMSA, or other electrophoresis methods.

Methods of using the biosensors and biosensor complexes are described above. These methods utilize any biosensor described herein, so long as they function for the described purpose. In one embodiment, an environmental sensing method for detecting the presence of and analyte or for quantifying the analyte is provided. The method comprises, first, contacting a biosensor, according to any embodiment described herein, with an activator. In one embodiment, the biosensor comprises an activatable acceptor fluorogen linked by a linker to an environment-sensitive donor that interacts with an analyte. In this embodiment, the activatable acceptor fluorogen produces a fluorescence signal increase of at least 100-fold when it interacts non-covalently with the activator as compared to when no activator is present and the environment-sensitive donor transfers excitation energy to the activatable acceptor fluorogen such that, when activated, the activatable acceptor fluorogen produces a detectable fluorescent signal when the environment-sensitive donor is excited and the environment-sensitive donor transfers different amounts of excitation energy to the activatable acceptor fluorogen when it interacts with the analyte as compared to when no analyte is present. The method further comprises illuminating the biosensor with light of a wavelength overlapping an excitation spectrum of the environment-sensitive donor, but not overlapping the excitation spectrum of the activatable acceptor fluorogen and measuring emissions from the activatable acceptor fluorogen. The method may further comprise, as a control, after contacting the biosensor with the activator, illuminating the biosensor with light of a wavelength overlapping an excitation spectrum of the activatable acceptor fluorogen, but not overlapping an excitation spectrum of the environment-sensitive donor and measuring emissions from the activatable fluorogen. The activator optionally comprises a selectivity component, e.g., a linked ligand moiety, for example an antibody, antibody fragment, scFv, that binds to its binding partner, such as a cell-surface protein, or CD (cluster of differentiation) antigen. As a non-limiting example, selectivity component binds to an epitope, a protein, a modified protein, a nucleic acid, a nucleotide sequence, a small molecule (non-polymeric and less than 800 Daltons), an active agent (e.g., a drug or other compound having a physiological effect), an antibody, a cell, a cell-surface marker, a tissue, a site in an array or a particle by the selectivity component.

The method may be self-calibrating or pre-calibrated. In either case, the method further comprises comparing the measured emissions from the activatable acceptor fluorogen to a control sample or to control sample data to determine the presence of or to quantify amounts of the analyte. As indicated above, This refers to two different scenarios. In the first, a test sample and one or more control samples are analyzed side-by-side, and the test sample is compared to the control samples.

In a second scenario, the controls are run to calibrate the analytical system, and results measured with individual test samples are compared to the calibration results to identify or quantify the analyte tested. Persons performing such analysis are capable of determining testing and calibration conditions suitable for each analytic activity. Any useful comparison method, whether computer-based or not, may be used to compare the test sample results to the calibration control.

The following Examples are provided for illustrative purposes only and are not intended to limit the contemplated scope of the invention.

Example 1—Synthesis of Calcium-Sensitive Rhod2 Derivative

In initial studies, CY3 was linked to the malachite green fluorogen through a short spacer, and the fluorescence from the CY3 was completely quenched in solution. Subsequent binding of this reagent resulted in bright fluorescence from the malachite green under both CY3 and MG excitation wavelengths, and essentially no detectable fluorescence from the CY3 directly (FIG. 5). Here, this intramolecular energy transfer mechanism will be used for local activation of fluorescent environmental probes of calcium concentration.

A fluorogen-quenched Rhod-2 derivative that is sensitive to Ca in the millimolar range ($K_d$=1 mM) is synthesized as a cell-impermeant molecule (See Examples 7 and 8, below), to facilitate studies of the apical epithelial surface. The affinity of this molecule for the available MG-binding FAPs is characterized by solution fluorescence titration, and the dose dependent calcium response is evaluated in the presence and absence of excess protein (above the measured fluorogen $K_d$) to characterize both sensitization and activation of the bound probe under physiological $Ca^{2+}$ levels. This reagent will significantly improve on existing calcium sensor reagents, because excitation of the probe with MG excitation (633 or 645 nm) will provide a measure of the local probe concentration, while excitation of the Rhod-2 (561 or 532 nm) will provide a measure of the local calcium, resolving the classical problem of whether a change in intensity is a brightness or concentration enhancement effect.

The synthetic pathway leading to the MG-Rhod-2 conjugate starts with the synthesis of Rhod-2 bearing a linker on the chelating moiety. Commercial 2-Nitrophenol I is alkylated with bromo-ethanol to give II. Activation of the alcohol with tosyl chloride, and reaction with commercial 3-nitro-3-hydroxy-benzaldehyde III, give IV. Wittig Reaction of IV with tert-butoxycarbonylmethylene-triphenylphosphorane transforms the aldehyde into a linker side for the MG coupling. Simultaneous reduction of the nitro groups and the alkene side chain (Pt/$H_2$/Parr Hydrogenator) will result in VII. The chelating moieties are introduced by alkylation with bromomethylacetate. Vilsmeier formylation leads to the BAPTA aldehyde VIII. This aldehyde is condensed with 3-dimethylaminophenol, then oxidized to give the rhodamine dye. The tert-butylester of the side chain can be selectively cleaved to give IX. After coupling of Rhod-2 to MG-PEG-amine, the methyl esters of the chelator moieties are cleaved in the final step to give the target compound X.

Figure 6:
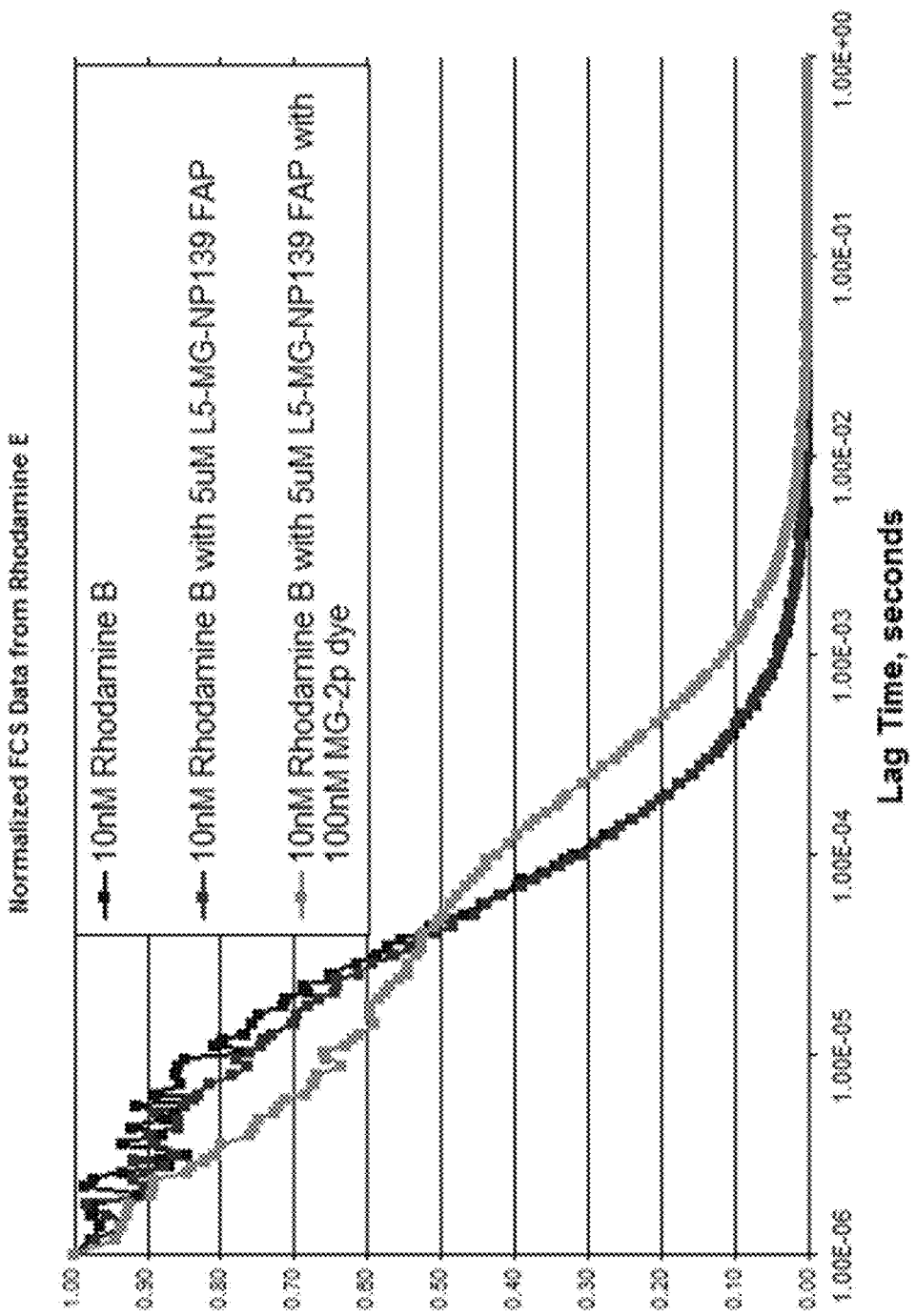
FIG. 6 shows a fluorescence correlation spectroscopy (FCS). This demonstrates that rhodamine B (structurally similar to the Rhod2 Calcium Sensor) neither binds to nor inhibits normal binding of a malachite green binding FAP clone.

To assess the feasibility of this approach, two key criteria have been met. First, the spectral properties of Rhod-2 are almost identical to the CY3 that has already been used as a successful donor molecule. Second, the rhodamine moiety, which is structurally similar to malachite green, has been shown not to bind or block binding of the MG-binding FAP module. Fluorescence correlation spectroscopy (FCS) was used to demonstrate that rhodamine B in solution diffuses as a free small molecule, even in the presence of a 500-fold molar excess of protein. This indicates that the dye does not associate with the malachite green binding clone, a critical requirement for appropriate sensor function. In addition, the FCS of this sample with added MG dye showed a characteristic shift in diffusion coefficient, reflecting the FAP-MG complex (FIG. 6). These findings support the design of this probe.

Example 2—Voltage-Sensitive Dyes

Voltage sensitive dyes have been used with optical imaging to visualize action potentials in neural systems for nearly 40 years. This technology holds enormous potential for mapping electrical connections and activity in neurological tissues. Recent advances have provided high speed cameras that can resolve millisecond action potentials from cells in a stained region and new two-photon imaging methods can resolve optical voltage signals from deeper in tissues. However, there are two major barriers that must still be overcome to realize the power of this technology. One major problem is that currently available voltage sensitive probes, which diffuse to all cells in the brain tissue, result in optical signals from all excitable cells that have been stained. In an intact brain, such complete network activity does not allow selective monitoring of cell type-specific networks that drive distinct behaviors. The second problem is that high background fluorescence from stained tissue provides additional loss of detection sensitivity. If there were a way to target both the fluorescence signal and the voltage sensing probe itself selectively to cells of interest, the field of optical neurobiology would be revolutionized. But currently no robust probe technology enables genetically targeted voltage sensing. A new tool is provided to allow neurobiologists to target and activate the best dye-based voltage sensitive probes at sites and networks of interest in the brain.

Figure 7:
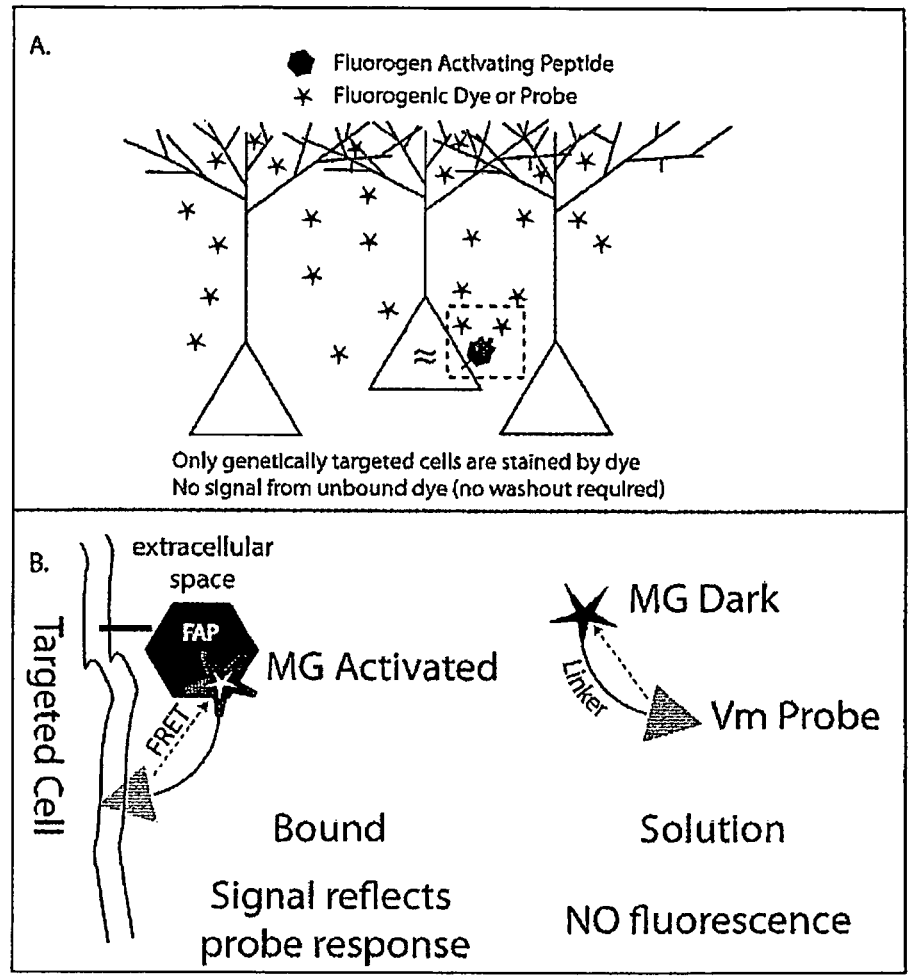
FIG. 7 presents a schematic of the Activation by Targeting (AbT) probe technology. A. Only genetically targeted cells are capable of producing signal by binding dye, resulting in a washless procedure for labeling tissues. B. A zoomed region shows the difference between free probe and bound probe, where only bound probe gives detectable signal related to the probe response at the FAP site.

Targeting voltage sensitive probe signals specifically to cells of interest requires development of several components that work together. The cells of interest must first be targeted by inserting a genetic sequence into the cells that causes expression on the surface of these cells a targeting protein called a fluorogen activating peptide (FAP). The expressed FAP molecules, present only on the targeted cells, have the capability of tightly binding a diffusible probe molecule containing the voltage sensitive dye that has been subsequently added to the brain tissue. This scheme is illustrated in FIG. 7.

Notice that the diffusible probe has a Malachite Green chromophore (MG) attached through a flexible linker to the voltage sensing dye. The MG provides for high affinity binding of the probe to the FAP, which should effectively concentrate the probe to the targeted cell. The MG also provides a remarkable mechanism for assuring that the detected fluorescence signals arise only from FAP targeted probes on the cells of interest. In this mechanism, the illuminated voltage sensitive dye inserted in the membrane transfers its excitation to the MG that is bound to the targeting FAP through intramolecular Förster Resonance Energy Transfer (FRET) with a voltage dependent efficiency. This occurs instantaneously in the probe molecule because it reflects a voltage dependent change in spectral properties, rather than a voltage dependent change in distance (as is typical in fluorescent protein based FRET sensors). It is therefore the targeted MG fluorescence signal elicited by the excited voltage probe that reflects the cell activity. Significantly, all MG that is not bound to targeted cell is not fluorescent, and therefore, the new technology removes background signal, regardless of where the voltage probe locates in the neural tissue.

Synthesis of the Voltage Sensitive Probes.

Figure 8:
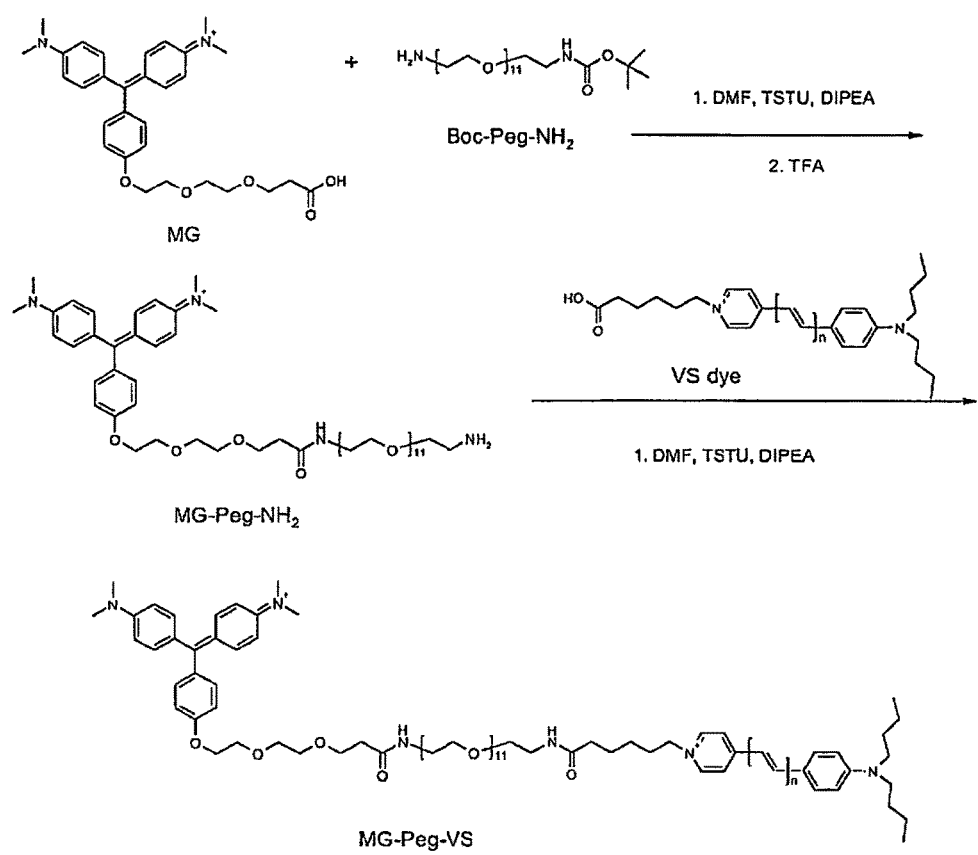
FIG. 8 demonstrates the modular synthesis of a Styryl Vm Dye through a PEG linker to MG. Importantly, it is straightforward to modify the PEG linker, or to modify the Voltage Sensing dye in this synthetic route, for rapid screening of promising probes.

There are a number of well-characterized voltage dyes such as Merocyanine XVII, Oxonol RH155, styryl Di4-ANEPPS, ANNINE-6 and Oxonol XXV that can be placed at the Vm location of the probe. These sensitive probes will be modified with a 2-20 unit polyethylene glycol (PEG) linker (so that the Vm Dye can reach the membrane, and yet transfer energy effectively to the MG) that has MG on the end as shown in FIG. 8. One of the advantages we bring is our experience developing near infrared fluorescing Vm Dyes. It has been shown that electrical activity can be imaged at a greater depth in tissues using long wavelength fluorescence from dyes we have developed such as Pgh1.

Testing of New Vm Probes:

The newly synthesized probes are characterized for fluorogenic activation and voltage response by spectroscopic and biochemical methods. The key challenge is to design a probe that retains the properties of both the fluorogen and the voltage dye, remaining optically dark until bound to a FAP, yet still partitioning appropriately into membranes and responding effectively to voltage changes. These properties can be optimized by control of linker length, and optimization of the pendant chains off of the respective dyes: both synthetic approaches are easily implemented. Successful probes are tested in cultured cells that have been transfected to produce FAP surface expression. Optical detection with voltage clamped membrane potential changes will allow us to quantify the optical sensitivity as a function of the surface density of FAP expression and the amount of probe in the bathing medium. The temporal response of these probes is assessed in both vesicle and cell-based clamping experiments. However, because the probes are based on fast-responding dye-based voltage sensors, the response time is expected to be comparable, and therefore suitable for measurements of single action potentials in vivo.

Success in these prototype probes would enable us to develop further sensors that have fluorogens that are spectrally and structurally distinct from MG. This would allow investigators to target several specific classes of neurons and examine communication among those neurons by high speed optical imaging. In principle, such an approach could visualize a single action potential propagating through a single synapse, for example labeling a presynaptic cell with one probe, and the postsynaptic cell with another, by distinct genetic targeting domains in the two cell types.

Example 3—Synthesis of the pH Sensitive Probes

Figure 9A:
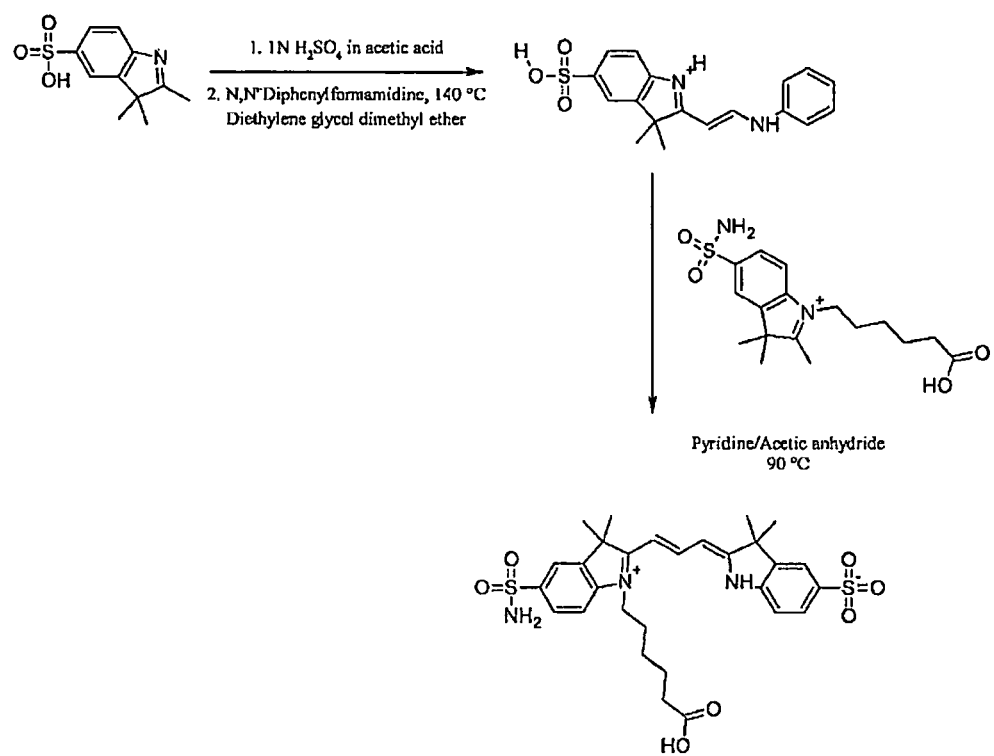
FIGS. 9A and 9B illustrate the synthesis of a pH dependent probe (CY3SApH-MG).
Figure 9B:
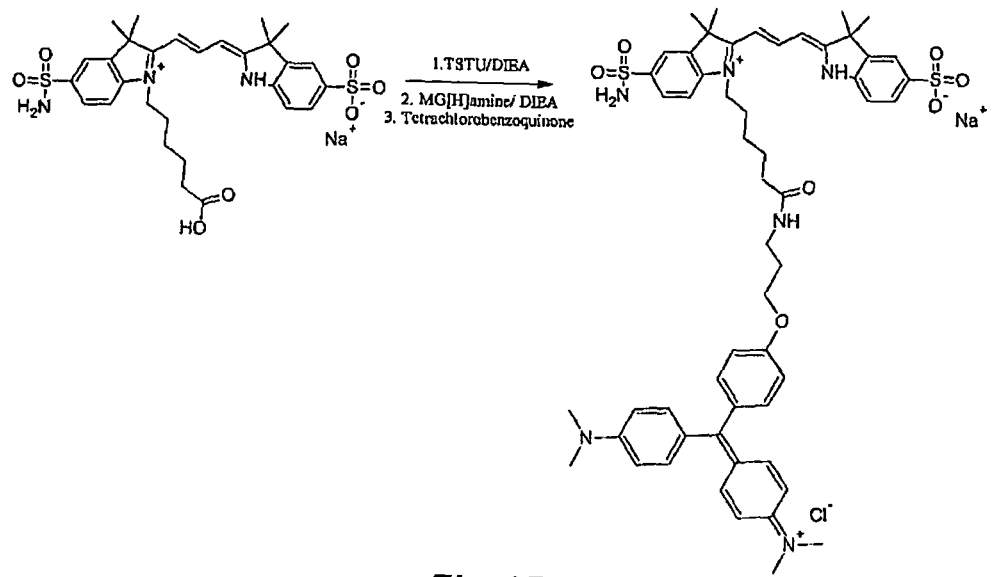

A pH sensitive probe, CY3SApH-MG, was prepared as described in FIGS. 9A and 9B. In reference to FIG. 9A, 2,3,3-Trimethyl-3H-indole-5-sulfonic acid (240 mg, 1 mmol) was dissolved at 60 C in 1 mL of 1 M sulfuric acid in acidic acid. N,N'Diphenylformamidine (590 mg, 3 mmol) dissolved in 3 mL of diethylene glycol dimethyl ether was added. The reaction mixture was heated to 140 C for 2 hrs. After cooling to rt the precipitate was filtered off. The solid was suspended in hot glacial acidic acid (10 mL) and hot filtered yielding the half-dye in 95% yield.

$^1$H-NMR (MeOD/1 drop NaOD): 7.69 (3H m, 1H bridge, 2H indolenine ring), 7.38 (1H, d, 2H indolenine ring), 7.30 (2H, m, phenyl ring), 7.10 (2H, m, phenyl ring), 7.0 (1H, t, phenyl ring), 5.39 (1H, d, bridge), 1.31 (6H, s, indolenine methyl groups).

Figure 9C:
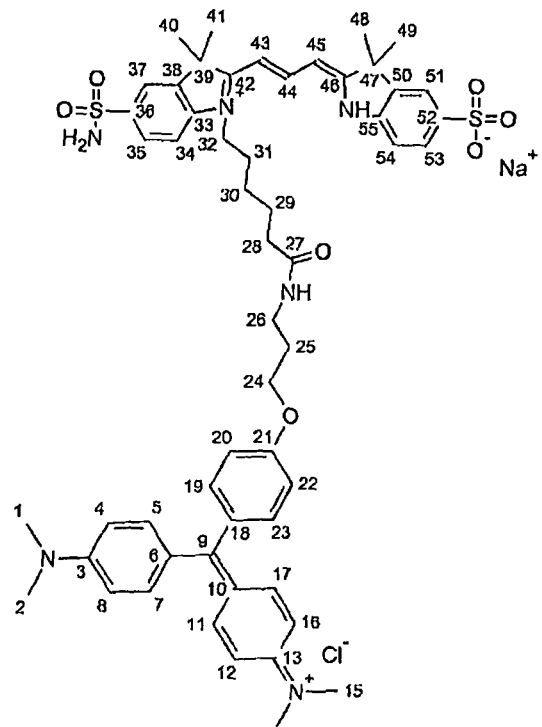
Figure 9E:
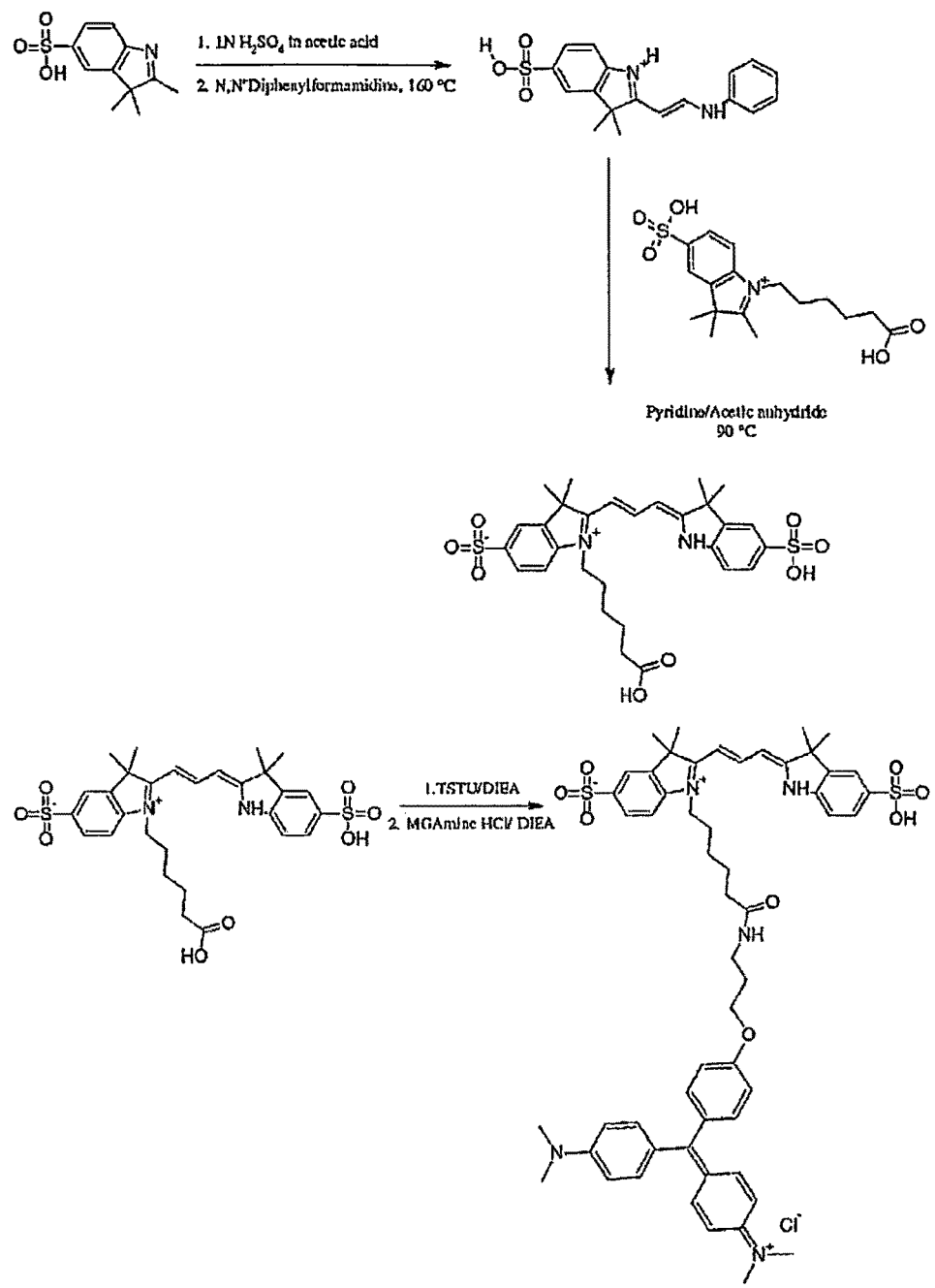
FIG. 9E illustrates the synthesis of CY3SApH-MG.

1-(6-Carboxypentyl)-2,3,3-trimethylindoleninium sulfonamide (354 mg, 1 mmol) was added and the mixture was dissolved in 4 ml of a 1:1 mixture of pyridine/acetic anhydride. The reaction mixture was heated to 90 C under stirring for 1 hr. The reaction mixture was dropwise added to ether (20 mL). The precipitate was dissolved in 20% ethanol/water adding 1 N sodium hydroxide until the color changed from red to orange. The dye was purified by MPLC on RP-18, eluent: ethanol/water/0.1% ammonia. $C_{29}H_{36}N_3O_6S_2$ MW: 602.7 g/mol. Yield: 210 mg/35%. In reference to FIG. 9B, CY3 pH in its basic form (60 mg, 0.1 mmol) was dissolved in 1 mL of dry DMF. TSTU (36 mg, 0.1 mmol) was added followed by DIEA (0.0175 ml, 0.1 mmol). The reaction mixture turns deep yellow and back to red as the active ester forms. After 1 hr at rt MG[H]amine (40 mg, 0.1 mmol) dissolved in 1 ml of dry acetonitrile was added followed by DIEA (0.0175 ml, 0.1 mmol). The reaction mixture was stirred at rt overnight. The solvent was removed under reduced pressure. The residue was washed with ethylacetate followed by acetonitrile to remove any unreacted MG[H] amine. The crude product was oxidized by dissolving it in a mixture of acetonitrile/methanol and adding dropwise under reflux a solution of tetrachlorobenzoquinone (25 mg, 0.01 mmol) dissolved in hot acetonitrile. The reaction mixture was refluxed for one hour. The solvent was removed and the residue was taken up in acetonitrile/water adding 1N sodium hydroxide until the color changed from purple to yellowish green. The mixture was separated by MPLC on RP-18, eluent: acetonitrile 1/water/0.1% ammonia. $C_{55}H_{65}N_6O_7S_2^+Cl^-$ Theor:MW: 986.27+/1021.72 g/mol, MS$^+$: 985.5/986.3/987.3 MS-Na: 1007.5/1008.5/1009.4 (See FIGS. 9C and 9D).

pH sensitive probe, CY3.29SApH-MG, was prepared as described in FIG. 9E, 2,3,3-Trimethyl-3H-indole-5-sulfonic acid (240 mg, 1 mmol) was dissolved at 60 C in 1 mL of 1 M sulfuric acid in acidic acid. N,N'Diphenylformamidine (393 mg, 2 mmol) was added. The reaction mixture was heated to 140° C. for 3 hrs. The temperature was raised to 160° C. and kept for 30 min. The residue was cooled to rt and dissolved in a minimum amount of methanol. The methanol solution was added drop wise into 100 mL of ethyl acetate causing the product to precipitate. The suspension was heated to reflux and hot filtered. The precipitate was washed with hot ethyl acetate and dried under vacuum. 1-(6-Carboxypentyl)-2,3,3-trimethylindoleninium (354 mg, 1 mmol) was added and the mixture was dissolved in 4 ml of a 1:1 mixture of pyridine/acetic anhydride. The reaction mixture was heated to 90° C. under stirring for 1 hr. The reaction mixture was drop wise added to 100 mL of ethyl acetate causing the product to precipitate. The precipitate was dissolved in 10 ml of 0.5 M HCl and purified by medium pressure chromatography on a RP-18, 150 mm×960 mm column, eluent: water/ethanol step gradient 0-10 min 0%, 10-20 min 10%, 20-35 min 15%, 35-50 min linear gradient 15-100%. $C_{29}H_{34}N_2O_8S_2$ MW: 602.7 g/mol. Yield: 105 mg (17%) MS$^+$601.3.

$^1$H-NMR (D2O) 8.34 (1H, m), 7.76 (1H, s), 7.74 (1H, d), 7.70 (1H, s), 7.60 (2H, d), 7.19 (1H, d), 7.10 (1H, d), 6.16 (1H, d), 5.99 (1H, m), 3.87 (2H, t), 2.17 (2H, t), 1.60 (2H, m), 1.53 (6H, s), 1.43 (2H, m), 1.30 (6H, brs), 1.21 (2H, m).

CY3 pH (30 mg, 0.05 mmol) was dissolved in 0.5 mL of dry DMF. TSTU (30 mg, 1 mmol) was added followed by DIEA (0.175 ml, 1 mmol). The reaction mixture turns deep yellow and back to red as the active ester forms. After 1 hr at RT MG-amine hydrochloride (22 mg, 0.005 mmol) was added followed by DIEA (0.175 ml, 1 mmol). The reaction mixture was stirred at RT overnight. The product was precipitated by the addition of 15 mL of diethylether. The organic phase was decanted and the residue dissolved in a mixture of acetonitrile and water. The dye was purified by HPLC on RP-18, linear gradient 20-60% acetonitrile in water/0.1% TFA over 20 min. Yield: 15 mg of MG-CY3 pH (30%). $C_{55}H_{64}ClN_5O_8S_2$ MW 1022.72 g/mol MS$^+$ 984.5.

$^1$H-NMR (MeOD) 8.49 (1H, dd) Cy, 7.89 (1H, d) Cy, 7.88 (1H, s) Cy, 7.86 (1H, s) Cy, 7.84 (1H, d) Cy, 7.36 (1H, d) Cy, 7.33 (2H, d) MG, 7.31 (4H, d) MG, 7.28 (1H, d) Cy, 7.19 (2H, d) MG, 6.19 (4H, d) MG, 6.26 (1H, d) Cy, 6.16 (1H, d), 4.18 (2H, t) MG, 3.96 (2H, t) Cy, 3.41 (2H, t) MG, 3.20 (12H, s), 2.23 (2H, t) Cy, 2.01 (2H, q) MG, 1.75 (2H, m) Cy, 1.66 (2H, m) Cy, 1.63 (6H, s) Cy, 1.51 (6H, s) Cy, 1.39 (2H, m) Cy.

Figure 10A:
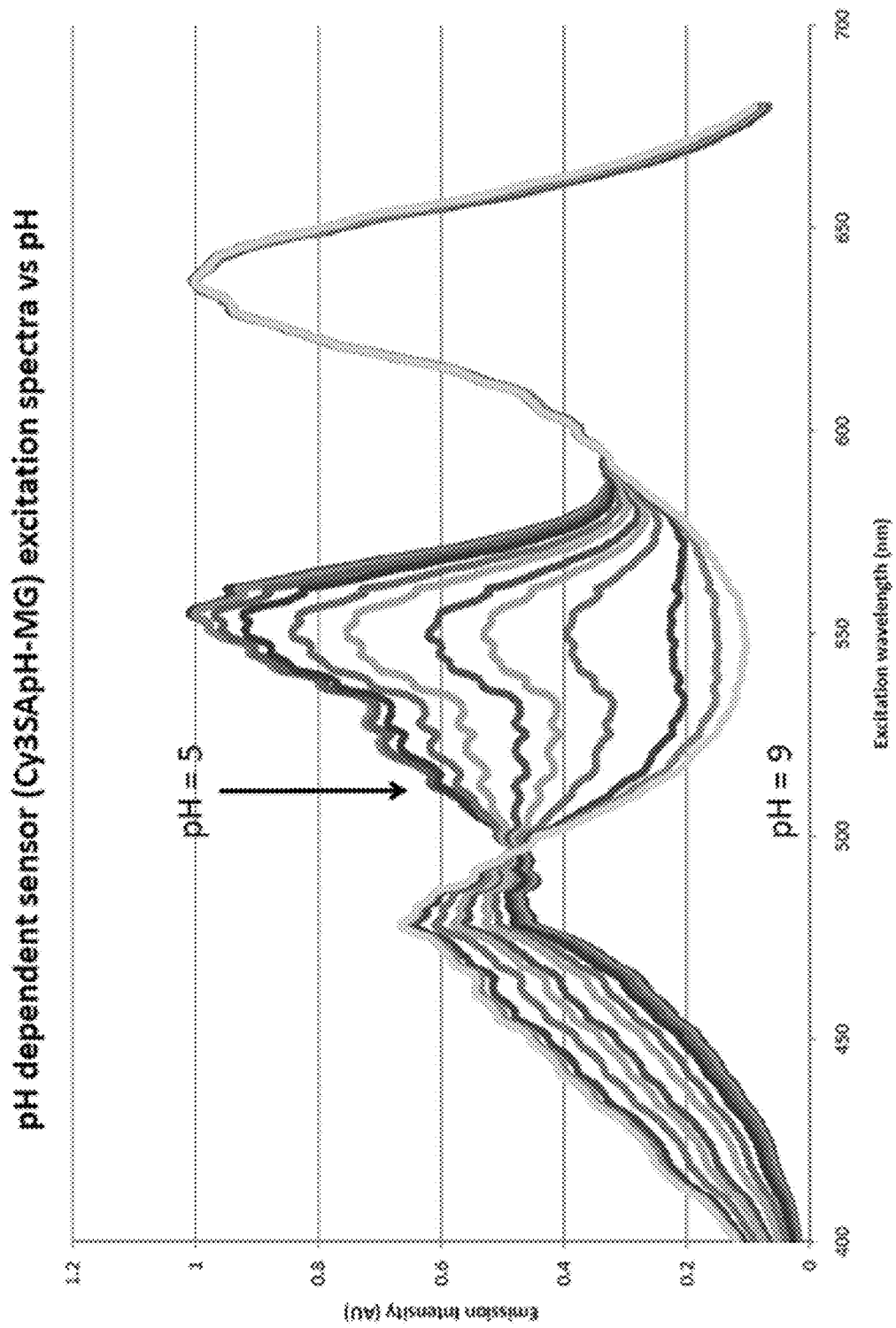
FIGS. 10A and 10B are graphs showing pH dependent sensor (CY3SApH-MG) excitation spectra vs. pH and the ratiometric signature for SACY3 pH+MG+FP (551/633), as described in Example 3.
Figure 10B:
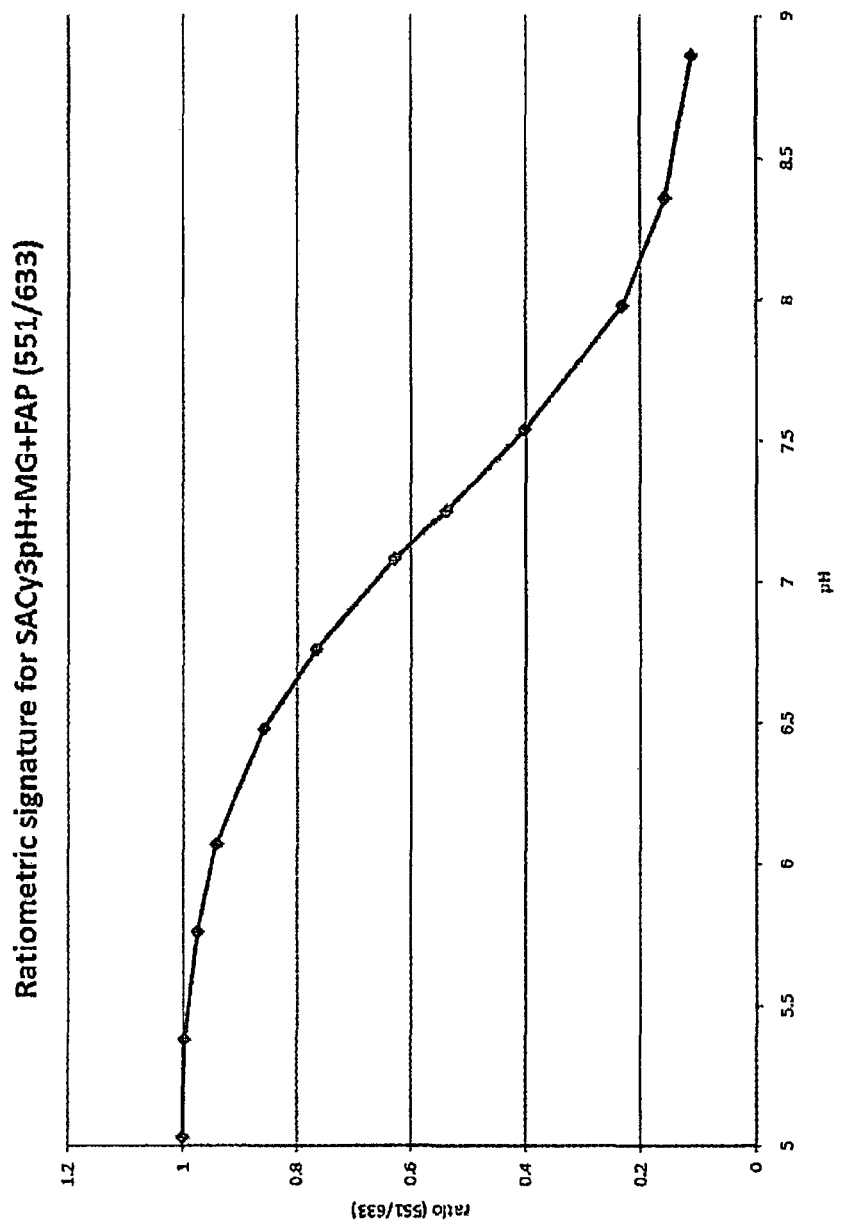
Figure 11A:
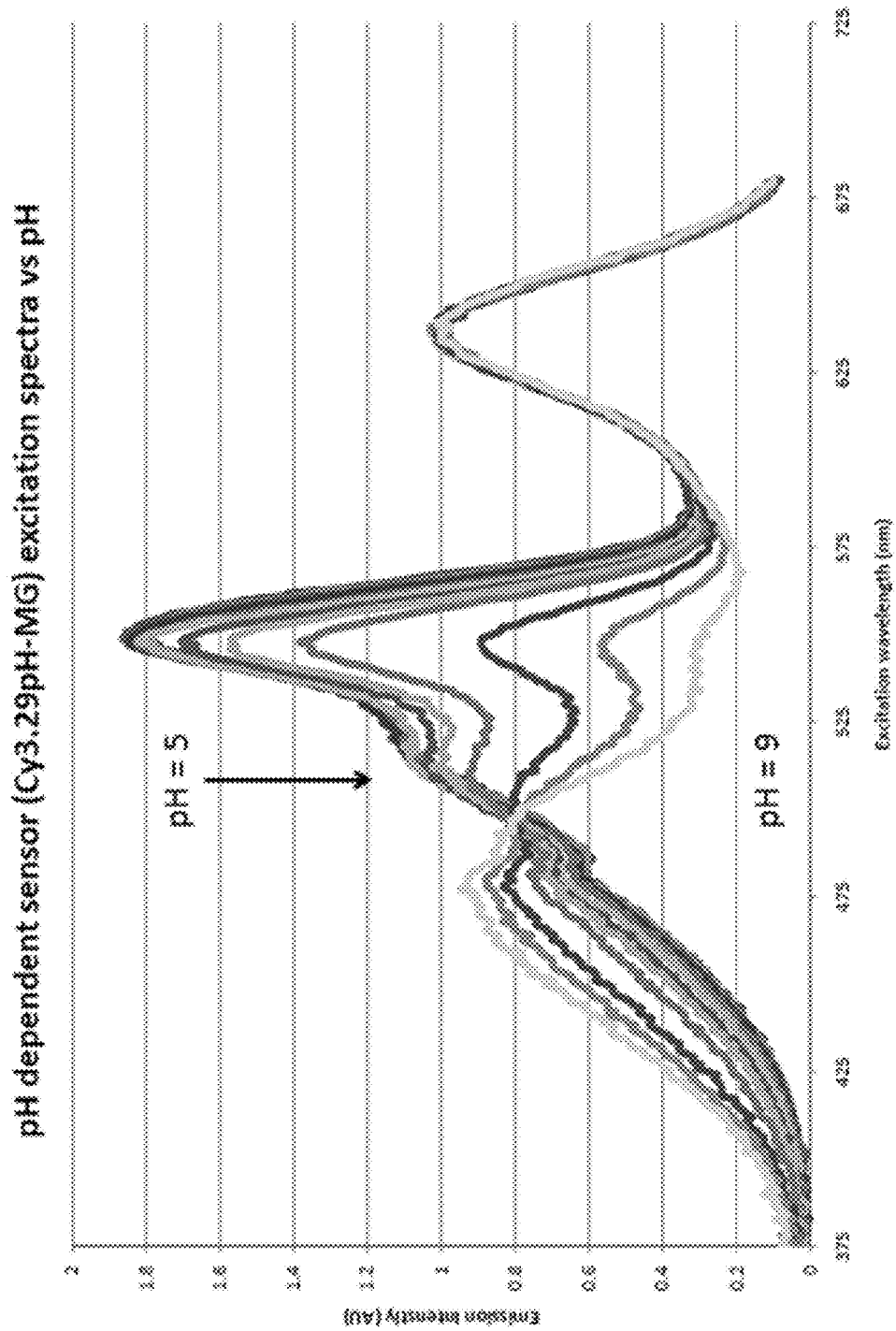
FIGS. 11A and 11B are graphs showing pH dependent sensor (CY3.29SApH-MG) excitation spectra vs. pH and the ratiometric signature for CY3.29SApH-MG (551/633), as described in Example 3
Figure 11B:
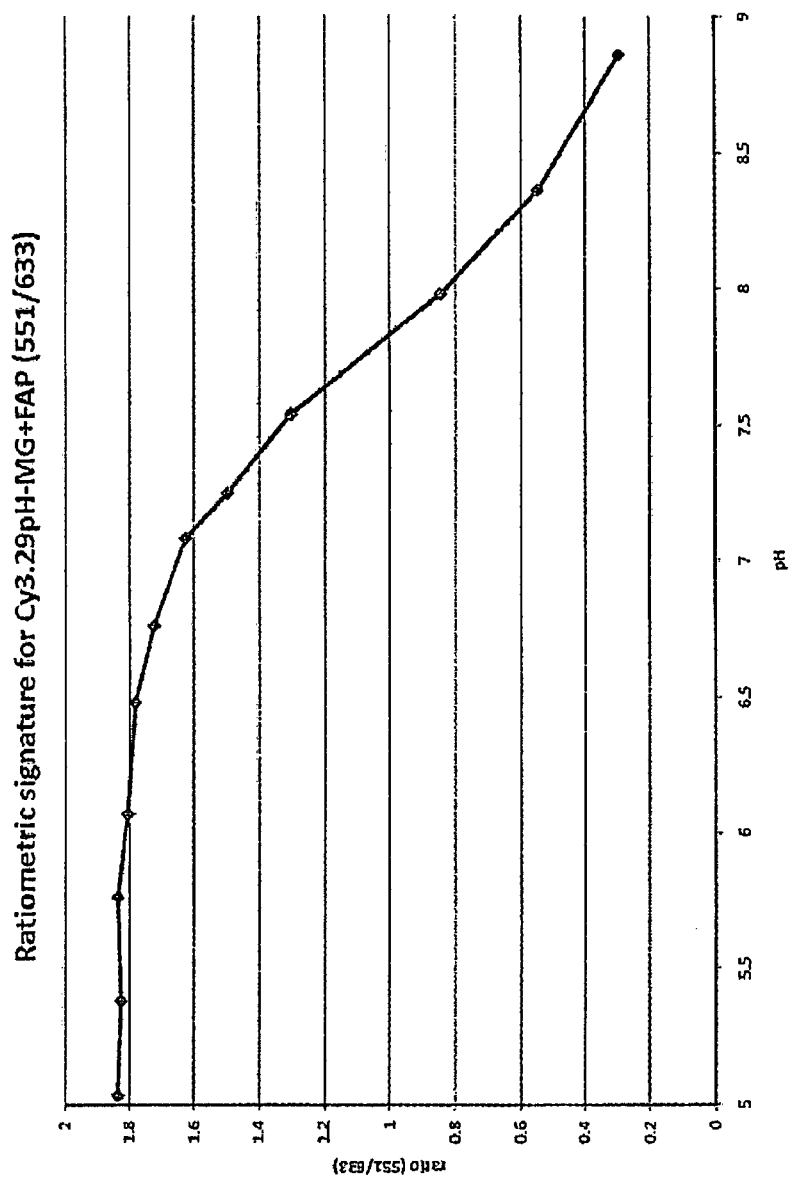

The excitation spectrum and emission spectrum can be seen in FIG. 10 and the ratiometric signature can be seen in FIG. 11.

Figure 12:
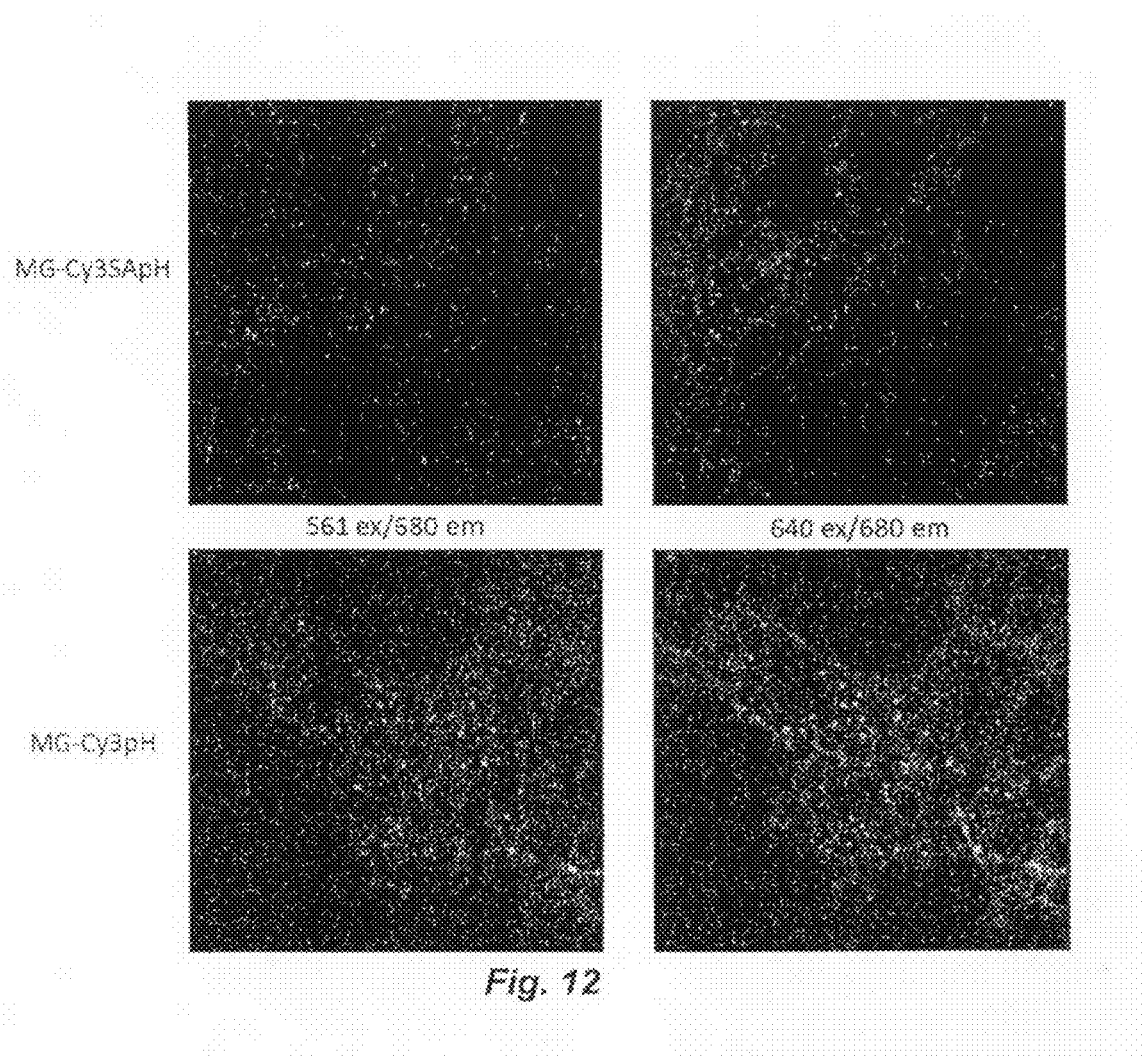
FIG. 12 provides a series of photomicrographs showing effective targeting of a pH-sensitive biosensor as described in Example 3.

Cells expressing the FAP-tagged b2-adrenergic receptor (see below) were exposed to 300 nM dye in DMEM buffer, with 1% serum. After bringing the temperature of the dish to 37 degrees, the cells were treated with 10 uM isoproterenol, an adrenergic receptor specific agonist. The internalization was visualized dynamically, using dual-excitation spinning disk confocal microscopy, with 561 nm excitation and 640 nm excitation for the pH activated and pH independent channels respectively, detected with a 680/30 nm bandpass filter. The grayscale images shown in FIG. 12 represent the independent channels through the mid-plane of the cells after internalization had proceeded for approximately 30 minutes. Note that the cell surface and vesicles are both visible under 640 excitation, while the vesicles alone are visible in the 561 excited channel. This difference in localization reveals a specific signal associated with the acidification of the pH sensitive donor.

A plasmid, pBabeSacLac2-FAP-ADRB2, was prepared by inserting an FAP gene into the plasmid pBabeSacLac2 (see, e.g., Fisher, G W, et al. (2010) Detection and Quantification of β2AR Internalization in Living Cells Using FAP-Based Biosensor Technology *J Biomol Screen* July 2010 vol. 15 no. 6 703-709) through the SfiI sites and the ADRB2 gene is inserted through the BsmI sites, right after the cMyc tag. The amino acid sequence of the expressed polypeptide is provided in FIG. 13A (SEQ ID NO: 12), and the nucleotide sequence of pBabeSacLac2-FAP-ADRB2 is provided in FIG. 13B (SEQ ID NO: 13). We then established a stable NIH 3T3 cell line expressing the FAP-ADRB2 gene. To generate the stable cells: pBabeSacLac2-FAP-ADRB2 was transfected into the packaging cell: phoenix eco cells.

Then the viral supernatant was collected and used to infect NIH3T3 cells. Puromycin was used to select for stable NIH3T3 cells.

Example 4—Functional Assay Using Probes

The probes are targeted to the apical surface of polarized airway epithelial cells. A simple cell surface display system (e.g., pDisplay vector from Invitrogen), is used to display an FAP in an unbiased manner at the apical surface of CFBE41o-cell line. Conventional confocal imaging easily distinguishes the apical surface. An alternative that would result in direct targeting to the apical surface in polarized epithelia would be GPI anchoring. For both the pH- and Ca-sensors, this can be achieved by expressing a GPI addition sequence on the C-terminus of the FAP. The GPI addition sequence from Folate Receptor (SGAGPWAAWP-FLLSLALMLLWLLS (SEQ ID NO: 14)) has been shown to associate with lipid rafts, and is specifically apically targeted in MDCK cells (Paladino et al. (2008) Different GPI-attachment signals affect the oligomerisation of GPI-anchored proteins and their apical sorting *Journal of Cell Science* 121 (24):4001-7). Subsequent studies in primary HBE rely on the lentivirus system discussed above.

Detection of the probe is accomplished by fast switching of the 561 and 635 nm excitation lasers, detecting at the 670 nm channel (for MG emission). The 561 excitation measures the activation of the Rhod-2 by the local $Ca^{2+}$ (through FRET induced MG emission), while the 635 nm excitation determines the total concentration of bound sensor. This will convert Rhod2 from a bulk-loaded, intensity detected probe for calcium concentration changes to a genetically targeted ratiometric and quantitative tool for measuring local $Ca^{2+}$ concentration near specific molecules and in cellular compartments.

Example 5—Synthesis of MG-PEG7-Rhod2 Sodium Salt 2-(4-Hydroxy-3-nitrophenyl)acetic Acid 2

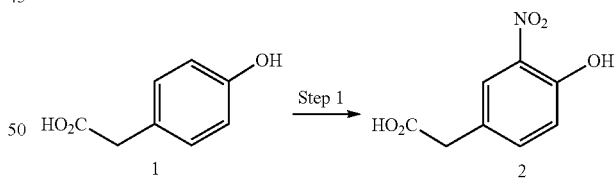

4-Hydroxyphenylacetic acid 1 (31 g; 203.7 mmol) was dissolved in acetic acid (186 mL) and cooled to 5 Celsius on ice bath. Nitric acid (62 mL of 50-70%) was added dropwise to a solution of 4-hydroxyphenylacetic acid for 40 min. and the reaction mixture was held at that temperature for 15 min. The reaction mixture was added into 600 mL of water and filtered precipitate, washed with water, dried. MW $C_8H_7NO_5$ 197.14 g/mol; yield: 27 g (67.2%);

$^1$H-NMR (CD$_3$OD): δ 8.00 (d, 1H); 7.53 (dd, 1H); 7.10 (d, 1H); 3.63 (s, 2H).

Weinstock, J.; Gaitanopoulos, D. E.; Stringer, O. D.; Franz, R. G.; Hieble J. P.; Kinter, L. B.; Mann, W. A.; Flaim, K. E.; Gessner, G. *J. Med. Chem.* 1987, 30, 1166-1176.

Ethyl 2-(4-hydroxy-3-nitrophenyl)acetate 3

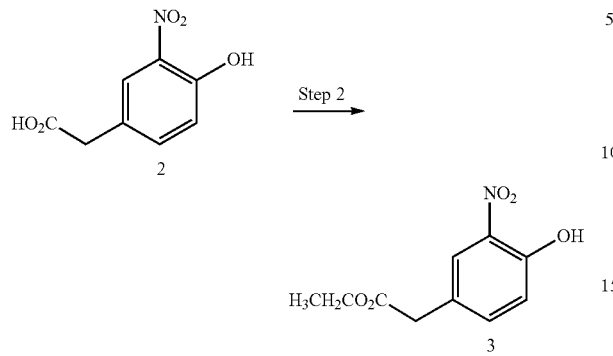

2-(4hydroxy-3-nitrophenyl)acetate 2 (16 g; 81.2 mmol) and sulfuric acid (3 mL of 5 mol/L) were dissolved in ethanol (120 mL) and refluxed for 19 hr. The reaction mixture was cooled to RT and added chloroform and water. The organic phase was extracted with chloroform and washed with water and brine and dried over sodium sulfate. Organic phase was evaporated and added 500 mL of toluene/hexane=1/3. The mixture was cooled in refrigerator overnight. Precipitate was filtered and washed with hexane and dried. MW $C_{10}H_{11}NO_5$ 225.2 g/mol; yield: 16.4 g (89.7%);

$^1$H-NMR (CD$_3$OD): δ 7.99 (d, 1H); 7.52 (dd, 1H); 7.10 (d, 1H); 4.14 (q, 2H); 1.24 (t, 3H).

(4'-Methoxycarbonylethyl-2'-nitrophenoxy)-2-(2''-nitrophenoxy)ethane 4

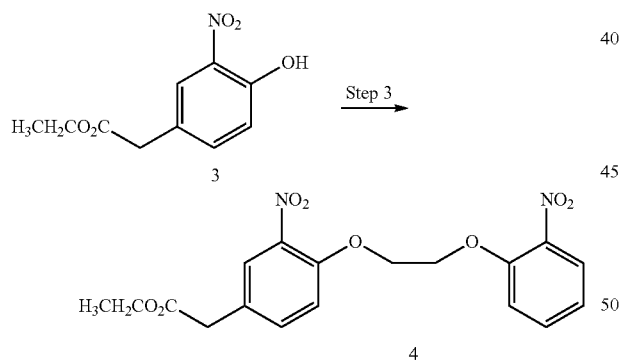

Ethyl 2-(4-hydroxy-3-nitrophenyl)acetate 3 (9.15 g; 40.6 mmol), (2'-nitrophenoxy)-2-bromoethane b (11 g; 44.7 mmol) and K$_2$CO$_3$ (5.65 g; 40.6 mmol) were suspended in 75 mL of DMF and stirred at 90 Celsius for 14 hr, cooled to RT. The reaction mixture was filtered and washed with chloroform. Organic phase was washed with 10% of citric acid and water at 3 times, dried over sodium sulfate, evaporated, added ethanol and cooled in refrigerator overnight. Precipitate was filtered and washed ethanol, dried. MW $C_{18}H_{18}N_2O_8$ 390.34 g/mol; yield: 15.7 g (99.0%);

$^1$H-NMR (CD$_3$OD): δ 7.83 (dd, 1H); 7.78 (d, 1H); 7.66-7.60 (1H); 7.54 (dd, 1H); 7.53-7.39 (2H); 7.15-7.10 (1H); 4.51 (t, 4H); 4.08 (q, 2H); 3.72 (s, 2H); 1.17 (t, 3H).

(2'-Amino-4'-ethoxycarbonylmethyl-1'-phenoxy)-2-(2''-aminophenoxy)ethane 5

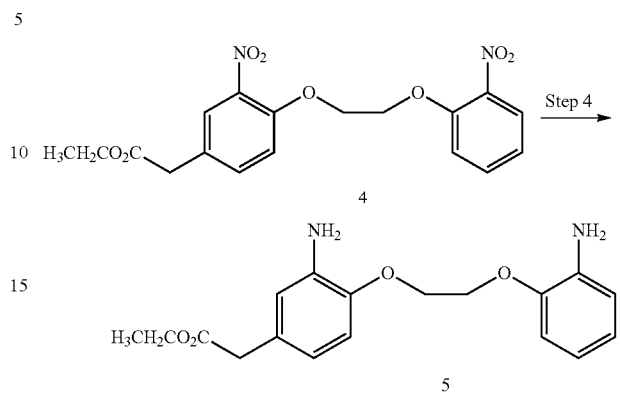

(4'-ethoxycarbonylmethyl-2'-nitrophenoxy)-2-(2''-nitrophenoxy)ethane 4 (14.2 g; 36.4 mmol) was hydrogenated over 10% Pd/C (450 mg) in DMF (72 mL) under H$_2$ gas for 3 days. The mixture was filtered from catalyst through Celite. The mixture was added 200 mL of water, precipitate was filtered and dried. MW $C_{18}H_{22}N_2O_4$ 330.38 g/mol; yield: 10.5 g (88.0%);

$^1$H-NMR (DMSO-d6): δ 6.84 (dd, 1H); 6.78 (d, 1H); 6.71-6.62 (2H); 6.55-6.47 (2H); 6.39 (dd, 1H); 4.68 (s, 4H); 4.24 (t, 4H); 4.04 (q, 2H); 3.41 (s, 2H); 1.16 (t, 3H).

(2'-Amino-4'-carboxymethyl-1'-phenoxy)-2-(2'-aminophenoxy)ethane 6

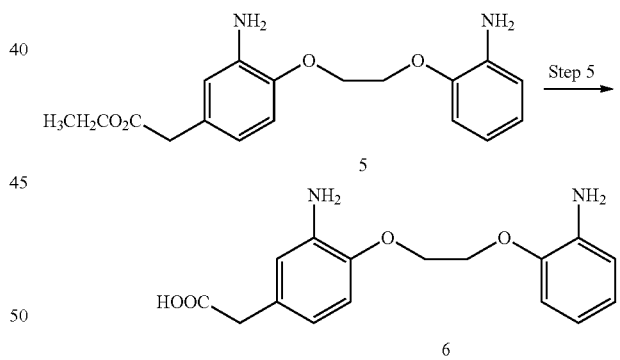

A mixture of (2'-amino-4'-ethoxycarbonylmethyl-1'-phenoxy)-2-(2''-aminophenoxy)ethane 5 (9.5 g; 28.8 mmol), methanol (76 mL), dioxane (76 mL), and 1 M KOH (66.5 mL; 66.5 mmol) was stirred at 45 Celsius for 1 hr, then overnight at RT. The mixture was evaporated and the residue was suspended in H$_2$O (120 mL). Aqueous 2 M HCl was added to pH 5.0. Precipitated product was filtered, washed with H$_2$O, and dried. MW $C_{16}H_{18}N_2O_4$ 302.33 g/mol; yield: 7.94 g (91.3%);

$^1$H-NMR (DMSO-d6): δ 6.84 (dd, 1H); 6.75 (d, 1H); 6.71-6.61 (2H); 6.55-6.47 (2H); 6.37 (dd, 1H); 4.24 (t, 4H); 3.28 (s, 2H).

(2'-Amino-4'-diphenylmethoxycarbonylmethylphenoxy)-2-(2"-aminophenoxy)ethane 7

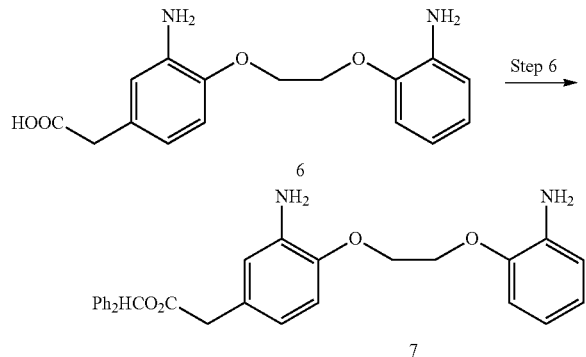

Diphenyldiazomethane was prepared by the way of this article (Javed M. I., Brewer M. *Org. Lett.*, Vol. 9, No. 9, 2007). DMSO (3.07 g; 39.3 mmol) was added in 350 mL of THF under Ar gas and cooled to −55 Celsius. Oxalyl chloride (4.75 g; 37.5 mmol) was added dropwise into this solution for 45 min. and the reaction mixture was held at that temperature for 20 min. And then the reaction mixture was cooled to −78 Celsius. The solution of triethylamine (7.59 g; 75.0 mmol) and diphenylmethanone hydrazine (7 g; 35.7 mmol) was added dropwise into this solution for 40 min. and the reaction mixture was held at that temperature for 2.5 hr and filtered, evaporated. (2'-amino-4'-carboxymethyl-1'-phenoxy)-2-(2"-aminophenoxy)ethane 6 (6 g; 19.8 mmol) was dissolved in 200 mL of acetone and heated to 60 Celsius. Diphenyldiazomethane was added into the solution of 6 and stirred for 18 hr and evaporated. The reaction mixture was suspended in 100 mL of methanol and precipitate was filtered. This precipitate was suspended in hexanes and filtered and washed hexanes. MW $C_{29}H_{28}N_2O_4$ 468.54 g/mol; yield: 6.30 g (67.9%);

$^1$H-NMR (DMSO-d6): δ 7.34-7.22 (m, 10H); 6.84 (dd, 1H); 6.79 (d, 1H); 6.75 (s, 1H); 6.71-6.61 (2H); 6.58 (d, 1H); 6.52-6.47 (m, 1H); 6.42 (dd, 1H); 4.71 (s, 2H); 4.66 (s, 2H); 4.25 (4H); 3.57 (s, 2H).

4-Diphenylmethoxycarbonylmethyl-BAPTA Tetraethyl Ester 8

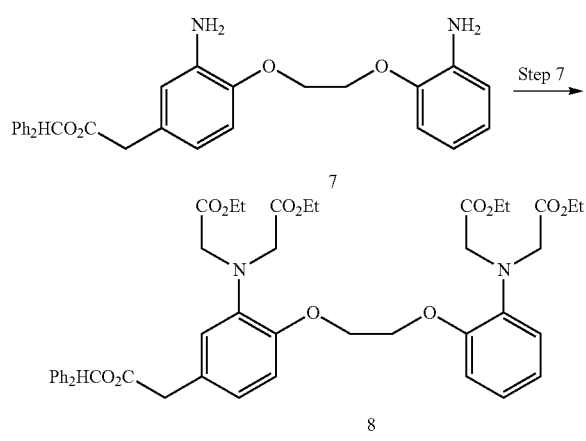

(2'-amino-4'-diphenylmethoxycarbonylmethylphenoxy)-2-(2"-aminophenoxy)ethane 7 (6 g; 12.8 mmol) was dissolved in 250 mL of acetonitrile and heated to 80 Celsius. Methyl bromoacetate (10.7 g; 64 mmol), DIEA (8.27 g; 64 mmol), and KI (10.6 g; 64 mmol) were added into this solution and refluxed for 21 hr. Methyl bromoacetate (2.14 g; 12.8 mmol) was added and stirred for 17 hr. Methyl bromoacetate (10.7 g; 64 mmol) was added and stirred for 7 hr. Methyl bromoacetate (10.7 g; 64 mmol) was added and stirred for 20 hr. The reaction mixture was cooled to RT and evaporated. Ethyl acetate (50 mL) and hexanes (100 mL) were added into the residue and filtered precipitate. Filtrate was evaporated and purified by flash chromatography on a SiO$_2$ column using a gradient of 11-40% ethyl acetate in hexanes as eluent. MW $C_{45}H_{52}N_2O_{12}$ 812.90 g/mol; yield: 9.9 g (95.1%);

$^1$H-NMR (DMSO-d6): δ 7.35-7.24 (m, 10H); 6.93 (dd, 1H); 6.88 (d, 1H); 6.87-6.81 (2H); 6.78 (dd, 1H); 6.77 (s, 1H); 6.71 (dd, 1H); 6.67 (d, 1H); 4.16 (s, 4H); 4.06 (d, 8H); 3.92 (m, 8H); 3.64 (s, 2H); 1.01 (t, 12H).

4-(Diphenylmethoxycarbonylmethyl)-5'-formyl-BAPTA Tetraethyl Ester 9

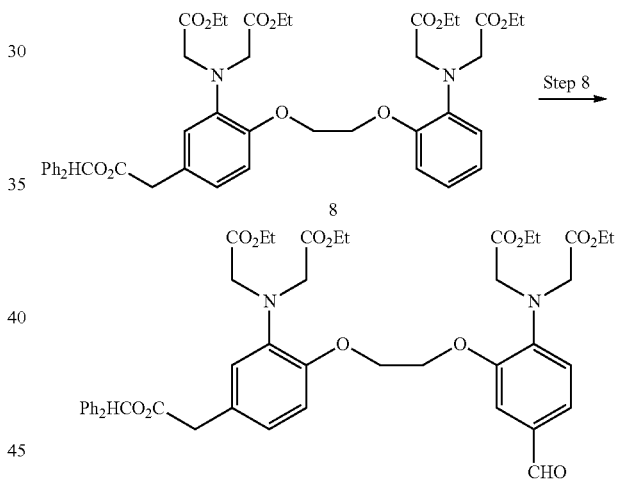

To a solution of Vilsmeier reagent made from POCl3 (0.69 mL; 7.38 mmol) in DMF (1.14 mL) was added a solution of 4-diphenylmethoxycarbonylmethyl-BAPTA tetraethyl ester 8 (4 g; 4.92 mmol) in DMF (20 mL). The mixture was stirred for 1 hr at RT and heated to 70-75 Celsius for 5 hr. The mixture was cooled to RT and added into 500 mL of ice water. The solution was neutralized by 1 M Na$_2$CO$_3$ to pH 7.0. The mixture was extracted with chloroform, dried over sodium sulfate and evaporated. The mixture of products was separated on SiO$_2$ using a gradient of 40-50% ethyl acetate in hexanes. MW $C_{46}H_{52}N_2O_{13}$ 840.91 g/mol; yield: 1.33 g (32.1%);

$^1$H-NMR (DMSO-d6): δ 9.75 (s, 1H); 7.43 (dd, 1H); 7.37 (d, 1H); 7.36-7.24 (m, 10H); 6.88 (dd, 1H); 6.78 (dd, 1H); 6.77 (s, 1H); 6.73 (d, 1H); 6.66 (d, 1H); 4.27-4.12 (m, 4H); 4.18 (s, 4H); 4.03 (s, 4H); 3.96-3.85 (m, 8H); 3.64 (s, 2H); 1.01 (t, 12H).

4-(Diphenylmethoxycarbonylmethyl)-rhod Tetraethyl Ester 10

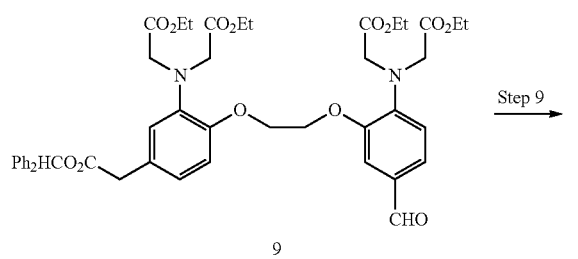

9

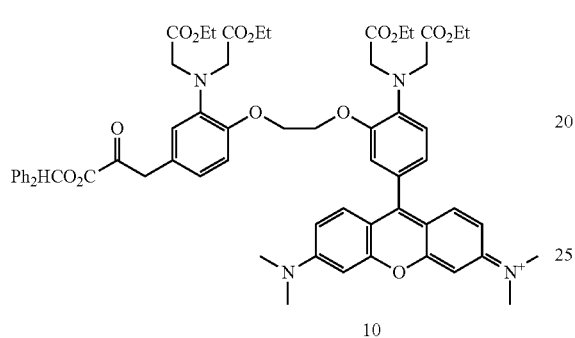

10

A mixture of 4-(diphenylmethoxycarbonylmethyl)-5'-formyl-BAPTA tetraethyl ester 9 (1.2 g; 1.43 mmol), m-dimethylaminophenol (587 mg; 4.28 mmol), and TsOH (25 mg, catalyst) in propionic acid (10 mL) was stirred at 65-68 Celsius for 20 hr, then cooled to RT and poured into 3 M NaOAc (190 mL). After 1 hr, the precipitate was filtered, washed with water, and dried to give 1.511 g of 4-(diphenylmethoxycarbonylmethyl)-dihydrorhod tetraethyl ester.

A mixture of 4-(diphenylmethoxycarbonylmethyl)-dihydrorhod tetraethyl ester (1.511 g; 1.35 mmol) and powdered chloranil (365 mg; 1.48 mmol) in chloroform and methanol (60 mL of each) was stirred for 4 hr, filtered and evaporated. The residue was purified by flash chromatography on $SiO_2$ using a 10% methanol in chloroform as eluent. MW $C_{62}H_{69}N_4O_{13}^+$ 1078.23 g/mol; yield: 537 mg (34.9%);

$^1$H-NMR (DMSO-d6): δ 7.49 (d, 2H); 7.36-7.24 (m, 10H); 7.15 (d, 1H); 7.13 (dd, 2H); 7.04 (dd, 1H); 6.96 (d, 2H); 6.90 (d, 1H); 6.89 (d, 1H); 6.79 (dd, 1H); 6.77 (s, 1H); 6.66 (d, 1H); 4.25 (s, 4H); 4.23-4.16 (m, 4H); 4.03 (s, 4H); 3.99 (q, 4H); 3.91 (q, 4H); 3.66 (s, 2H); 3.26 (s, 12H); 1.04 (t, 6H); 1.02 (t, 6H).

ESI-MS(+): 1077.5.

4-Carboxymethyl-rhod Tetraethyl Ester

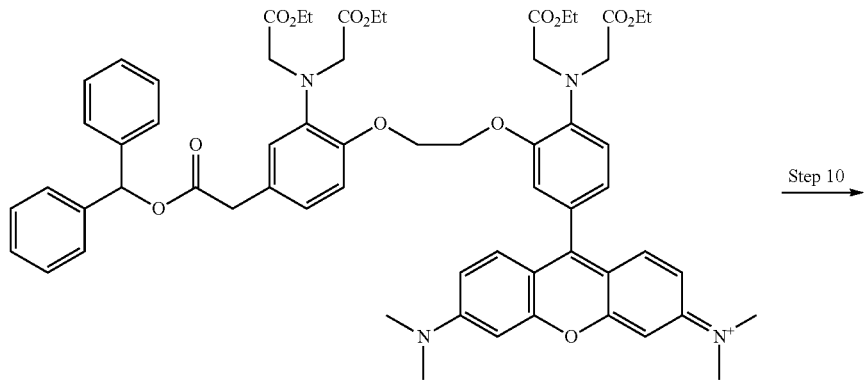

10

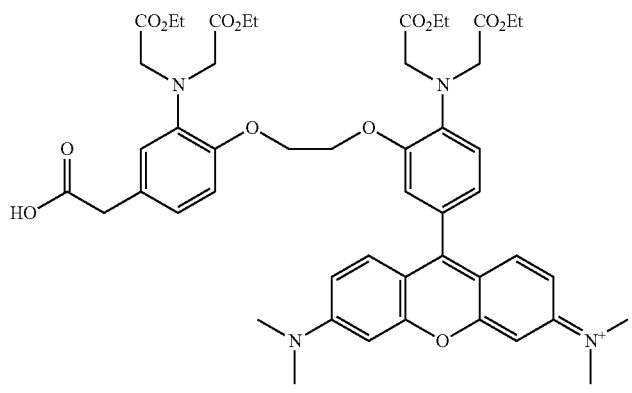

11

A solution of 4-(diphenylmethoxycarbonylmethyl)-rhod tetraethyl ester 10 (400 mg; 0.366 mmol) in chloroform (20 mL) was added TFA (20 mL) and the resulting mixture was stirred for 1 hr, then evaporated and co-evaporated with chloroform (4×30 mL). Ether (50 mL) was added to the residue and the precipitate was filtered and washed with ether (4×10 mL), and dried. MW $C_{49}H_{59}N_4O_{13}^+$ 912.01 g/mol; yield: 325 mg (97.4%);

ESI-MS(+): 911.4.

4-(N-succinimidylcarbonylmethyl)-rhod Tetraethyl Ester 12

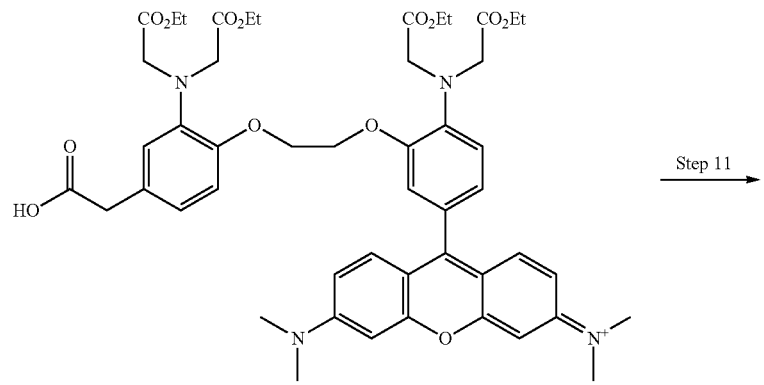

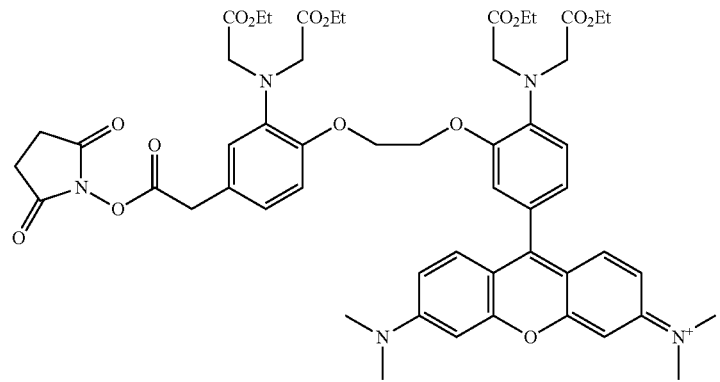

4-carboxymethyl-rhod tetraethyl ester 11 (325 mg; 0.356 mmol), TSTU (128.7 mg; 0.428 mmol), and DIEA (74.5 μL; 0.428 mmol) were dissolved in 5 mL of DMF and stirred for 32 hr at RT. The reaction mixture was evaporated and added ether, precipitate was filtered and dried. MW $C_{53}H_{62}N_5O_{15}^+$ 1009.08 g/mol; yield: 357 mg (99.3%);
ESI-MS(+): 1008.5.
MG(H)-PEG7-Rhod2 tetraethyl Ester 13
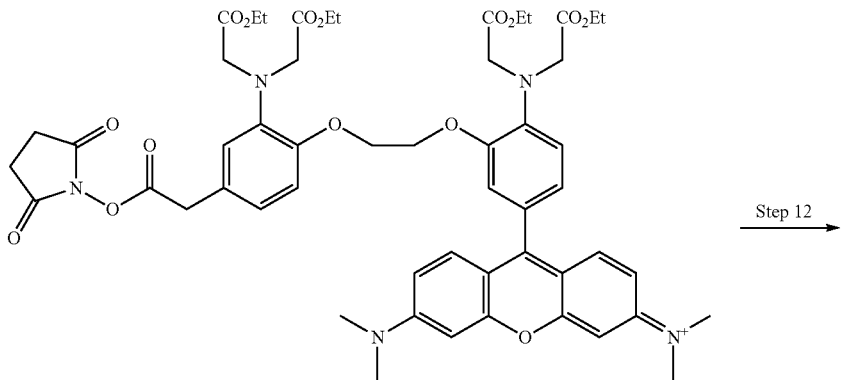
12
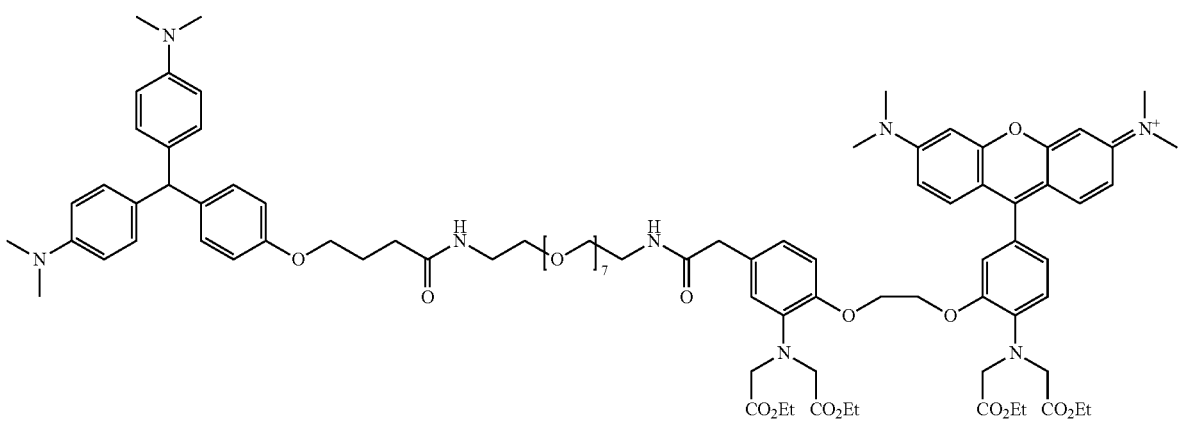
13
MG(H)-PEG7-Rhod2 tetraethyl ester 4-(N-succinimidylcarbonylmethyl)-rhod tetraethyl ester 12 (357 mg; 0.354 mmol), MG(H)-PEG7-NH$_3$$^+$Cl$^-$ i (332.4 mg; 0.425 mmol), and DIEA (308 μL; 1.77 mmol) were dissolved in 3 mL of DMF and stirred for 19 hr. The reaction mixture was added into 50 mL of ether and filtered, washed with ether, dried. The residue was purified by flash chromatography on SiO$_2$ using a 10% methanol in chloroform as eluent. MW C$_{92}$H$_{123}$N$_8$O$_{21}$$^+$ 1677.00 g/mol; yield: 361 mg (60.8%);

ESI-MS(+): 1677.0, 838.9

MG(H)-PEG7-Rhod2 Sodium Salt 14

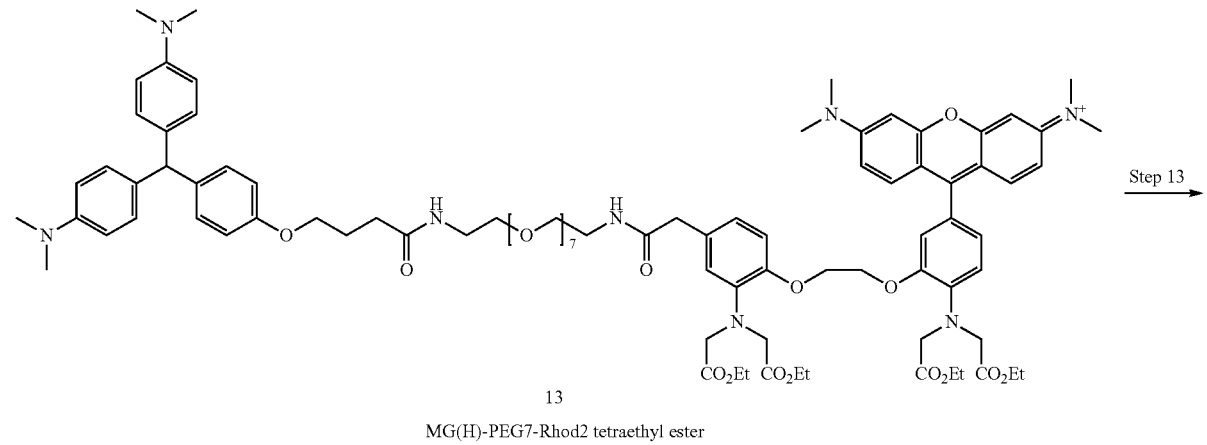

13
MG(H)-PEG7-Rhod2 tetraethyl ester

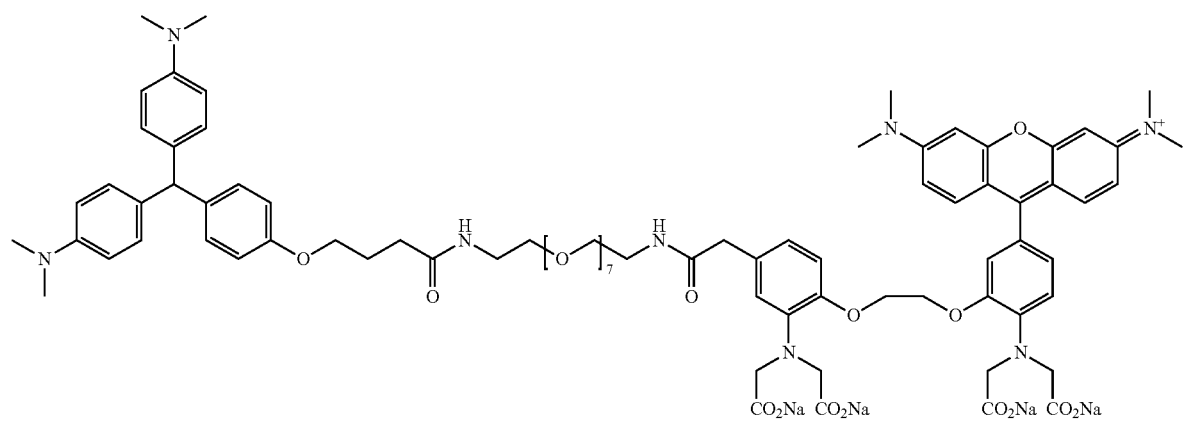

14
MG(H)-PEG7-Rhod2 sodium salt

MG(H)-PEG7-Rhod2 tetraethyl ester 13 (210 mg; 0.125 mmol) was dissolved in methanol and dioxane (3 mL of each), and 1 M NaOH (1 mL; 1 mmol) was added into this solution. The reaction mixture was stirred for 11 hr at RT and neutralized by 2 M HCl to pH 9.0, evaporated. The residue was purified by chromatography on LH-20 using 20% water in methanol as eluent. MW $C_{84}H_{103}N_8Na_4O_{21}^+$ 1652.72 g/mol; yield: 160 mg (77.4%);

ESI-MS(+): 1564.7, 783.5

MG-PEG7-Rhod2 Sodium Salt 18

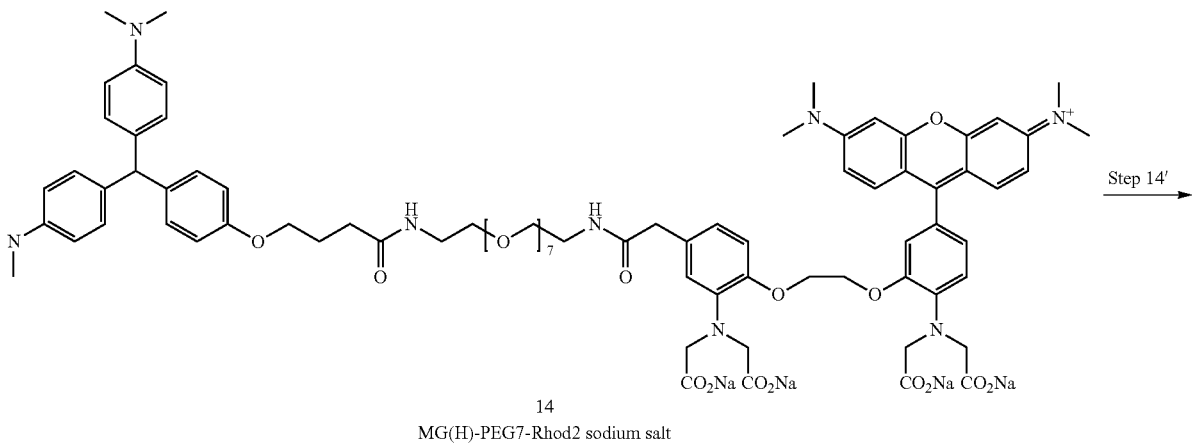

14
MG(H)-PEG7-Rhod2 sodium salt

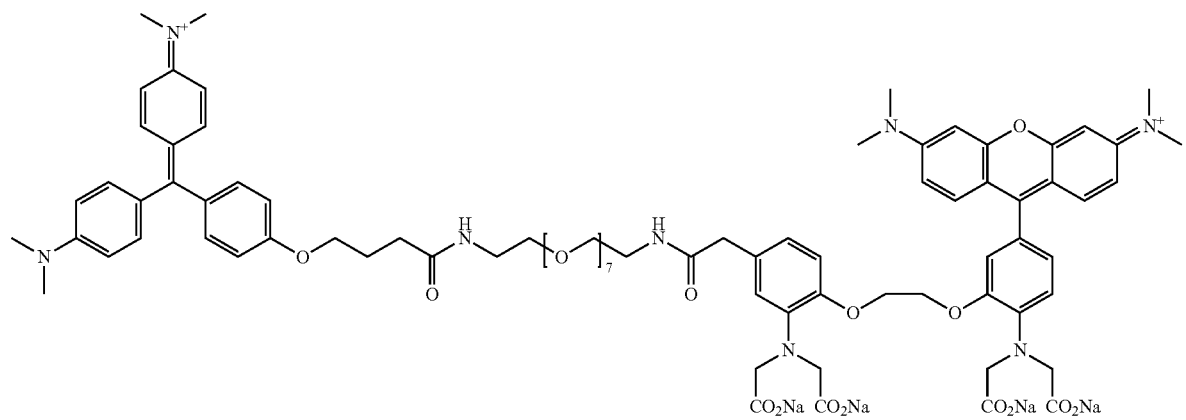

18
MG-PEG7-Rhod2 sodium salt

MG(H)-PEG7-Rhod2 sodium salt 14 (29 mg; 0.0175 mmol) and powdered chloranil (15 mg; 0.0610 mmol) in chloroform and methanol (0.5 mL of each) was stirred for 4 hr, filtered and evaporated. The residue was purified by chromatography on LH-20 using 10% water in methanol as eluent. MW $C_{84}H_{102}N_8Na_4O_{212}^+$ 1651.71 g/mol; yield: 5 mg (17.3%); ESI-MS(+): 781.5, 782.0
Example 6—Synthesis of MG-PEG7-Rhod2 AM
MG(H)-PEG7-Rhod2 15
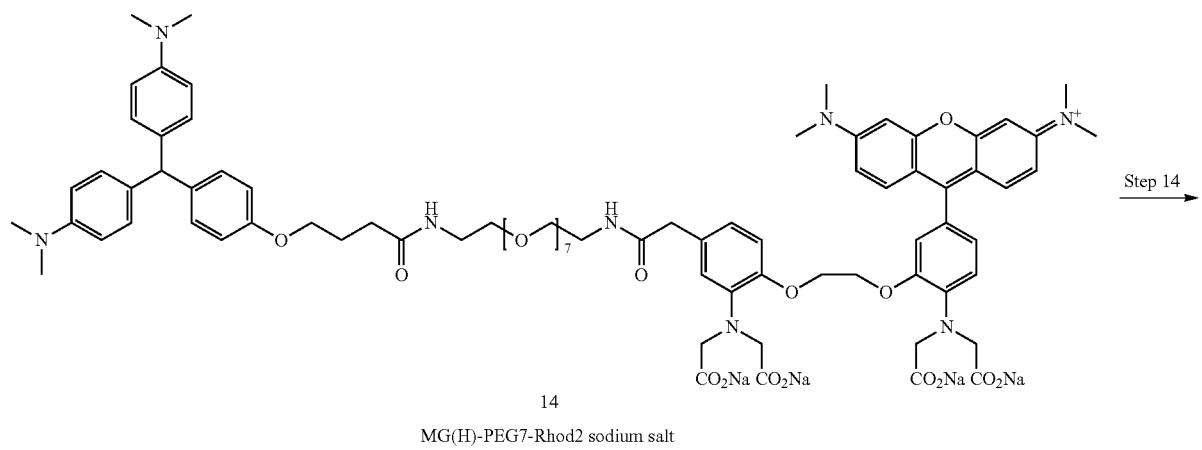
14
MG(H)-PEG7-Rhod2 sodium salt
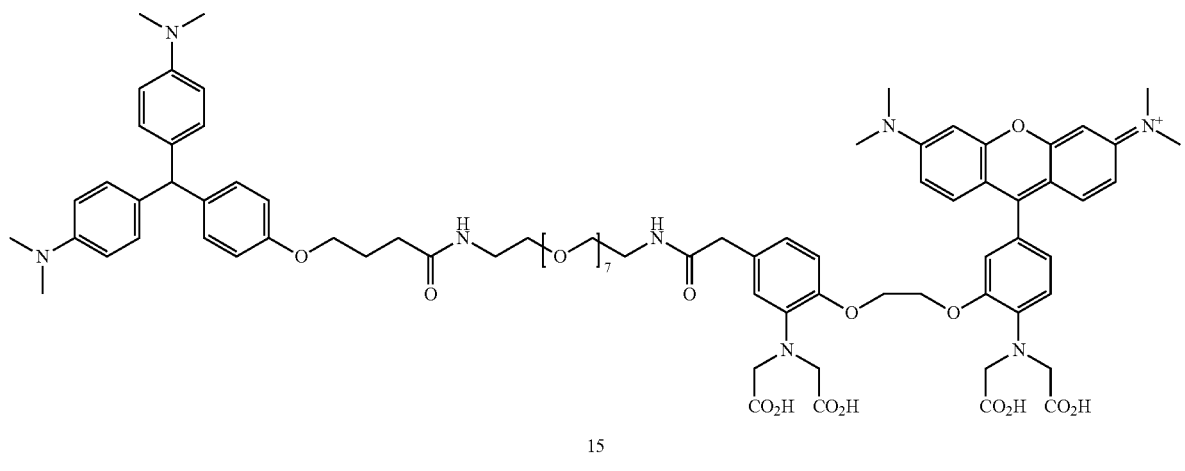
15
MG(H)-PEG7-Rhod2

MG(H)-PEG7-Rhod2 sodium salt 14 (20 mg; 0.0121 mmol) was dissolved in 1 mL of H$_2$O and added 12 M HCl pH to 0.0 and then added 1 M NaOH pH to 0.6. The solution was evaporated and dried. MW C$_{84}$H$_{107}$N$_8$O$_{21}$+ 1564.79 g/mol
MG(H)-PEG7-Rhod2 AM 16
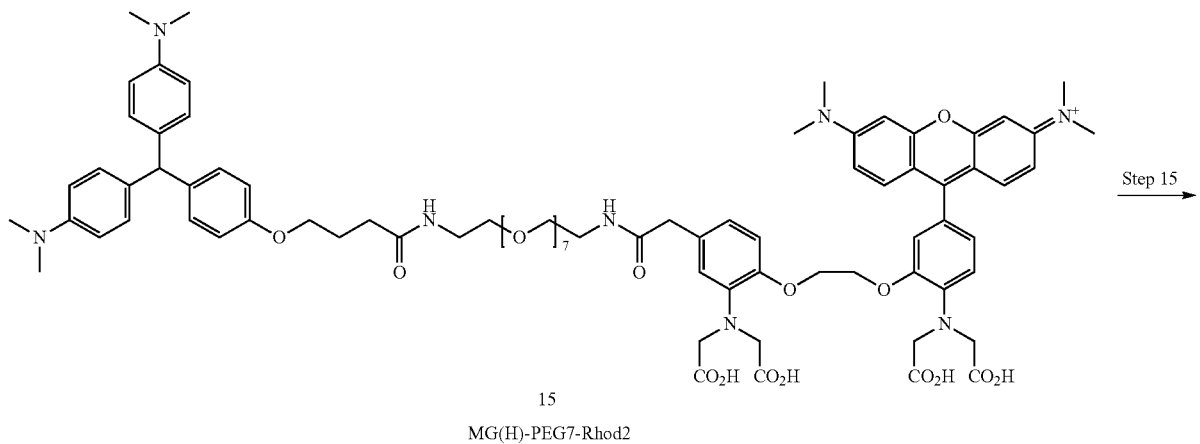
15
MG(H)-PEG7-Rhod2
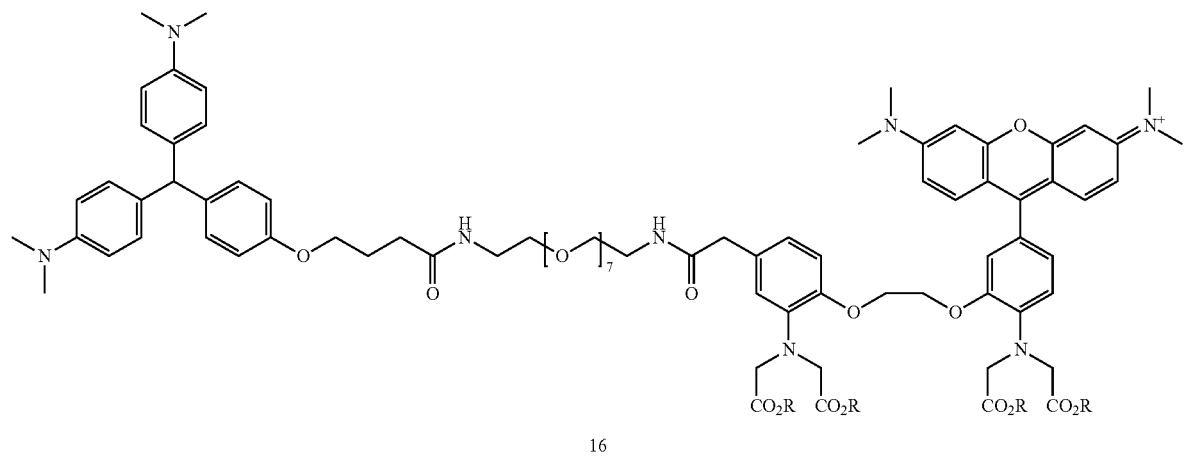
16
MG(H)-PEG7-Rhod2 AM
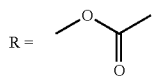
R =

MG(H)-PEG7-Rhod2 15 (62 mg; 0.0396 mmol, contained salt) and DIEA (69 μL; 0.396 mmol), and bromomethyl acetate (38.8 μL; 0.396 mmol) were dissolved in 2 mL of acetonitrile and stirred for 19 hr at RT. The reaction mixture was added into 25 mL of ether and filtered and washed ether, dried. MW $C_{96}H_{123}N_8O_{29}{}^+$ 1853.04 g/mol; yield: 5.5 mg; ESI-MS(+): 1851.9
MG-PEG7-Rhod2 AM 17
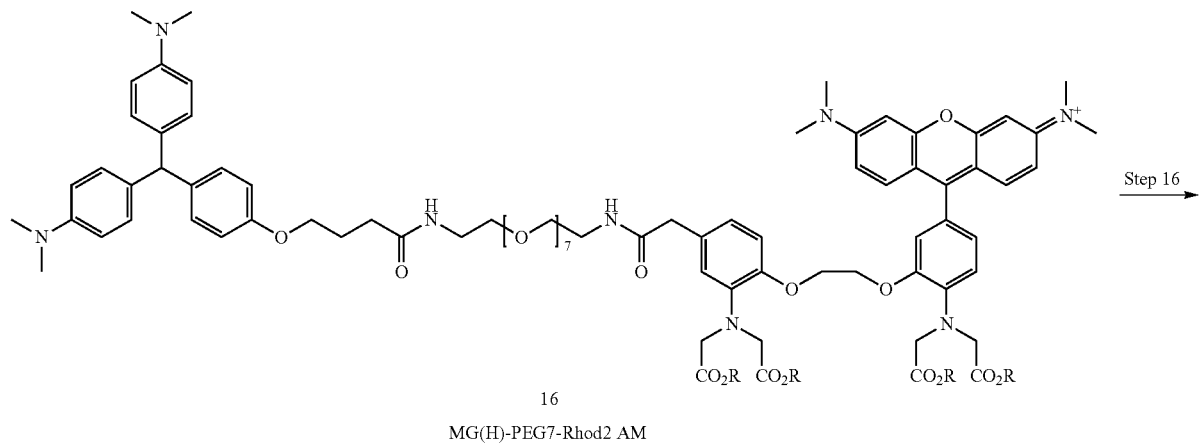
16
MG(H)-PEG7-Rhod2 AM
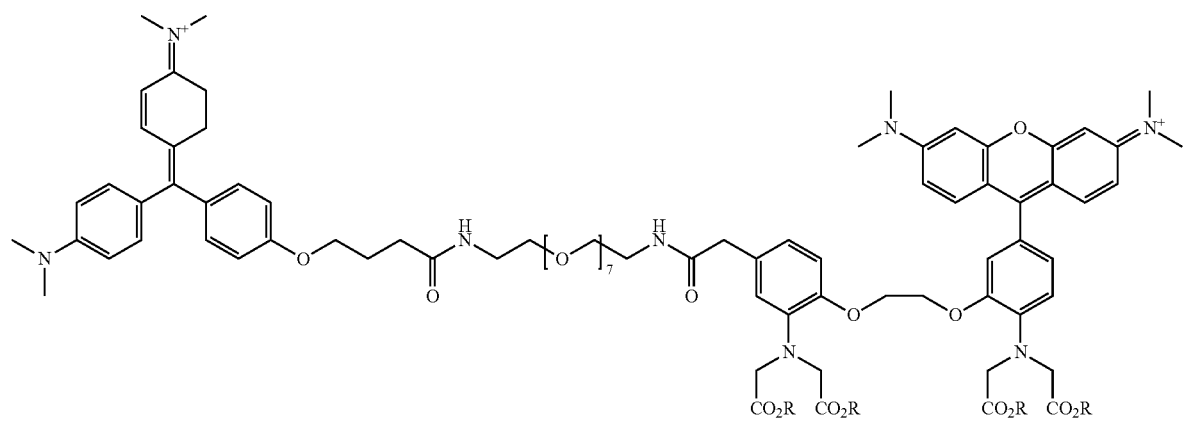
17
MG(H)-PEG7-Rhod2 AM
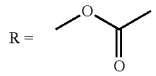

MG(H)-PEG7-Rhod2 AM 16 (5 mg; 2.7 μmol) was dissolved in 1 mL of chloroform and added chloranil (1.0 mg; 4.1 μmol) and stirred 1.5 hr at RT and evaporated. MW $C_{96}H_{122}N_8O_{29}^{2+}$ 1852.03 g/mol; yield: 6.5 mg; ESI-MS(+): 925.9

Example 7—Synthesis of MG(H)-PEG7-$NH_3^+Cl$ (2'-Nitrophenoxy)-2-bromoethane b

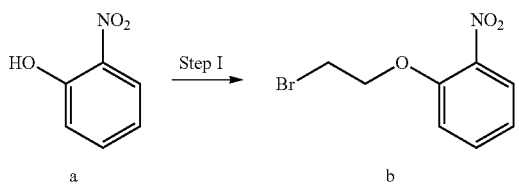 [SMILES: O=[N+]([O-])c1ccccc1O ; O=[N+]([O-])c1ccccc1OCCBr]

1,2-Dibromoethane (202.5 g; 1.078 mol), $K_2CO_3$ (29.8 g; 215.6 mmol), and 2-nitrophenol a (15 g; 107.8 mmol) were suspended in 360 mL of acetonitrile and refluxed for 2.5 hr. The reaction mixture was cooled to RT and filtered, washed with dichloromethane. Filtrate was evaporated and added 300 mL of methanol, cooled in refrigerator overnight. Precipitate was filtered and washed with methanol. MW $C_8H_8BrNO_3$ 246.06 g/mol; yield: 21 g (79.2%);

$^1$H-NMR ($CDCl_3$): δ 7.84 (dd, 1H); 7.60-7.50 (1H); 7.12-7.02 (2H); 4.42 (t, 2H); 3.67 (t, 2H).

4-(Ethylcarbonylpropoxy) benzaldehyde d

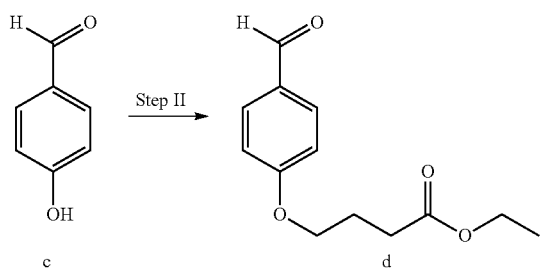 [SMILES: O=Cc1ccc(O)cc1 ; CCOC(=O)CCCOc1ccc(C=O)cc1]

4-Hydroxybenzaldehyde c (10 g; 81.9 mmol), ethyl 4-bromobutyrate (14.1 mL; 98.3 mmol), $K_2CO_3$ (16.99 g; 122.9 mmol), and KI (13.6 g; 81.9 mmol) were suspended in 160 mL of acetonitrile and refluxed for 18 hr. The reaction mixture was cooled to RT and filtered. Filtrate was evaporated and added ethylacetate and filtered. Filtrate was evaporated and dried. MW $C_{13}H_{16}O_4$ 236.26 g/mol; yield: 18.6 g (96.1%);

$^1$H-NMR (DMSO-d6): δ 9.85 (s, 1H); 7.87-7.81 (2H); 7.12-7.06 (2H); 4.13-4.01 (4H); 2.43 (t, 2H); 1.99 (m, 2H); 1.16 (t, 3H).

4-(Ethylcarbonylpropoxy)-Leucomalachite Green e

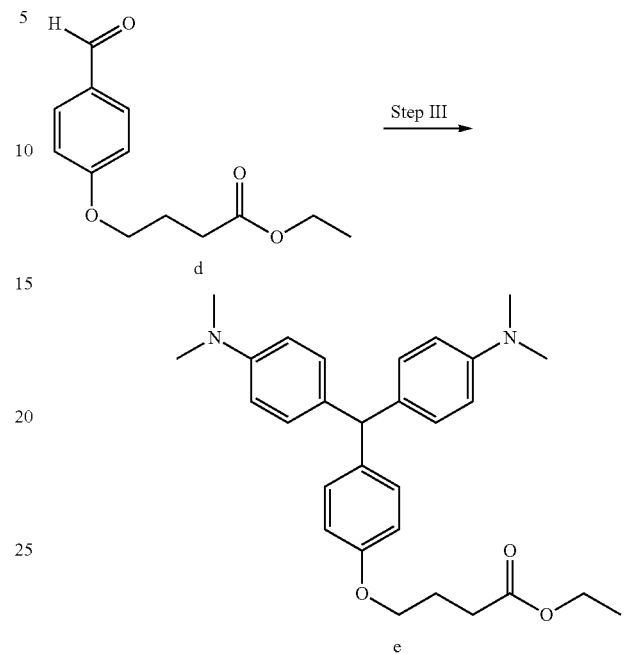

4-(ethylcarbonylpropoxy) benzaldehyde d (7.87 g; 33.3 mmol), N,N-dimethylaniline (11.48 mL; 89.9 mmol), and $ZnCl_2$ (12.27 g; 89.9 mmol) were dissolved in ethanol and refluxed for 23 hr and evaporated. The reaction mixture was added 100 mL of ethanol and refluxed for 22 hr and evaporated. The reaction mixture was added 120 mL of ethanol and refluxed for 18 hr and evaporated. The residue was purified by flash chromatography on $SiO_2$ using 30% ethylacetate in hexanes as eluent. MW $C_{29}H_{36}N_2O_3$ 460.61 g/mol; yield: 7.8 g (33.3%);

$^1$H-NMR (DMSO-d6): δ 6.94 (d, 2H); 6.86 (d, 4H); 6.79 (d, 2H); 6.62 (d, 4H); 5.22 (s, 1H); 4.10-3.98 (q, 2H); 3.92 (t, 2H); 2.82 (s, 12H); 2.42 (t, 2H); 1.93 (m, 2H); 1.16 (t, 3H).

4-(Carboxypropoxy)-Leucomalachite Green f

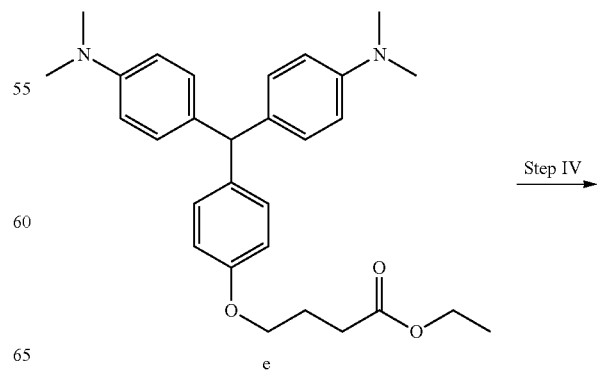

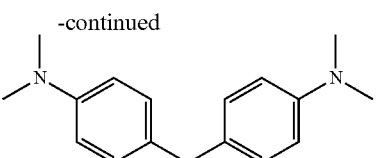

f 4-(Ethylcarbonylpropoxy) Leucomalachite Green e (7.8 g; 16.9 mmol) and 1 M KOH (50 mL; 50 mmol) were dissolved in methanol and dioxane (60 mL of each) and stirred for 4 hr at RT. The reaction mixture was added 100 mL water and neutralized by 2 M HCl to pH 4.0. A precipitate was filtered and washed with water and dried. MW $C_{27}H_{32}N_2O_3$ 432.55 g/mol; yield: 6.5 g (89.2%);

$^1$H-NMR (DMSO-d6): δ 6.90 (d, 2H); 6.83 (d, 4H); 6.80 (d, 2H); 6.62 (d, 4H); 5.22 (s, 1H); 3.91 (t, 2H); 2.82 (s, 12H); 2.34 (t, 2H); 1.89 (m, 2H).

4-(N-succinimidylcarbonylpropoxy)-Leucomalachite Green g

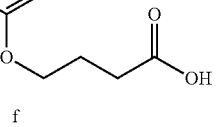

f

Step V →

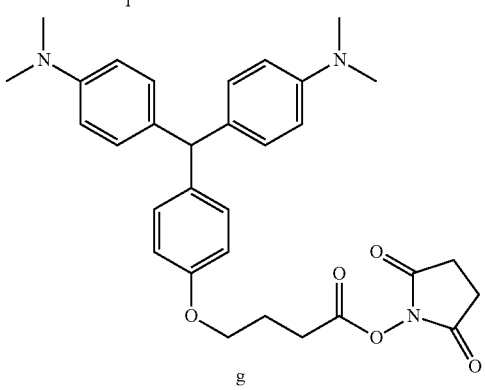

g 4-(Carboxypropoxy)-Leucomalachite Green f (5.85 g; 13.5 mmol), DCC (4.18 g; 20.25 mmol), and NHS (2.33 g; 20.25 mmol) were dissolved in 90 mL of dichloromethane and stirred for 7 hr at RT. The reaction mixture was filtered and filtrate was evaporated. The residue was added ethyl-acetate (100 mL) and filtered. Filtrate was evaporated and dried. MW $C_{31}H_{35}N_3O_5$ 529.63 g/mol; yield: 8.73 g;

$^1$H-NMR (DMSO-d6): δ 6.95 (d, 2H); 6.90-6.80 (6H); 6.62 (d, 4H); 5.23 (s, 1H); 3.99 (t, 2H); 2.84 (s, 12H); 2.04 (m, 2H); 1.80 (m, 2H); 1.63 (m, 2H); 1.22 (m, 2H).

MG(H)-PEG7-Boc h

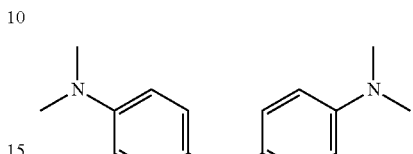

g

Step VI →

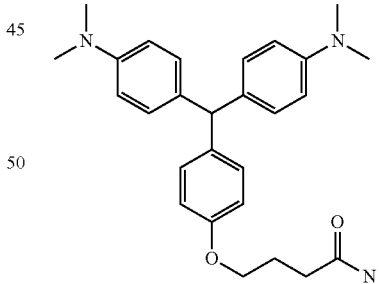

h 4-(N-succinimidylcarbonylpropoxy)-Leucomalachite Green g (542.5 mg; 1.02 mmol), O-(2-Aminoethyl)-O'-[2-(Boc-amino)ethyl]hexaethylene glycol (400 mg; 0.854 mmol), and DIEA (148.6 μL; 0.854 mmol) were dissolved in 10 mL of ethylacetate and stirred for 17 hr at RT. The reaction mixture was filtered and evaporated. The residue was purified by flash chromatography on $SiO_2$ using a gradient of 3-10% methanol in chloroform as eluent. MW $C_{48}H_{74}N_4O_{11}$ 883.12 g/mol; yield: 763 mg (84.3%);

MG(H)-PEG7-NH3+Cl-i

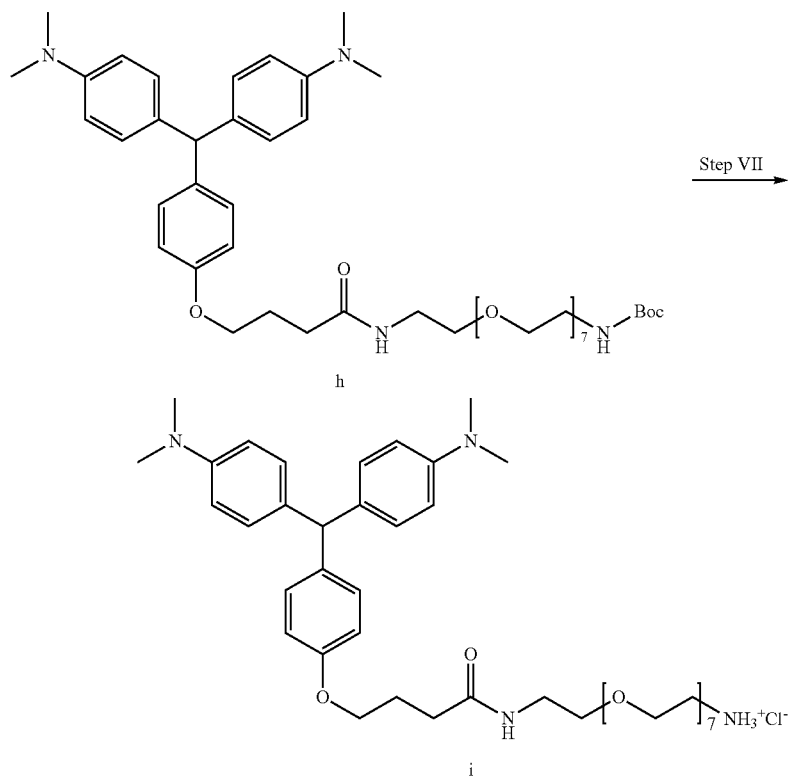

MG(H)-PEG7-Boc h (300 mg; 0.340 mmol) was dissolved in 2 mL of dioxane. 4 M HCl/dioxane solution (1.25 mL) was added into this solution and stirred for 3 hr at RT. The reaction mixture was evaporated and co-evaporated with dioxane (2×20 mL) and chloroform (2×20 mL), and dried. MW $C_{43}H_{67}ClN_4O_9$ 819.47 g/mol; yield: 347 mg; ESI-MS(+): 783.4, 392.3.

Example 8—Functional Assays for MG-PEG7-Rhod2 Sodium Salt

Measurement:

A calcium titration curve for MG-PEG7-Rhod2 sodium salt (compound 18 of Example 8, was measured.

Compound 18 and 2 μL of dL5 (A tandem dimer of L5-MG E52D L91S (FIG. 1A) separated by a G4S linker) is dissolved in each 600 μL of 0 calcium solution[1] (solution A, Invitrogen™ Cat. no. C-3008MP Calcium Calibration Buffer Kit #1) and 600 μL 39 calcium solution (solution B, Invitrogen™ Cat. no. C-3008MP Calcium Calibration Buffer Kit #1). Each volume of A and B solutions was added into 96 well black plate as described in Table 1.

And then, each solution was measured fluorescence by plate reader (TECAN safire2).

Figure 14:
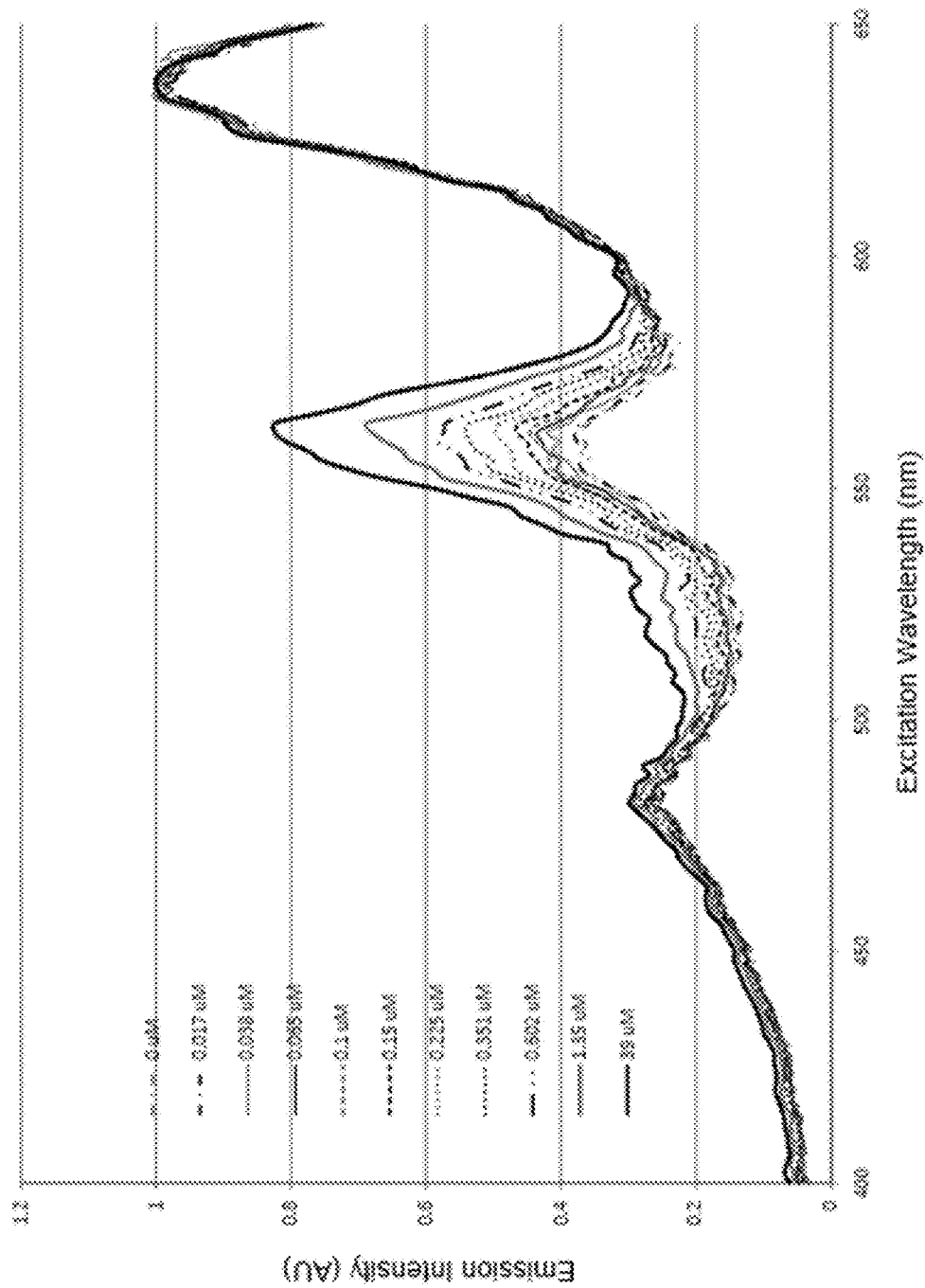
FIG. 14 is a graph showing excitation peaks for various calcium concentrations as described in Example 10.
Figure 15:
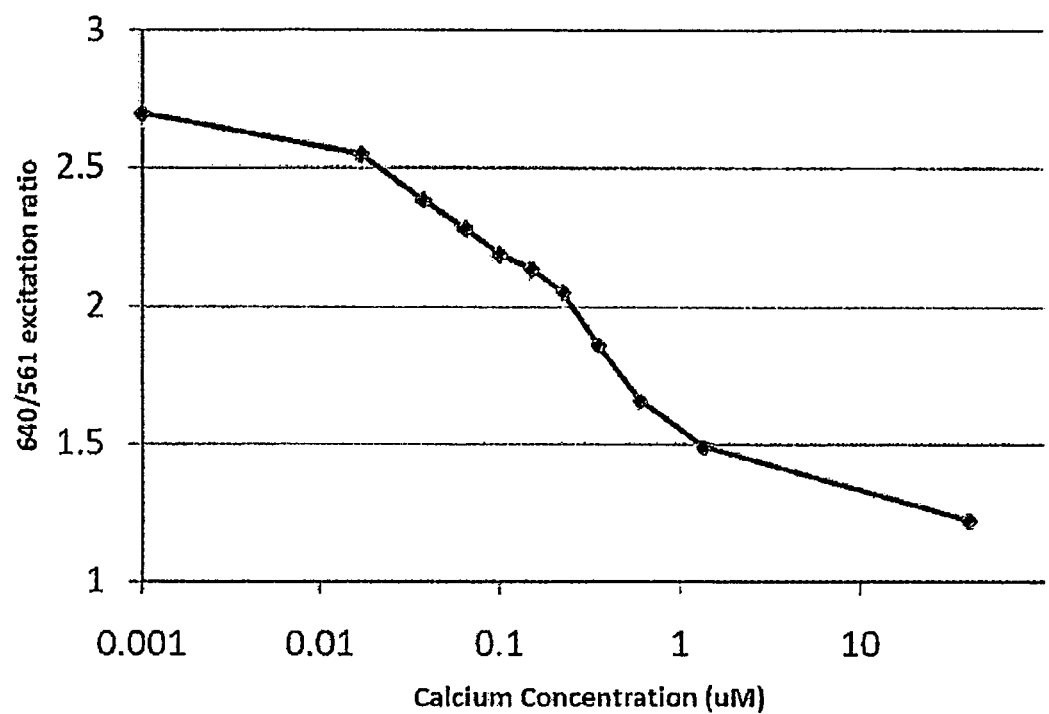
FIG. 15 provides a $Ca^{++}$ titration curve as described in Example 10.

As can be seen in FIG. 14, the ratio of excitation at the center peak in the spectrum (representing the rhod2 excitation) to the mg excitation peak at ~640 nm changes systematically with calcium concentration. The ratio plotted vs the free calcium (FIG. 15) reveals a typical monotonic titration curve showing a mid-point for calcium binding at 0.5 micro molar calcium.

To provide an overall understanding, certain illustrative embodiments are described above; however, it will be understood by one of ordinary skill in the art that the systems and methods described herein can be adapted and modified to provide systems and methods for other suitable applications and that other additions and modifications can be made without departing from the scope of the systems and methods described herein. Unless otherwise specified, the illustrated embodiments can be understood as providing exemplary features of varying detail of certain embodiments, and therefore unless otherwise specified, features, components, modules, and/or aspects of the illustrations can be combined, separated, interchanged, and/or rearranged without departing from the disclosed systems or methods. For all references incorporated herein by reference, this document is to control with respect to any conflicting terms, concepts or definitions.

TABLE 1

| Concentration of Calcium Solutions | | | | | | | | | | | |
|---|---|---|---|---|---|---|---|---|---|---|---|
| Free [$Ca^{++}$] | 0.00 μM | 0.017 μM | 0.038 μM | 0.065 μM | 0.10 μM | 0.15 μM | 0.23 μM | 0.35 μM | 0.60 μM | 1.4 μM | 39 μM |
| Solution A [μL] | 100 | 90 | 80 | 70 | 60 | 50 | 40 | 30 | 20 | 10 | 0 |
| Solution B [μL] | 0 | 10 | 20 | 30 | 40 | 50 | 60 | 70 | 80 | 90 | 100 |

We claim:

1. A complex comprising:

a biosensor comprising malachite green covalently linked by a linker to a single ion-sensitive cyanine dye or an ion-sensitive rhodamine dye that interacts with an analyte ion; and an activator of malachite green bound to the malachite green, wherein the activator comprises one of SEQ ID NOS: 3-9, wherein the malachite green produces a fluorescence signal increase of at least 100-fold when it is bound to the activator as compared to when no activator is bound to the malachite green, wherein the ion-sensitive cyanine dye or ion-sensitive rhodamine dye transfers excitation energy to the malachite green such that, when activated by binding to the activator, the malachite green produces a detectable fluorescent signal when the ion-sensitive cyanine dye or ion-sensitive rhodamine dye is excited and the ion-sensitive cyanine dye or ion-sensitive rhodamine dye transfers different amounts of excitation energy to the malachite green, and the malachite green fluoresces at a different intensity at different analyte ion concentrations, and wherein the ion-sensitive cyanine dye is a trimethine cyanine dye.

2. The complex of claim 1, in which the increase in fluorescence is at least 1000-fold.

3. The complex of claim 1, in which the activator of malachite green is attached to a selectivity component.

4. The complex of claim 3, in which the selectivity component and the activator of malachite green form a fusion protein.

5. The complex of claim 3, in which the selectivity component is crosslinked to the activator of malachite green.

6. The complex of claim 1, in which the activator of malachite green comprises one of SEQ ID NOS: 3-6.

7. The complex of claim 6, in which the activator of malachite green further comprises an amino acid sequence of a selectivity component.

8. The complex of claim 1, wherein the activator of malachite green is linked via a peptide bond or a linker to a targeting group that interacts with a target.

9. The complex of claim 8, wherein the target is one of an epitope, a protein, a modified protein, a nucleic acid, a nucleotide sequence, a small molecule, an active agent, an antibody, a cell, a cell-surface marker, a tissue, a site in an array or a particle.

10. The complex of claim 1, wherein the ion-sensitive trimethine cyanine dye comprises a protonated indole.

11. The complex of claim 1, wherein the fluorescent intensity of the malachite green of the complex is sensitive to pH.

12. The complex of claim 1, wherein the malachite green of the complex fluoresces at different intensities when the ion-sensitive rhodamine dye interacts with different concentrations of calcium or zinc ions.

13. The complex of claim 1, wherein the biosensor is selected from the group consisting of:

103

104

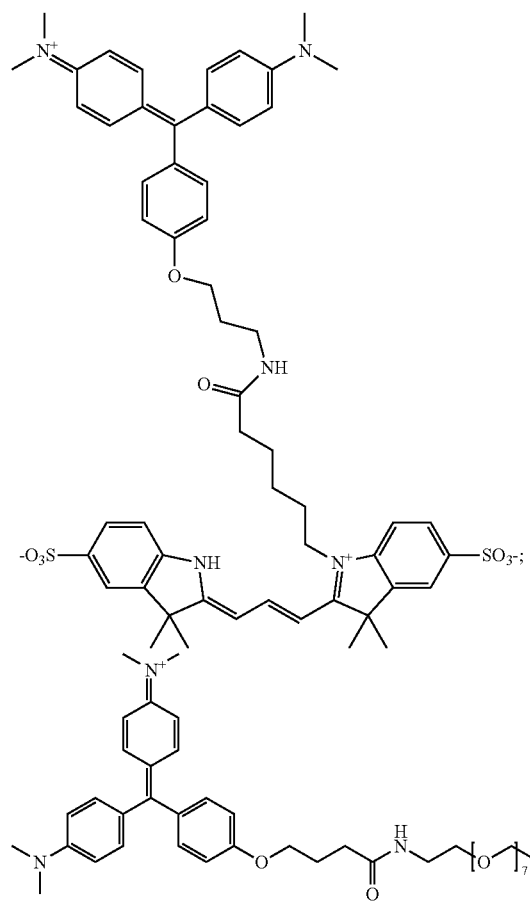

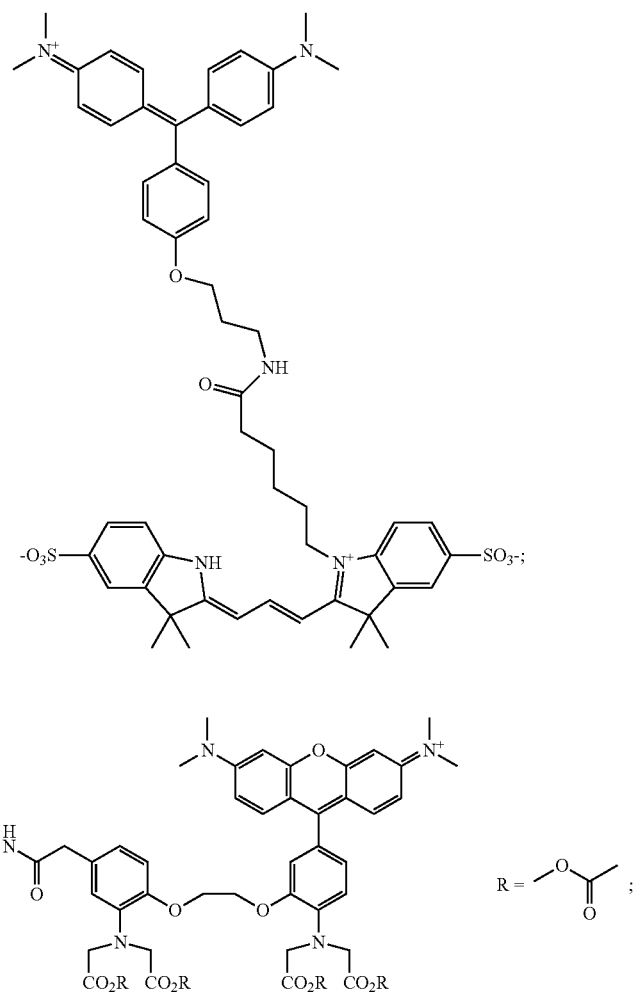

and

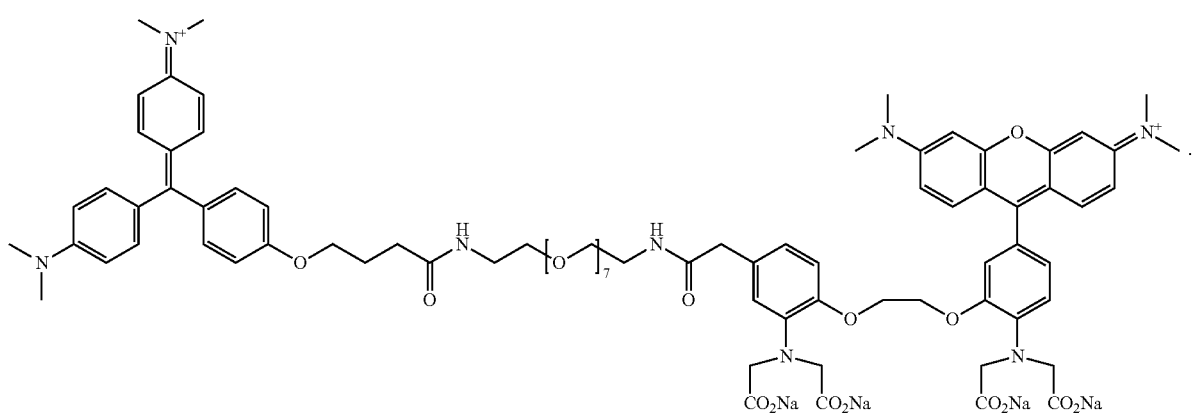

14. An environmental sensing method for detecting the presence of an analyte ion or for quantifying the analyte ion, comprising:

a) contacting a biosensor with an activator of malachite green, wherein the activator comprises one of SEQ ID NOS: 3-9, the biosensor comprising: malachite green covalently linked by a linker to a single ion-sensitive trimethine cyanine dye or an ion-sensitive rhodamine dye that interacts with the analyte ion, wherein the malachite green produces a fluorescence signal increase of at least 100-fold when it is bound to the activator of malachite green as compared to when no activator of malachite green is bound to the malachite green, and wherein the ion-sensitive trimethine cyanine dye or ion-sensitive rhodamine dye transfers excitation energy to the malachite green such that, when activated, the malachite green produces a detectable fluorescent signal when the ion-sensitive trimethine cyanine dye or ion-sensitive rhodamine dye is excited and the ion-sensitive trimethine cyanine dye or ion-sensitive rhodamine dye transfers different amounts of excitation energy to the malachite green when it interacts with the analyte ion as compared to when no analyte ion is present; and b) illuminating the biosensor with light of a wavelength overlapping an excitation spectrum of the ion-sensitive trimethine cyanine dye or ion-sensitive rhodamine dye, but not overlapping the excitation spectrum of the malachite green and measuring emissions from the malachite green.

15. The method of claim 14, further comprising, c) after contacting the biosensor with the activator of malachite green, illuminating the biosensor with light of a wavelength overlapping an excitation spectrum of the malachite green, but not overlapping an excitation spectrum of the ion-sensitive trimethine cyanine dye or ion-sensitive rhodamine dye and measuring emissions from the malachite green.

16. The method of claim 15, further comprising determining a ratio between the emissions obtained from steps b) and c).

17. The method of claim 14, wherein the activator of malachite green comprises a selectivity component.

18. The method of claim 17, wherein the selectivity component binds to an epitope, a protein, a modified protein, a nucleic acid, a nucleotide sequence, a small molecule, an active agent, an antibody, a cell, a cell-surface marker, a tissue, a site in an array or a particle by the selectivity component.

19. The method of claim 14, further comprising comparing the measured emissions from the malachite green to a control sample or to control sample data to determine the presence of or to quantify amounts of the analyte ion.

* * * * *

SEQUENCE LISTING

<160> NUMBER OF SEQ ID NOS: 15

<210> SEQ ID NO 1
<211> LENGTH: 250
<212> TYPE: PRT
<213> ORGANISM: Artificial Sequence
<220> FEATURE:
<223> OTHER INFORMATION: L5-MG E52D pPNL6 fusion protein

<400> SEQUENCE: 1

Met Gln Leu Leu Arg Cys Phe Ser Ile Phe Ser Val Ile Ala Ser Val
1               5                   10                  15

Leu Ala Gln Glu Leu Thr Thr Ile Cys Glu Gln Ile Pro Ser Pro Thr
            20                  25                  30

Leu Glu Ser Thr Pro Tyr Ser Leu Ser Thr Thr Thr Ile Leu Ala Asn
        35                  40                  45

Gly Lys Ala Met Gln Gly Val Phe Glu Tyr Tyr Lys Ser Val Thr Phe
    50                  55                  60

Val Ser Asn Cys Gly Ser His Pro Ser Thr Thr Ser Lys Gly Ser Pro
65                  70                  75                  80

Ile Asn Thr Gln Tyr Val Phe Lys Asp Asn Ser Ser Thr Ile Glu Gly
                85                  90                  95

Arg Tyr Pro Tyr Asp Val Pro Asp Tyr Ala Leu Gln Ala Ser Gly Gly
            100                 105                 110

Gly Gly Ser Gly Gly Gly Gly Ser Gly Gly Gly Gly Ser Ala Ser Gln
        115                 120                 125

Ala Val Val Thr Gln Glu Pro Ser Val Thr Val Ser Pro Gly Gly Thr
    130                 135                 140

Val Ile Leu Thr Cys Gly Ser Ser Thr Gly Ala Val Thr Ser Gly His
145                 150                 155                 160

Tyr Ala Asn Trp Phe Gln Gln Lys Pro Gly Gln Ala Pro Arg Ala Leu
                165                 170                 175

Ile Phe Asp Thr Asp Lys Lys Tyr Pro Trp Thr Pro Gly Arg Phe Ser
            180                 185                 190

Gly Ser Leu Leu Gly Val Lys Ala Ala Leu Thr Ile Ser Asp Ala Gln
        195                 200                 205

Pro Glu Asp Glu Ala Glu Tyr Tyr Cys Leu Leu Ser Asp Val Asp Gly
    210                 215                 220

Tyr Leu Phe Gly Gly Gly Thr Gln Leu Thr Val Leu Ser Gly Ile Leu
225                 230                 235                 240

Glu Gln Lys Leu Ile Ser Glu Glu Asp Leu
                245                 250

<210> SEQ ID NO 2
<211> LENGTH: 813
<212> TYPE: DNA
<213> ORGANISM: Artificial Sequence
<220> FEATURE:
<223> OTHER INFORMATION: pPNL6 L5-MG E52D nucleotide sequence

<400> SEQUENCE: 2
aaaaaacccc ggatcgaatt ctacttcata cattttcaat taagatgcag ttacttcgct      60
gtttttcaat attttctgtt attgcttcag ttttagcaca ggaactgaca actatatgcg     120
agcaaatccc ctcaccaact ttagaatcga cgccgtactc tttgtcaacg actactattt     180
tggccaacgg gaaggcaatg caaggagttt ttgaatatta caatcagta acgtttgtca      240 gtaattgcgg ttctcacccc tcaacaacta gcaaaggcag ccccataaac acacagtatg     300

```
tttttaagga caatagctcg acgattgaag gtagataccc atacgacgtt ccagactacg    360
ctctgcaggc tagtggtggt ggtggttctg gtggtggtgg ttctggtggt ggtggttctg    420
ctagccaggc tgtggtgact caggagccgt cagtgactgt gtccccagga gggacagtca    480
ttctcacttg tggctccagc actggagctg tcaccagtgg tcattatgcc aactggttcc    540
agcagaaacc tggccaagcc cccagggcac ttatatttga caccgacaag aaatatccct    600
ggacccctgg ccgattctca ggctccctcc ttggggtcaa ggctgccctg accatctcgg    660
atgcgcagcc tgaagatgag gctgagtatt actgtttgct ctccgacgtt gacggttatc    720
tgttcggagg aggcacccag ctgaccgtcc tctccggaat tctagaacaa aagcttattt    780
ctgaagaaga cttgtaatag ctcggcggcc gca                                 813
```

<210> SEQ ID NO 3
<211> LENGTH: 110
<212> TYPE: PRT
<213> ORGANISM: Artificial Sequence
<220> FEATURE:
<223> OTHER INFORMATION: scFv sequence

<400> SEQUENCE: 3

```
Gln Ala Val Val Thr Gln Glu Pro Ser Val Thr Val Ser Pro Gly Gly
1               5                   10                  15

Thr Val Ile Leu Thr Cys Gly Ser Ser Thr Gly Ala Val Thr Ser Gly
            20                  25                  30

His Tyr Ala Asn Trp Phe Gln Gln Lys Pro Gly Gln Ala Pro Arg Ala
        35                  40                  45

Leu Ile Phe Glu Thr Asp Lys Lys Tyr Pro Trp Thr Pro Gly Arg Phe
    50                  55                  60

Ser Gly Ser Leu Leu Gly Val Lys Ala Ala Leu Thr Ile Ser Asp Ala
65                  70                  75                  80

Gln Pro Glu Asp Glu Ala Glu Tyr Tyr Cys Leu Leu Ser Asp Val Asp
                85                  90                  95

Gly Tyr Leu Phe Gly Gly Gly Thr Gln Leu Thr Val Leu Ser
            100                 105                 110
```

<210> SEQ ID NO 4
<211> LENGTH: 110
<212> TYPE: PRT
<213> ORGANISM: Artificial Sequence
<220> FEATURE:
<223> OTHER INFORMATION: scFv

<400> SEQUENCE: 4

```
Gln Ala Val Val Thr Gln Glu Pro Ser Val Thr Val Ser Pro Gly Gly
1               5                   10                  15

Thr Val Ile Leu Thr Cys Gly Ser Ser Thr Gly Ala Val Thr Ser Gly
            20                  25                  30

His Tyr Ala Asn Trp Phe Gln Gln Lys Pro Gly Gln Ala Pro Arg Ala
        35                  40                  45

Leu Ile Phe Asp Thr Asp Lys Lys Tyr Pro Trp Thr Pro Gly Arg Phe
    50                  55                  60

Ser Gly Ser Leu Leu Gly Val Lys Ala Ala Leu Thr Ile Ser Asp Ala
65                  70                  75                  80

Gln Pro Glu Asp Glu Ala Glu Tyr Tyr Cys Leu Leu Ser Asp Val Asp
                85                  90                  95

Gly Tyr Leu Phe Gly Gly Gly Thr Gln Leu Thr Val Leu Ser
```

100                 105                 110

<210> SEQ ID NO 5
<211> LENGTH: 110
<212> TYPE: PRT
<213> ORGANISM: Artificial Sequence
<220> FEATURE:
<223> OTHER INFORMATION: scFv

<400> SEQUENCE: 5

Gln Ala Val Val Thr Gln Glu Pro Ser Val Thr Val Ser Pro Gly Gly
1               5                   10                  15

Thr Val Ile Leu Thr Cys Gly Ser Ser Thr Gly Ala Val Thr Ser Gly
            20                  25                  30

His Tyr Ala Asn Trp Phe Gln Gln Lys Pro Gly Gln Ala Pro Arg Ala
        35                  40                  45

Leu Ile Phe Glu Thr Asp Lys Lys Tyr Pro Trp Thr Pro Gly Arg Phe
    50                  55                  60

Ser Gly Ser Leu Leu Gly Val Lys Ala Ala Leu Thr Ile Ser Asp Ala
65                  70                  75                  80

Gln Pro Glu Asp Glu Ala Glu Tyr Tyr Cys Ser Leu Ser Asp Val Asp
                85                  90                  95

Gly Tyr Leu Phe Gly Gly Gly Thr Gln Leu Thr Val Leu Ser
            100                 105                 110

<210> SEQ ID NO 6
<211> LENGTH: 110
<212> TYPE: PRT
<213> ORGANISM: Artificial Sequence
<220> FEATURE:
<223> OTHER INFORMATION: scFv

<400> SEQUENCE: 6

Gln Ala Val Val Thr Gln Glu Pro Ser Val Thr Val Ser Pro Gly Gly
1               5                   10                  15

Thr Val Ile Leu Thr Cys Gly Ser Gly Thr Gly Ala Val Thr Ser Gly
            20                  25                  30

His Tyr Ala Asn Trp Phe Gln Gln Lys Pro Gly Gln Ala Pro Arg Ala
        35                  40                  45

Leu Ile Phe Asp Thr Asp Lys Lys Tyr Pro Trp Thr Pro Gly Arg Phe
    50                  55                  60

Ser Gly Ser Leu Leu Gly Val Lys Ala Ala Leu Thr Ile Ser Asp Ala
65                  70                  75                  80

Gln Pro Glu Asp Glu Ala Glu Tyr Tyr Cys Ser Leu Ser Asp Val Asp
                85                  90                  95

Gly Tyr Leu Phe Gly Gly Gly Thr Gln Leu Thr Val Leu Ser
            100                 105                 110

<210> SEQ ID NO 7
<211> LENGTH: 251
<212> TYPE: PRT
<213> ORGANISM: Artificial Sequence
<220> FEATURE:
<223> OTHER INFORMATION: scFv

<400> SEQUENCE: 7

Gln Val Gln Leu Val Glu Ser Glu Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
            35                  40                  45

Ser Arg Ile Asp Gly Asp Gly Ser Ser Thr Asn Tyr Ala Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ala Glu Asp Thr Ala Val Tyr Tyr Cys
                85                  90                  95

Thr Arg Ala Arg Tyr Phe Gly Ser Val Ser Pro Tyr Gly Met Asp Val
            100                 105                 110

Trp Gly Gln Gly Thr Thr Val Thr Val Ser Ser Gly Ile Leu Gly Ser
            115                 120                 125

Gly Gly Gly Gly Ser Gly Gly Gly Ser Gly Gly Gly Gly Ser Asp
        130                 135                 140

Ile Arg Val Thr Gln Ser Pro Ser Ser Val Ser Ala Ser Val Gly Asp
145                 150                 155                 160

Arg Val Thr Ile Ser Cys Arg Ala Ser Gln Gly Ile Ala Thr Trp Leu
                165                 170                 175

Gly Trp Tyr Gln Gln Lys Pro Gly Lys Pro Pro Gln Leu Leu Ile Tyr
            180                 185                 190

Ser Ala Ser Thr Leu Gln Thr Gly Val Pro Ser Arg Phe Ser Gly Ser
            195                 200                 205

Gly Ser Gly Thr Asp Phe Thr Leu Thr Ile Ser Ser Leu Gln Pro Glu
        210                 215                 220

Asp Val Ala Thr Tyr Tyr Cys Gln Glu Gly Ser Thr Phe Pro Leu Thr
225                 230                 235                 240

Phe Gly Gly Gly Thr Lys Val Asp Ile Lys Ser
                245                 250

<210> SEQ ID NO 8
<211> LENGTH: 130
<212> TYPE: PRT
<213> ORGANISM: Artificial Sequence
<220> FEATURE:
<223> OTHER INFORMATION: scFv

<400> SEQUENCE: 8

Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser Ser
            20                  25                  30

His Tyr Tyr Trp Gly Trp Ile Arg Gln Pro Pro Gly Lys Gly Pro Glu
            35                  40                  45

Trp Ile Gly Ser Met Tyr Tyr Ser Gly Arg Thr Tyr Tyr Asn Pro Ala
    50                  55                  60

Leu Lys Ser Arg Val Thr Ile Ser Pro Asp Lys Ser Lys Asn Gln Phe
65                  70                  75                  80

Phe Leu Lys Leu Thr Ser Val Thr Ala Ala Asp Thr Ala Val Tyr Tyr
                85                  90                  95

Cys Ala Arg Glu Gly Pro Thr His Tyr Tyr Asp Asn Ser Gly Pro Ile
            100                 105                 110

Pro Ser Asp Glu Tyr Phe Gln His Trp Gly Gln Gly Thr Leu Val Thr
            115                 120                 125

Val Ser
    130

<210> SEQ ID NO 9
<211> LENGTH: 109
<212> TYPE: PRT
<213> ORGANISM: Artificial Sequence
<220> FEATURE:
<223> OTHER INFORMATION: scFv

<400> SEQUENCE: 9

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Thr
            20                  25                  30

Tyr Trp Tyr Gln Gln Lys Ala Gly Gln Ala Pro Val Leu Val Ile Tyr
        35                  40                  45

Lys Asp Thr Glu Arg Pro Ser Gly Ile Pro Glu Arg Phe Ser Gly Thr
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Ser Tyr
                85                  90                  95

Val Phe Phe Gly Gly Gly Thr Lys Val Thr Val Leu Ser
                100                 105
```

<210> SEQ ID NO 10
<211> LENGTH: 1675
<212> TYPE: DNA
<213> ORGANISM: Homo sapiens

<400> SEQUENCE: 10

```
gtctgcaagc agacctggca gcattgggct ggccgccccc cagggcctcc tcttcatgcc      60
cagtgaatga ctcaccttgg cacagacaca atgttcgggg tgggcacagt gcctgcttcc     120
cgccgcaccc cagcccccct caaatgcctt ccgagaagcc cattgagtag ggggcttgca     180
ttgcacccca gcctgacagc ctggcatctt gggataaaag cagcacagcc cctaggggc      240
tgcccttgct gtgtggcgcc accggcggtg gagaacaagg ctctattcag cctgtgccca     300
ggaaagggga tcaggggatg cccaggcatg acagtgggt ggcagggggg gagaggaggg      360
ctgtctgctt cccagaagtc caaggacaca aatgggtgag gggactgggc agggttctga     420
ccctgtggga ccagagtgga gggcgtagat ggacctgaag tctccaggga acagggcc       480
caggtctcag gctcctagtt gggcccagtg gctccagcgt ttccaaaccc atccatcccc     540
agaggttctt cccatctctc caggctgatg tgtgggaact cgaggaaata atctccagt      600
gggagacgga ggggtggcca gggaaacggg gcgctgcagg aataaagacg agccagcaca     660
gccagctcat gcgtaacggc tttgtggagc tgtcaaggcc tggtctctgg gagagaggca     720
cagggaggcc agacaaggaa ggggtgacct ggagggacag atccagggc taaagtcctg      780
ataaggcaag agagtgccgg ccccctcttg ccctatcagg acctccactg ccacatagag     840
gccatgattg acccttagac aaagggctgg tgtccaatcc cagccccag ccccagaact      900
ccagggaatg aatgggcaga gagcaggaat gtgggacatc tgtgttcaag gaaggactc      960
caggagtctg ctgggaatga ggcctagtag gaaatgaggt ggcccttgag ggtacagaac    1020
aggttcattc ttcgccaaat tcccagcacc ttgcaggcac ttacagctga gtgagataat    1080
gcctgggtta tgaaatcaaa aagttggaaa gcaggtcaga ggtcatctgg tacagccctt    1140
ccttcccttt tttttttttt tttttttttg tgagacaagg tctctctctg ttgcccaggc    1200
```

```
tggagtggcg caaacacagc tcactgcagc ctcaacctac tgggctcaag caatcctcca   1260
gcctcagcct cccaaagtgc tgggattaca agcatgagcc accccactca gccctttcct   1320 tccttttaa ttgatgcata ataattgtaa gtattcatca tggtccaacc aaccctttct   1380
tgacccacct tcctagagag agggtcctct tgattcagcg gtcagggccc agacccatg    1440 gtctggctcc aggtaccacc tgcctcatgc aggagttggc gtgcccagga agctctgcct   1500
ctgggcacag tgacctcagt gggggtgaggg gagctctccc catagctggg ctgcggccca   1560
accccacccc ctcaggctat gccagggggt gttgccaggg gcacccgggc atcgccagtc   1620
tagcccactc cttcataaag ccctcgcatc ccaggagcga gcagagccag agcat        1675

<210> SEQ ID NO 11
<211> LENGTH: 556
<212> TYPE: DNA
<213> ORGANISM: Homo sapiens

<400> SEQUENCE: 11
agtatctgca gagggccctg cgtatgagtg caagtgggtt ttaggaccag gatgaggcgg     60
ggtgggggtg cctacctgac gaccgacccc gacccactgg acaagcaccc aaccccatt    120 ccccaaattg cgcatcccct atcagagagg gggaggggaa acaggatgcg gcgaggcgcg   180
tgcgcactgc cagcttcagc accgcggaca gtgccttcgc ccccgcctgg cggcgcgcgc   240
caccgccgcc tcagcactga aggcgcgctg acgtcactcg ccggtccccc gcaaactccc   300
cttcccggcc accttggtcg cgtccgcgcc gccgccggcc cagccggacc gcaccacgcg   360
aggcgcgaga taggggggca cgggcgcgac catctgcgct gcggcgccgg cgactcagcg   420
ctgcctcagt ctgcggtggg cagcggagga gtcgtgtcgt gcctgagagc gcagctgtgc   480
tcctgggcac cgcgcagtcc gccccgcgg ctcctggcca gaccacccct aggacccct    540 gccccaagtc gcagcc                                                    556

<210> SEQ ID NO 12
<211> LENGTH: 692
<212> TYPE: PRT
<213> ORGANISM: Artificial Sequence
<220> FEATURE:
<223> OTHER INFORMATION: Expressed FAP sequence for
      pBabeSacLac2-FAP-ADRB2

<400> SEQUENCE: 12

Gln Val Gln Leu Val Glu Ser Glu Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Thr Ile Pro Ile Phe Gly Thr Ala Asp Tyr Ala Gln Glu Phe
    50                  55                  60

Gln Gly Arg Val Thr Ile Thr Thr Asp Glu Ser Thr Ser Thr Ala Tyr
65                  70                  75                  80

Met Glu Leu Ser Gly Leu Arg Ser Glu Asp Thr Ala Val Tyr Tyr Cys
                85                  90                  95

Val Leu Leu Gly Thr Thr Met Val Thr Gly His Tyr Phe Asp Tyr Trp
            100                 105                 110

Gly Gln Gly Thr Leu Val Thr Val Ser Ser Gly Ile Leu Gly Ser Gly
        115                 120                 125
```

-continued

```
Gly Gly Gly Ser Gly Gly Gly Ser Gly Gly Gly Ser Asn Phe
    130             135             140
Met Leu Thr Gln Pro Pro Ser Ala Ser Gly Thr Pro Gly Gln Ser Val
145                 150                 155                 160
Thr Ile Ser Cys Ser Gly Ser Gly Ser Asn Ile Gly Asn Asn Lys Val
                    165                 170                 175
Asn Trp Tyr Gln Gln Leu Pro Gly Thr Ala Pro Lys Leu Leu Ile Tyr
            180                 185                 190
Ser Asn Asn Gln Arg Pro Ser Gly Val Pro Asp Arg Phe Ser Gly Ser
        195                 200                 205
Lys Ser Gly Thr Ser Ala Ser Leu Ala Ile Ser Gly Leu Gln Ser Glu
    210                 215                 220
Asp Glu Ala Asp Tyr Tyr Cys Ala Ala Trp Asp Asp Gly Leu Ser Gly
225                 230                 235                 240
Tyr Val Phe Gly Thr Gly Thr Lys Leu Thr Val Leu Ser Gly Ile Gly
                245                 250                 255
Arg Arg Gly Arg Asp Pro Arg Leu Gln Val Asp Glu Gln Lys Leu Ile
            260                 265                 270
Ser Glu Glu Asp Leu Asn Ala Met Gly Gln Pro Gly Asn Gly Ser Ala
        275                 280                 285
Phe Leu Leu Ala Pro Asn Gly Ser His Ala Pro Asp His Asp Val Thr
    290                 295                 300
Gln Gln Arg Asp Glu Val Trp Val Val Gly Met Gly Ile Val Met Ser
305                 310                 315                 320
Leu Ile Val Leu Ala Ile Val Phe Gly Asn Val Leu Val Ile Thr Ala
                325                 330                 335
Ile Ala Lys Phe Glu Arg Leu Gln Thr Val Thr Asn Tyr Phe Ile Thr
            340                 345                 350
Ser Leu Ala Cys Ala Asp Leu Val Met Gly Leu Ala Val Val Pro Phe
        355                 360                 365
Gly Ala Ala His Ile Leu Met Lys Met Trp Thr Phe Gly Asn Phe Trp
    370                 375                 380
Cys Glu Phe Trp Thr Ser Ile Asp Val Leu Cys Val Thr Ala Ser Ile
385                 390                 395                 400
Glu Thr Leu Cys Val Ile Ala Val Asp Arg Tyr Phe Ala Ile Thr Ser
                405                 410                 415
Pro Phe Lys Tyr Gln Ser Leu Leu Thr Lys Asn Lys Ala Arg Val Ile
            420                 425                 430
Ile Leu Met Val Trp Ile Val Ser Gly Leu Thr Ser Phe Leu Pro Ile
        435                 440                 445
Gln Met His Trp Tyr Arg Ala Thr His Gln Glu Ala Ile Asn Cys Tyr
    450                 455                 460
Ala Asn Glu Thr Cys Cys Asp Phe Phe Thr Asn Gln Ala Tyr Val Ile
465                 470                 475                 480
Ala Ser Ser Ile Val Ser Phe Tyr Val Pro Leu Val Ile Met Val Phe
                485                 490                 495
Val Tyr Ser Arg Val Phe Gln Glu Ala Lys Arg Gln Leu Gln Lys Ile
            500                 505                 510
Asp Lys Ser Glu Gly Arg Phe His Val Gln Asn Leu Ser Gln Val Glu
        515                 520                 525
Gln Asp Gly Arg Thr Gly His Gly Leu Arg Arg Ser Ser Lys Phe Cys
    530                 535                 540
```

```
Leu Lys Glu His Lys Ala Leu Lys Thr Leu Gly Ile Ile Met Gly Thr
545                 550                 555                 560

Phe Thr Leu Cys Trp Leu Pro Phe Phe Ile Val Asn Ile Val His Val
                565                 570                 575

Ile Gln Asp Asn Leu Ile Arg Lys Glu Val Tyr Ile Leu Leu Asn Trp
            580                 585                 590

Ile Gly Tyr Val Asn Ser Gly Phe Asn Pro Leu Ile Tyr Cys Arg Ser
        595                 600                 605

Pro Asp Phe Arg Ile Ala Phe Gln Glu Leu Leu Cys Leu Arg Arg Ser
    610                 615                 620

Ser Leu Lys Ala Tyr Gly Asn Gly Tyr Ser Ser Asn Gly Asn Thr Gly
625                 630                 635                 640

Glu Gln Ser Gly Tyr His Val Glu Gln Glu Lys Glu Asn Lys Leu Leu
                645                 650                 655

Cys Glu Asp Leu Pro Gly Thr Glu Asp Phe Val Gly His Gln Gly Thr
            660                 665                 670

Val Pro Ser Asp Asn Ile Asp Ser Gln Gly Arg Asn Cys Ser Thr Asn
        675                 680                 685

Asp Ser Leu Leu
    690
```

<210> SEQ ID NO 13
<211> LENGTH: 7905
<212> TYPE: DNA
<213> ORGANISM: Artificial Sequence
<220> FEATURE:
<223> OTHER INFORMATION: Nucleotide sequence of pBabeSacLac2-FAP-ADRB2
<220> FEATURE:
<221> NAME/KEY: misc_feature
<222> LOCATION: (3966)..(3966)
<223> OTHER INFORMATION: n is a, c, g, or t

<400> SEQUENCE: 13

```
tgtatttaga aaataaaca  aatagggtt  ccgcgcacat ttccccgaaa agtgccacct     60
gcagcctgaa tatgggccaa acaggatatc tgtggtaagc agttcctgcc ccggctcagg    120
gccaagaaca gatggaacag ctgaatatgg gccaaacagg atatctgtgg taagcagttc    180
ctgccccggc tcagggccaa gaacagatgg tccccagatg cggtccagcc ctcagcagtt    240
tctagagaac catcagatgt ttccagggtg ccccaaggac ctgaaatgac cctgtgcctt    300
atttgaacta accaatcagt tcgcttctcg cttctgttcg cgcgcttctg ctccccgagc    360
tcaataaaag agcccacaac ccctcactcg gggcgccagt cctccgattg actgagtcgc    420
ccgggtaccc gtgtatccaa taaaccctct tgcagttgca tccgacttgt ggtctcgctg    480
ttccttggga gggtctcctc tgagtgattg actacccgtc agcggggggtc tttcatttgg    540 gggctcgtcc gggatcggga ccccctgccc cagggaccac cgacccacca ccggaggta     600 agctggccag caacttatct gtgtctgtcc gattgtctag tgtctatgac tgattttatg    660
cgcctgcgtc ggtactagtt agctaactag ctctgtatct ggcggacccg tggtggaact    720
gacgagttct gaacacccgg ccgcaaccct gggagacgtc ccagggactt gggggccgt     780 ttttgtggcc cgacctgagg aagggagtcg atgtggaatc cgaccccgtc aggatatgtg    840
gttctggtag gagacgagaa cctaaaacag ttcccgcctc cgtctgaatt tttgctttcg    900
gtttggaacc gaagccgcgc gtcttgtctg ctgcagcatc gttctgtgtt gtctctgtct    960
gactgtgttt ctgtatttgt ctgaaaatta gggccagact gttaccactc ccttaagttt   1020
gaccttagat cactggaaag atgtcgagcg gctcgctcac aaccagtcgg tagatgtcaa   1080
```

```
gaagagacgt tgggttacct tctgctctgc agaatggcca accttaacg tcggatggcc      1140
gcgagacggc acctttaacc gagacctcat cacccaggtt aagatcaagg tcttttcacc     1200
tggcccgcat ggacacccag accaggtccc ctacatcgtg acctgggaag ccttggcttt     1260
tgaccccct cctgggtca agccctttgt acacctaag cctccgcctc ctcttcttcc        1320
atccgcgccg tctctccccc ttgaacctcc tctttcgacc ccgcctcaat cctcccttta    1380
tccagccctc actccttctc taggcgccgg ccggatccac tagtaacggc cgccagtgtg    1440
ctggaattcg gcttggggat atccaccatg gagacagaca cactcctgct atgggtactg    1500
ctgctctggg ttccaggttc cactggtgac tatccatatg atgttccaga ttatgctggg    1560
gcccagccgg cctacccata cgacgttcca gactacgctc tgcaggctag tggtggtggt    1620
ggttctggtg gtggtggttc tggtggtggt ggttctgcta ccaggtgca gctggtggaa    1680
tctgaggctg aggtgaagaa gcctgggtcc tcggtgaagg tctcctgcaa ggcctctgga    1740
ggcaccttca gcagctatgc tatcagctgg gtgcggcagg cccctggaca agggcttgag    1800
tggatgggag ggaccatccc tatctttggt acagcagact acgcacagga gttccagggc    1860
agagtcacga ttaccacgga cgaatccacg agcacagcct acatggagct gagcggcctg    1920
agatctgagg acacggccgt gtattactgt gttttgttgg gtacaactat ggttacggga    1980
cactactttg actactgggg ccagggaacc ctggtcaccg tctcctcagg aattctagga    2040
tccggtggcg gtggcagcgg cggtggtggt tccggaggcg gcggttctaa tttatgctg    2100
actcagcccc cctcagcgtc tgggaccccc gggcagagcg tcaccatctc ttgttctgga    2160
agcggctcga acatcggaaa caataaagta aactggtacc agcagctccc aggaacggcc    2220
cccaaactcc tcatctatag taataatcag cggccctcag gggtccctga ccgattctct    2280
ggctccaagt ctggcacctc agcctccctg gccatcagtg ggctccagtc tgaggatgag    2340
gctgattatt actgtgcagc atgggatgac ggtctgagtg gttatgtctt cggaactggg    2400
accaagctca ccgtcctatc cggaattggc cgcaggggcc gggatccgcg gctgcaggtc    2460
gacgaacaaa aactcatctc agaagaggat ctgaatgcta tggggcaacc cgggaacggc    2520
agcgccttct tgctggcacc caatggaagc catgcgccgg accacgacgt cacgcagcaa    2580
agggacgagg tgtgggtggt gggcatgggc atcgtcatgt ctctcatcgt cctggccatc    2640
gtgtttggca atgtgctggt catcacagcc attgccaagt tcgagcgtct gcagacggtc    2700
accaactact tcatcacttc actggcctgt gctgatctgg tcatgggcct agcagtggtg    2760
ccctttgggg ccgccatat tcttatgaaa atgtggactt ttggcaactt ctggtgcgag    2820
ttttggactt ccattgatgt gctgtgcgtc acggccagca ttgagaccct gtgcgtgatc    2880
gcagtggatc gctactttgc cattacttca cctttcaagt accagagcct gctgaccaag    2940
aataaggccc gggtgatcat tctgatggtg tggattgtgt caggccttac ctccttcttg    3000
cccattcaga tgcactggta cagggccacc accaggaag ccatcaactg ctatgccaat    3060
gagacctgct gtgacttctt cacgaaccaa gcctatgtca ttgcctcttc catcgtgtcc    3120
ttctacgttc ccctggtgat catggtcttc gtctactcca gggtctttca ggaggccaaa    3180
aggcagctcc agaagattga caaatctgag ggccgcttcc atgtccagaa ccttagccag    3240
gtggagcagg atgggcggac ggggcatgga ctccgcagat cttccaagtt ctgcttgaag    3300
gagcacaaag ccctcaagac gttaggcatc atcatgggca ctttcacccct ctgctggctg    3360
cccttcttca tcgttaacat tgtgcatgtg atccaggata acctcatccg taaggaagtt    3420
```

-continued

| | | | | | |
|---|---|---|---|---|---|
| tacatcctcc | taaattggat | aggctatgtc | aattctggtt | tcaatcccct | tatctactgc | 3480 |
| cggagcccag | atttcaggat | tgccttccag | gagcttctgt | gcctgcgcag | gtcttctttg | 3540 |
| aaggcctatg | ggaatggcta | ctccagcaac | ggcaacacag | gggagcagag | tggatatcac | 3600 |
| gtggaacagg | agaaagaaaa | taaactgctg | tgtgaagacc | tcccaggcac | ggaagacttt | 3660 |
| gtgggccatc | aaggtactgt | gcctagcgat | aacattgatt | cacaaggag | gaattgtagt | 3720 |
| acaaatgact | cactgctgta | gaatgctgtg | ggccaggaca | cgcaggaggt | catcgtggtg | 3780 |
| ccacactcct | tgcccttaa | ggtggtggtg | atctcagcca | tcctggccct | ggtggtgctc | 3840 |
| accatcatct | cccttatcat | cctcatcatg | ctttggcaga | agaagccacg | tccacagcct | 3900 |
| gggttagctc | actcattagg | cacccaggc | tttacactta | ctgggaaaac | cctggcgtta | 3960 |
| cccaanttaa | tcgccttgca | gcacatcccc | ctttcgccag | ctggcgtaat | agcgaagagg | 4020 |
| cccgcaccga | tcgcccttcc | caacagttgc | gcagcctgaa | tggcgaatgg | cgctttgcct | 4080 |
| ggtttccggc | accagaagcg | gtgccggaaa | gctggctgga | gtgcgatctt | cctgaggccg | 4140 |
| atactgtcgt | cgtcccctca | aactggcgtt | agccagcagg | tggtaggcgg | ccgctcgacc | 4200 |
| ctgtggaatg | tgtgtcagtt | agggtgtgga | aagtccccag | gctccccagc | aggcagaagt | 4260 |
| atgcaaagca | tgcatctcaa | ttagtcagca | accaggtgtg | gaaagtcccc | aggctcccca | 4320 |
| gcaggcagaa | gtatgcaaag | catgcatctc | aattagtcag | caaccatagt | cccgccccta | 4380 |
| actccgccca | tcccgcccct | aactccgccc | agttccgccc | attctccgcc | ccatggctga | 4440 |
| ctaatttttt | ttatttatgc | agaggccgag | gccgcggcct | ctgagctatt | ccagaagtag | 4500 |
| tgaggaggct | tttttggagg | cctaggcttt | tgcaaaaagc | ttaccatgac | cgagtacaag | 4560 |
| cccacggtgc | gcctcgccac | ccgcgacgac | gtccccaggg | ccgtacgcac | cctcgccgcc | 4620 |
| gcgttcgccg | actaccccgc | cacgcgccac | accgtcgatc | cggaccgcca | catcgagcgg | 4680 |
| gtcaccgagc | tgcaagaact | cttcctcacg | cgcgtcgggc | tcgacatcgg | caaggtgtgg | 4740 |
| gtcgcggacg | acggcgccgc | ggtggcggtc | tggaccacgc | cggagagcgt | cgaagcgggg | 4800 |
| gcggtgttcg | ccgagatcgg | cccgcgcatg | gccgagttga | gcggttcccg | gctggccgcg | 4860 |
| cagcaacaga | tggaaggcct | cctggcgccg | caccggccca | aggagcccgc | gtggttcctg | 4920 |
| gccaccgtcg | gcgtctcgcc | cgaccaccag | ggcaagggtc | tgggcagcgc | cgtcgtgctc | 4980 |
| cccggagtgg | aggcggccga | gcgcgccggg | gtgcccgcct | tcctggagac | ctccgcgccc | 5040 |
| cgcaacctcc | ccttctacga | gcggctcggc | ttcaccgtca | ccgccgacgt | cgagtgcccg | 5100 |
| aaggaccgcg | cgacctggtg | catgacccgc | aagcccggtg | cctgacgccc | gccccacgac | 5160 |
| ccgcagcgcc | cgaccgaaag | gagcgcacga | ccccatgcat | cgataaaata | aaagatttta | 5220 |
| tttagtctcc | agaaaaaggg | gggaatgaaa | gaccccacct | gtaggtttgg | caagctagct | 5280 |
| taagtaacgc | cattttgcaa | ggcatggaaa | aatacataac | tgagaataga | gaagttcaga | 5340 |
| tcaaggtcag | gaacagatgg | aacagctgaa | tatgggccaa | acaggatatc | tgtggtaagc | 5400 |
| agttcctgcc | ccggctcagg | gccaagaaca | gatggaacag | ctgaatatgg | ccaaacagg | 5460 |
| atatctgtgg | taagcagttc | ctgccccggc | tcagggccaa | gaacagatgg | tcccagatg | 5520 |
| cggtccagcc | ctcagcagtt | tctagagaac | catcagatgt | ttccagggtg | ccccaaggac | 5580 |
| ctgaaatgac | cctgtgcctt | atttgaacta | accaatcagt | tcgcttctcg | cttctgttcg | 5640 |

```
cgcgcttctg ctccccgagc tcaataaaag agcccacaac ccctcactcg gggcgccagt    5700
cctccgattg actgagtcgc ccgggtaccc gtgtatccaa taaaccctct tgcagttgca    5760
tccgacttgt ggtctcgctg ttccttggga gggtctcctc tgagtgattg actaccgtc    5820 agcgggggtc tttcatttcc gacttgtggt ctcgctgcct tgggagggtc tcctctgagt    5880
gattgactac ccgtcagcgg gggtcttcac atgcagcatg tatcaaaatt aatttggttt    5940
tttttcttaa gtatttacat taaatggcca tagttgcatt aatgaatcgg ccaacgcgcg    6000
gggagaggcg gtttgcgtat tggcgctctt ccgcttcctc gctcactgac tcgctgcgct    6060
cggtcgttcg gctgcggcga gcggtatcag ctcactcaaa ggcggtaata cggttatcca    6120
cagaatcagg ggataacgca ggaaagaaca tgtgagcaaa aggccagcaa aaggccagga    6180
accgtaaaaa ggccgcgttg ctggcgtttt tccataggct ccgcccccct gacgagcatc    6240
acaaaaatcg acgctcaagt cagaggtggc gaaacccgac aggactataa agataccagg    6300
cgtttccccc tggaagctcc ctcgtgcgct ctcctgttcc gaccctgccg cttaccggat    6360
acctgtccgc ctttctccct tcgggaagcg tggcgctttc tcatagctca cgctgtaggt    6420
atctcagttc ggtgtaggtc gttcgctcca agctgggctg tgtgcacgaa ccccccgttc    6480
agcccgaccg ctgcgcctta tccggtaact atcgtcttga gtccaacccg gtaagacacg    6540
acttatcgcc actggcagca gccactggta acaggattag cagagcgagg tatgtaggcg    6600
gtgctacaga gttcttgaag tggtggccta actacggcta cactagaagg acagtatttg    6660
gtatctgcgc tctgctgaag ccagttacct tcggaaaaag agttggtagc tcttgatccg    6720
gcaaacaaac caccgctggt agcggtggtt tttttgtttg caagcagcag attacgcgca    6780
gaaaaaaagg atctcaagaa gatcctttga tcttttctac ggggtctgac gctcagtgga    6840
acgaaaactc acgttaaggg attttggtca tgagattatc aaaaaggatc ttcacctaga    6900
tccttttaaa ttaaaaatga agttttgcggc cgcaaatcaa tctaaagtat atatgagtaa    6960
acttggtctg acagttacca atgcttaatc agtgaggcac ctatctcagc gatctgtcta    7020
tttcgttcat ccatagttgc ctgactcccc gtcgtgtaga taactacgat acgggagggc    7080
ttaccatctg gccccagtgc tgcaatgata ccgcgagacc cacgctcacc ggctccagat    7140
ttatcagcaa taaaccagcc agccggaagg gccgagcgca gaagtggtcc tgcaacttta    7200
tccgcctcca tccagtctat taattgttgc cgggaagcta gagtaagtag ttcgccagtt    7260
aatagtttgc gcaacgttgt tgccattgct acaggcatcg tggtgtcacg ctcgtcgttt    7320
ggtatggctt cattcagctc cggttcccaa cgatcaaggc gagttacatg atcccccatg    7380
ttgtgcaaaa aagcggttag ctccttcggt cctccgatcg ttgtcagaag taagttggcc    7440
gcagtgttat cactcatggt tatggcagca ctgcataatt ctcttactgt catgccatcc    7500
gtaagatgct tttctgtgac tggtgagtac tcaaccaagt cattctgaga atagtgtatg    7560
cggcgaccga gttgctcttg cccggcgtca acacgggata ataccgcgcc acatagcaga    7620
actttaaaag tgctcatcat tggaaaacgt tcttcggggc gaaaactctc aaggatctta    7680
```

-continued

```
ccgctgttga gatccagttc gatgtaaccc actcgtgcac ccaactgatc ttcagcatct    7740
tttactttca ccagcgtttc tgggtgagca aaaacaggaa ggcaaaatgc cgcaaaaaag    7800
ggaataaggg cgacacggaa atgttgaata ctcatactct tccttttttca atattattga   7860 agcatttatc agggttattg tctcatgagc ggatacatat ttgaa                    7905

<210> SEQ ID NO 14
<211> LENGTH: 24
<212> TYPE: PRT
<213> ORGANISM: Homo sapiens

<400> SEQUENCE: 14

Ser Gly Ala Gly Pro Trp Ala Ala Trp Pro Phe Leu Leu Ser Leu Ala
1               5                   10                  15

Leu Met Leu Leu Trp Leu Leu Ser
            20

<210> SEQ ID NO 15
<211> LENGTH: 5
<212> TYPE: PRT
<213> ORGANISM: Artificial Sequence
<220> FEATURE:
<223> OTHER INFORMATION: G4S Linker

<400> SEQUENCE: 15

Gly Gly Gly Gly Ser
1               5
```